US009561265B2

(12) United States Patent
Nishimura et al.

(10) Patent No.: US 9,561,265 B2
(45) Date of Patent: Feb. 7, 2017

(54) KIF20A EPITOPE PEPTIDES FOR TH1 CELLS AND VACCINES CONTAINING THE SAME

(71) Applicant: ONCOTHERAPY SCIENCE, INC., Kanagawa (JP)

(72) Inventors: Yasuharu Nishimura, Kumamoto (JP); Yusuke Tomita, Kumamoto (JP); Ryuji Osawa, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 18 days.

(21) Appl. No.: 14/413,403

(22) PCT Filed: Jul. 9, 2013

(86) PCT No.: PCT/JP2013/004248
§ 371 (c)(1),
(2) Date: Jan. 7, 2015

(87) PCT Pub. No.: WO2014/010231
PCT Pub. Date: Jan. 16, 2014

(65) Prior Publication Data
US 2015/0190489 A1    Jul. 9, 2015

Related U.S. Application Data

(60) Provisional application No. 61/669,999, filed on Jul. 10, 2012.

(51) Int. Cl.
*A61K 38/00* (2006.01)
*A61K 39/00* (2006.01)
*C12N 5/0783* (2010.01)
*C12N 9/14* (2006.01)
*C07K 16/28* (2006.01)
*C07K 16/30* (2006.01)
*C07K 7/06* (2006.01)
*C07K 7/08* (2006.01)
*C07K 14/00* (2006.01)

(52) U.S. Cl.
CPC .......... *A61K 39/0011* (2013.01); *A61K 38/00* (2013.01); *A61K 39/0008* (2013.01); *C07K 7/06* (2013.01); *C07K 7/08* (2013.01); *C07K 14/00* (2013.01); *C07K 16/2833* (2013.01); *C07K 16/30* (2013.01); *C12N 5/0636* (2013.01); *C12N 5/0638* (2013.01); *C12N 9/14* (2013.01); *C12Y 306/04* (2013.01); *A61K 2039/5154* (2013.01); *A61K 2039/5158* (2013.01); *A61K 2039/57* (2013.01); *A61K 2039/70* (2013.01); *C12N 2501/2302* (2013.01); *C12N 2501/2307* (2013.01)

(58) Field of Classification Search
None
See application file for complete search history.

(56) References Cited

U.S. PATENT DOCUMENTS

| 7,745,391 | B2 * | 6/2010 | Mintz ..................... G06F 19/24 514/19.3 |
| 7,998,695 | B2 | 8/2011 | Nakamura et al. |
| 8,383,590 | B2 | 2/2013 | Tsunoda et al. |
| 8,623,829 | B2 | 1/2014 | Tsunoda et al. |
| 8,685,641 | B2 | 4/2014 | Nakamura et al. |
| 8,759,481 | B2 | 6/2014 | Tsunoda et al. |
| 8,883,966 | B2 | 11/2014 | Nishimura et al. |
| 2008/0081768 | A1 * | 4/2008 | Watt ........................ C07K 1/047 506/9 |
| 2008/0301839 | A1 * | 12/2008 | Ravanello ............ C07K 14/415 800/289 |
| 2009/0317392 | A1 | 12/2009 | Nakamura et al. |
| 2010/0040641 | A1 * | 2/2010 | Tsunoda ............. A61K 31/7088 424/185.1 |
| 2012/0014996 | A1 | 1/2012 | Nakamura et al. |

(Continued)

FOREIGN PATENT DOCUMENTS

| WO | 02/101075 | * 12/2002 |
| WO | 2006/085684 A2 | 8/2006 |

(Continued)

OTHER PUBLICATIONS

U.S. Appl. No. 14/989,741, filed Jan. 6, 2016, 127 pages.
Naylor, et al., "Peptide Based Vaccine Approaches for Cancer—A Novel Approach Using a WT-1 Synthetic Long Peptide and the IRX-2 Immunomodulatory Regimen," *Cancers* vol. 3 (4), pp. 3991-4009 (Oct. 25, 2011).
International Search Report from Interntional Application No. PCT/JP2013/004248, dated Sep. 24, 2013.
Allan, et al., "Membrane motors," Curr Opin Cell Biol., vol. 11(4), pp. 476-482 (Aug. 1999).
Belli, et al., "Vaccination of Metastatic Melanoma Patients With Autologous Tumor-Derived Heat Shock Protein gp96-Peptide Complexes: Clinical and Immunologic Findings," J Clin Oncol., vol. 20(20), pp. 4169-4180 (Oct. 15, 2002).

(Continued)

*Primary Examiner* — Sheela J Huff
(74) *Attorney, Agent, or Firm* — Kilpatrick Townsend & Stockton LLP

(57) ABSTRACT

Isolated KIF20A-derived epitope peptides having Th1 cell inducibility are disclosed herein. Such peptides can be recognized by MHC class II molecules and induce Th1 cells. In preferred embodiments, such a peptide of the present invention can promiscuously bind to MHC class II molecules and induce KIF20A-specific cytotoxic T lymphocytes (CTLs) in addition to Th1 cells. Such peptides are thus suitable for use in enhancing immune response in a subject, and accordingly find use in cancer immunotherapy, in particular, as cancer vaccines. Also disclosed herein are polynucleotides that encode any of the aforementioned peptides, APCs and Th1 cells induced by such peptides and methods of induction associated therewith. Pharmaceutical compositions that comprise any of the aforementioned components as active ingredients find use in the treatment and/or prevention of cancers or tumors.

14 Claims, 23 Drawing Sheets

(56) References Cited

U.S. PATENT DOCUMENTS

| | | | | |
|---|---|---|---|---|
| 2013/0330335 | A1* | 12/2013 | Bremel | G06F 19/18 424/134.1 |
| 2014/0141027 | A1 | 5/2014 | Tsunoda et al. | |
| 2014/0248300 | A1 | 9/2014 | Tsunoda et al. | |
| 2015/0017193 | A1 | 1/2015 | Nishimura et al. | |

FOREIGN PATENT DOCUMENTS

| | | |
|---|---|---|
| WO | 2007/013665 A2 | 2/2007 |
| WO | 2008/102557 A1 | 8/2008 |
| WO | 2008/102906 A1 | 8/2008 |
| WO | 2010/047062 A1 | 4/2010 |

OTHER PUBLICATIONS

Bevan, M.J., "Helping the CD8+ T-Cell Response," Nat Rev Immunol., vol. 4(8):595-602 (Aug. 2004).
Boon, "Tumor Antigens Recognized by Cytolytic T Lymphocytes: Present Perspectives for Specific Immunotherapy," Int J Cancer, vol. 54(2), pp. 177-180 (May 8, 1993).
Boon, et al, "Human Tumor Antigens Recognized by T Lymphocytes," J Exp Med., vol. 183(3), pp. 725-729 (Mar. 1, 1996).
Bos, et al., "CD4+ T cell help in the tumor milieu is required for recruitment and cytolytic function of CD8+ T lymphocytes," Cancer Res., vol. 70(21), pp. 8368-8377 (Nov. 2010) Epub Oct. 12, 2010.
Butterfield, et al., "Generation of Human T-cell Responses to an HLA-A2.1-restricted Peptide Epitope Derived from α-Fetoprotein," Cancer Res., vol. 59(13), pp. 3134-3142 (Jul. 1, 1999).
Chamoto, et al., "Potentiation of Tumor Eradication by Adoptive Immunotherapy with T-Cell Receptor Gene-Transduced T-Helper Type 1 Cells," Cancer Res., vol. 64(1), pp. 386-390, (Jan. 2004).
Coulie, et al., "Cytolytic T-cell responses of cancer patients vaccinated with a MAGE antigen," Immunol Rev., vol. 188, pp. 33-42 (Oct. 2002).
Echard, et al., "Interaction of a Golgi-Associated Kinesin-Like Protein with Rab6," Science, vol. 279, pp. 580-585 (Jan. 1998).
Fujie, et al., "A MAGE-1-Encoded HLA-A24-Binding Synthetic Peptide induces Specific Anti-Tumor Cytotoxic T Lymphocytes," Int J Cancer, vol. 80(2), pp. 169-172 (Jan. 18, 1999).
Harris, "Structure and Function of the p53 Tumor Suppressor Gene: Clues for Rational Cancer Therapeutic Strategies," J Natl Cancer Inst., vol. 88(20), pp. 1442-1455 (Oct. 16, 1996).
Hirokawa, et al., "Kinesin and dynein superfamily proteins in organelle transport and cell division," Curr Opin Cell Biol., vol. 10, pp. 60-73 (Feb. 1998).

Imai, et al., "Identification of HLA-A2-restricted Ctl epitopes of a novel tumour-associated antigen, KIF20A, overexpressed in pancreatic cancer," Br J Cancer, vol. 102(2), pp. 300-307 (2011) Epub Dec. 21, 2010.
Kikuchi, et al., "Identification of a Sart-1-Derived Peptide Capable of Inducing HLA-A-A24-Restricted and Tumor-Specific Cytotoxic T Lymphocytes," Int J Cancer, vol. 81(3), pp. 459-466 (May 5, 1999).
Melief, et al., "Immunotherapy of established (pre)malignant disease by synthetic long peptide vaccines," Nat Rev Cancer, vol. 8(5), pp. 351-360 (May 2008).
Oiso, et al., "A Newly Identified MAGE-3-Derived Epitope Recognized by HLA-A24-Restricted Cytotoxic T Lymphocytes," Int J Cancer, vol. 81(3), pp. 387-394 (May 5, 1999).
Rosenberg, et al., "Cancer immunotherapy: moving beyond current vaccines," Nat Med., vol. 10(9), pp. 909-915 (Sep. 2004).
Shedlock, et al., "Requirement for CD4 T Cell Help in Generating Functional CD8 T Cell Memory," Science, vol. 300, pp. 337-339 (Apr. 2003).
Street, et al., "Perforin and interferon-(gamma) activities independently control tumor initiation, growth, and metastasis," Blood, vol. 97(1), pp. 192-197 (Jan. 2001).
Tanaka, et al., "Induction of Antitumor Cytotoxic T Lymphocytes with a MAGE-3-encoded Synthetic Peptide Presented by Human Leukocytes Antigen-A24," Cancer Res., vol. 57(20), pp. 4465-4468 (Oct. 15, 1997).
Taniuchi, et al., "Down-regulation of rAB6KIFL/KIF20A, a Kinesin Involved with Membrane Trafficking of Discs Large Homologue 5, Can Attenuate Growth of Pancreatic Cancer Cell," Cancer Res., vol. 65(1), pp. 105-112 (Jan. 2005).
Van Der Burg, et al., "Immunogenicity of Peptides Bound to MHC Class 1 Molecules Depends on the Mhc-Peptide Complex Stability," J Immunol., vol. 156(9), pp. 3308-3314 (May 1, 1996).
Vissers, et al., "The Renal Cell Carcinoma-associated Antigen G250 Encodes a Human Leukocyte Antigen (HLA)-A2.1-restricted Epitope Recognized by Cytotoxic T Lymphocytes," Cancer Res., vol. 59(21), pp. 5554-5559 (Nov. 1, 1999).
Wang, et al., "A Systematic Assessment of MHC Class II Peptide Binding Predictions and Evaluation of a Consensus Approach," PLoS Comput Biol., vol. 4(4), e1000048 (10 pages) (2008).
Imai, et al., "Identification of HLA-A2-restricted CTL epitopes of a novel tumour-associated antigen, KIF20A, overexpressed in pancreatic cancer," Br J Cancer, vol. 104(2), pp. 300-307 (2011) Epub Dec. 21, 2010.
Tomita, et al., "Indeitification of Promiscuous KIK20A Long Peptides bearing Both CD4+ and CD8+ T-Cell Epitopes: KIF20A-Specific CD4. T-Cell Immunity in Patients with Malignant Tumor," *Clin Cancer Res* 2013; 19:4508-4520.

* cited by examiner

1. KIF20A (60-84): DSMEKVKVYLRVRPLLPSELERQED     (SEQ ID NO: 1)
   HLA-A24
2. KIF20A (809-833): CIAEQYHTVLKLQGQVSAKKRLGTN     (SEQ ID NO: 2)
   HLA-A2
3. KIF20A (494-517): TLHVAKFSAIASQLVHAPPMQLGF     (SEQ ID NO: 3)

4. KIF20A (843-863): PPGKKPFLRNLLPRTPTCQSS     (SEQ ID NO: 4)

Fig. 2A1
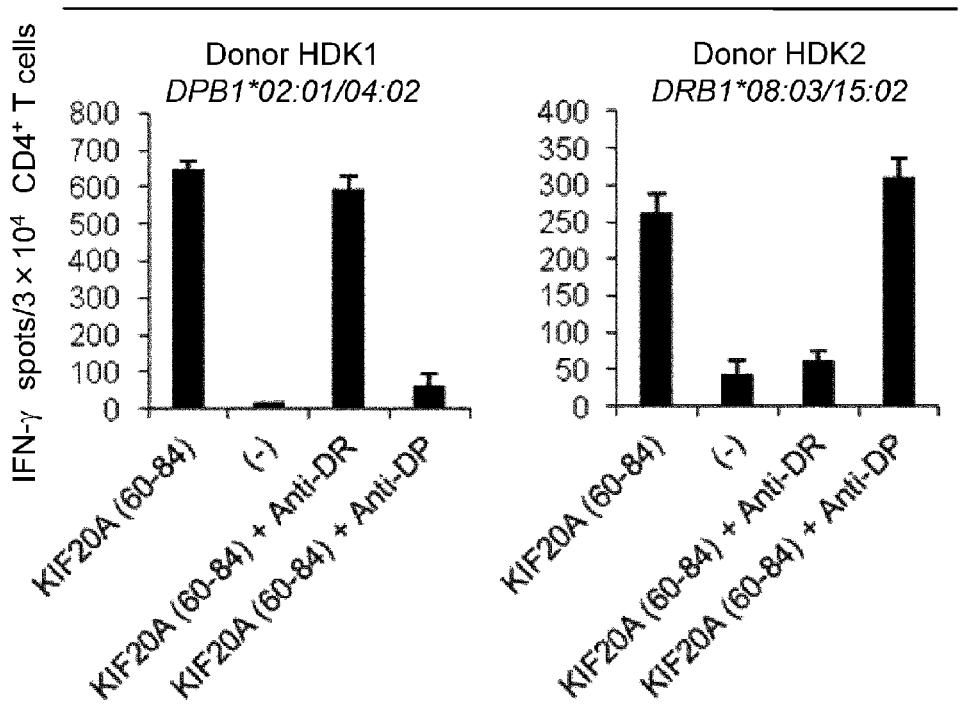
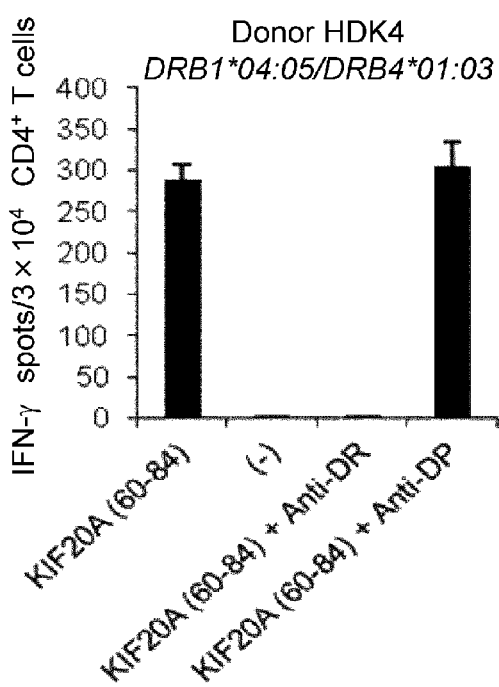

Fig. 2A2
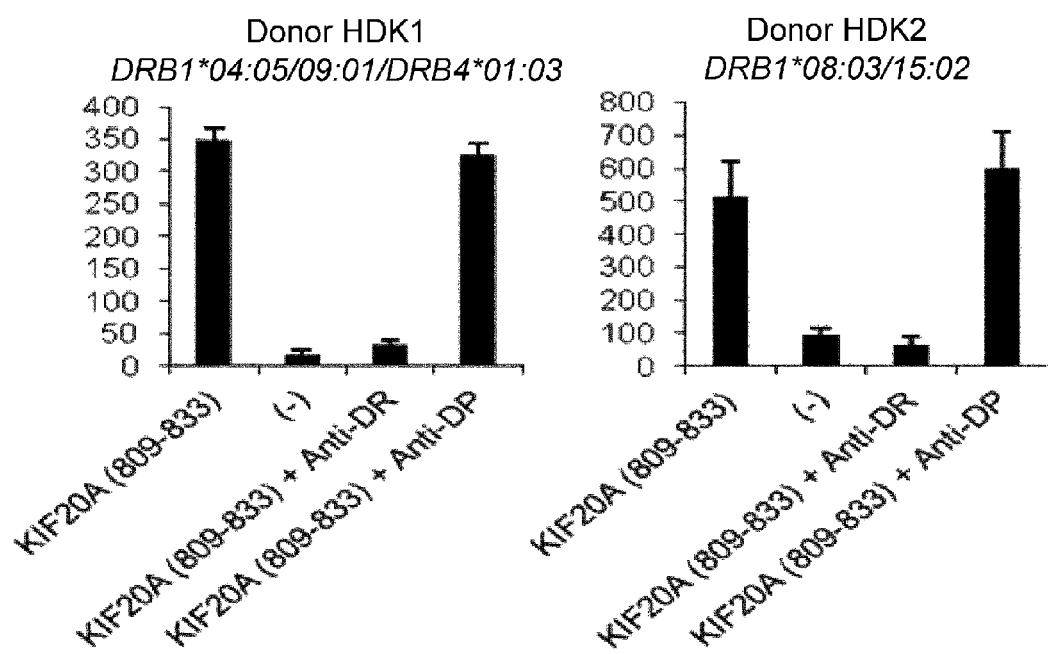
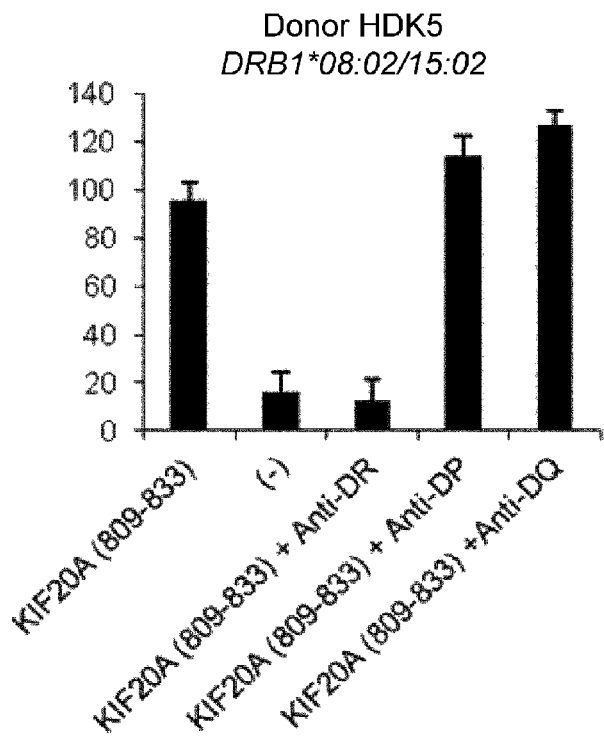

Fig. 2B
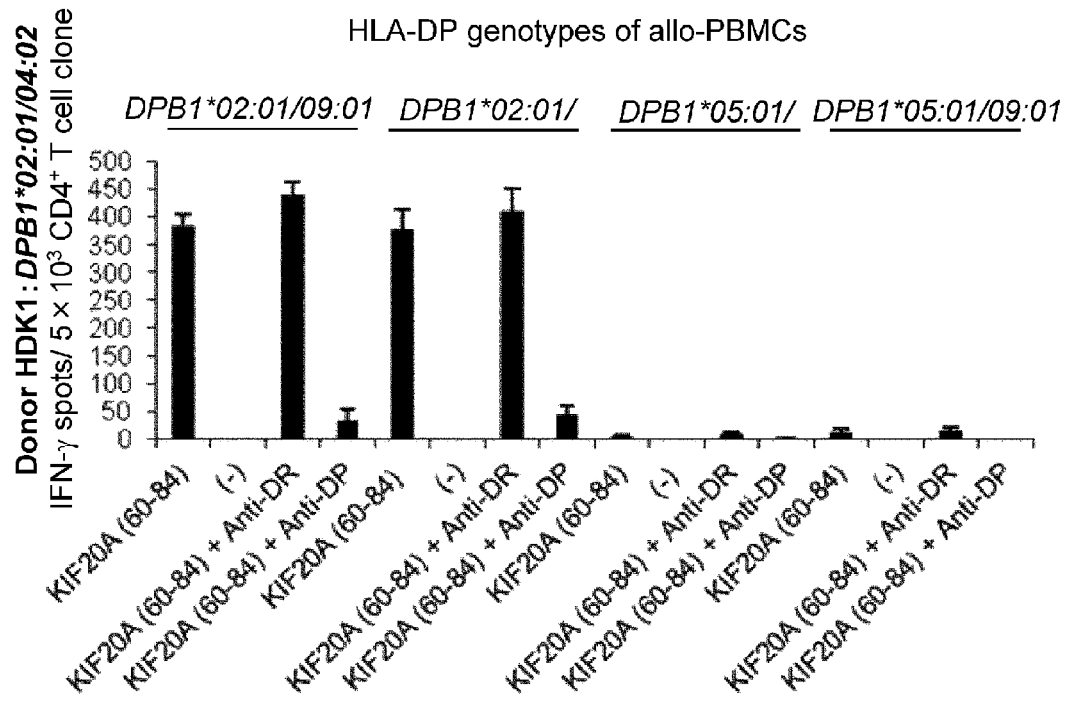
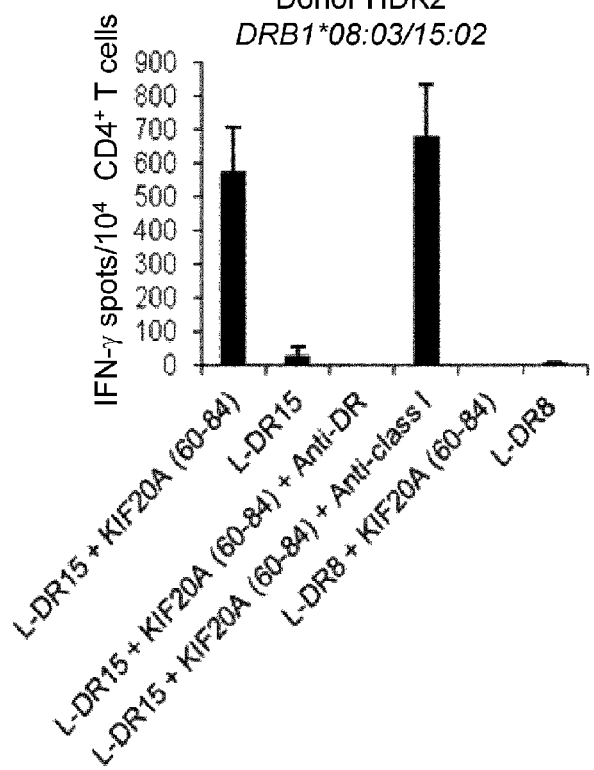

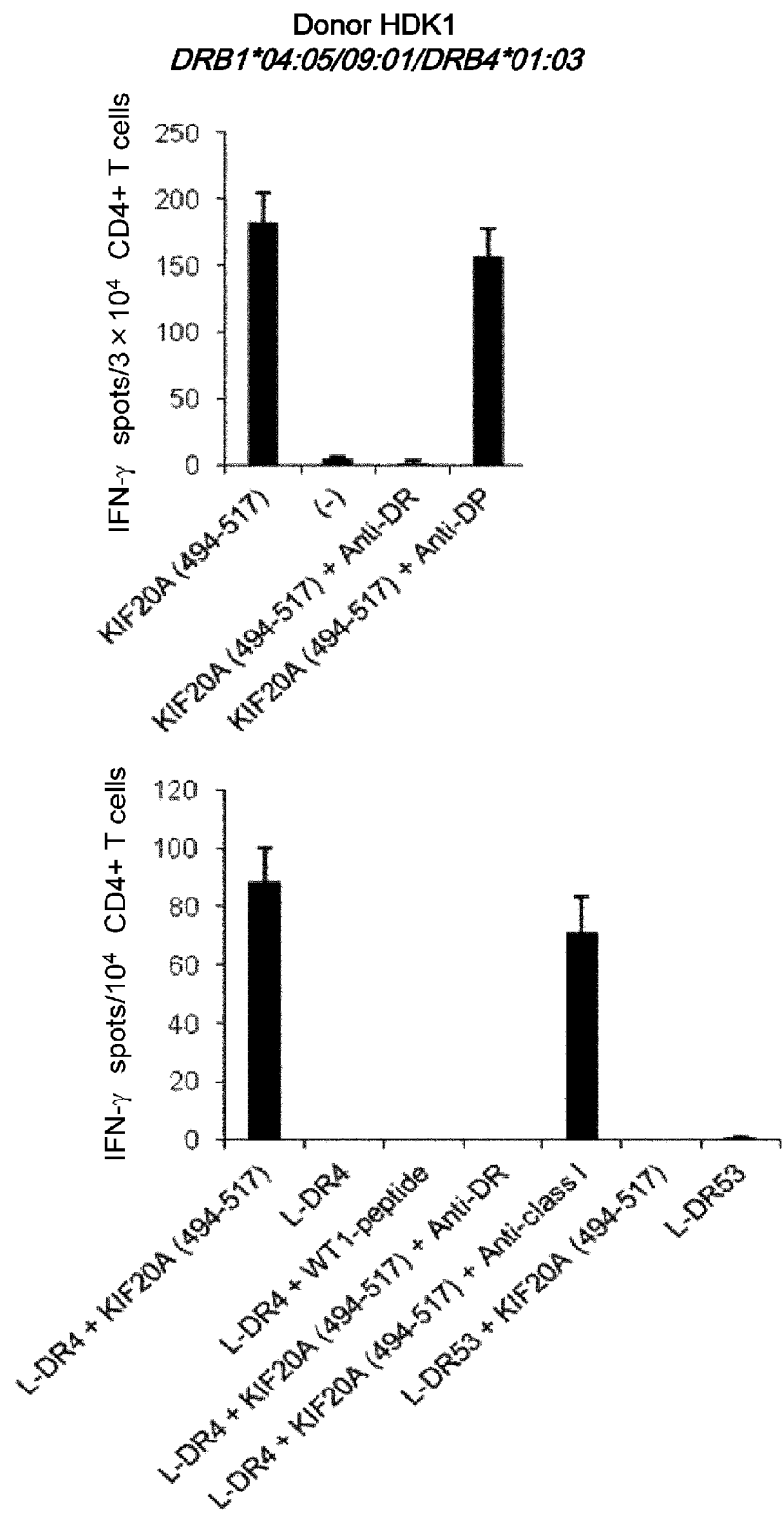

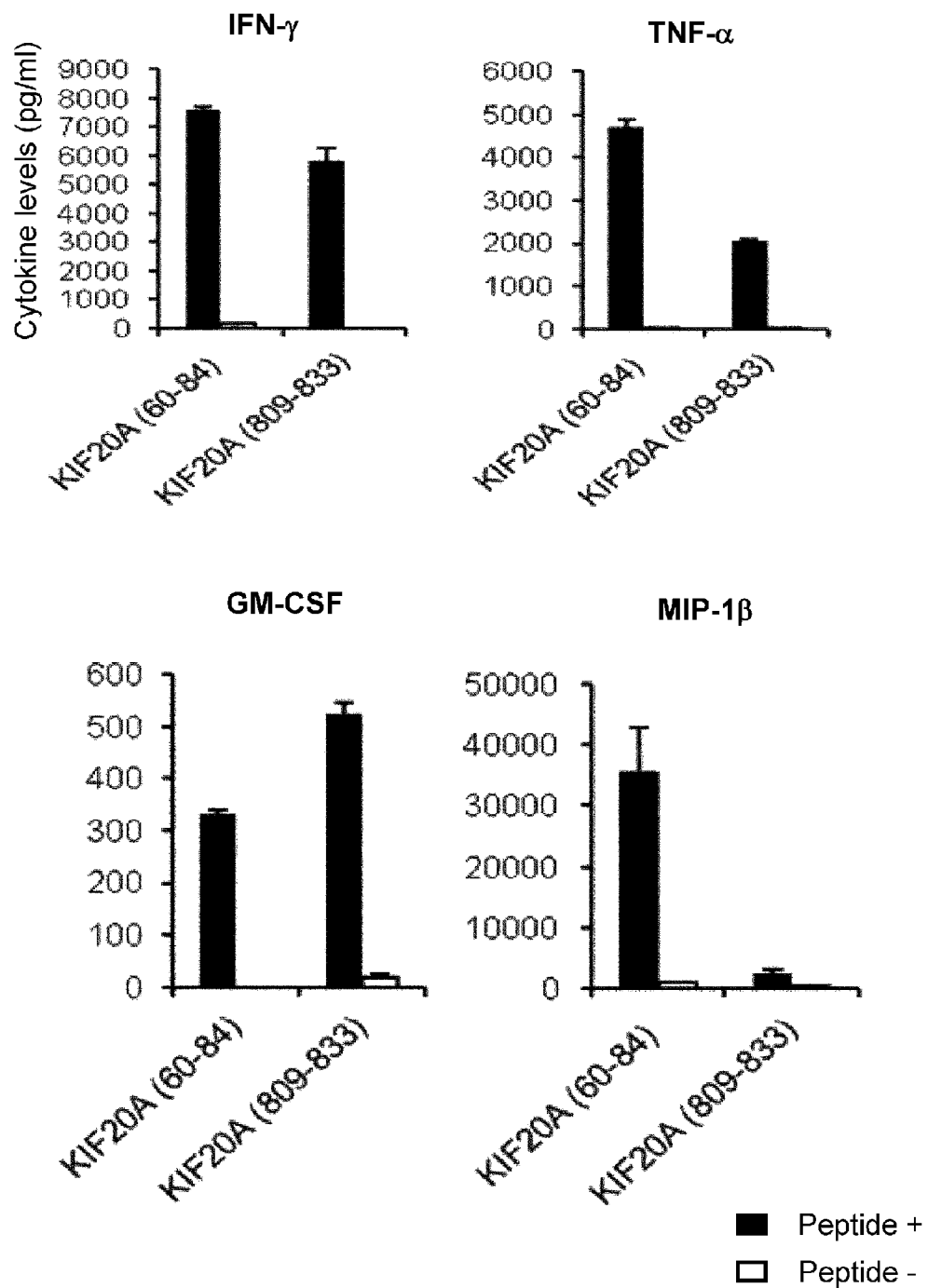
Fig. 3A1

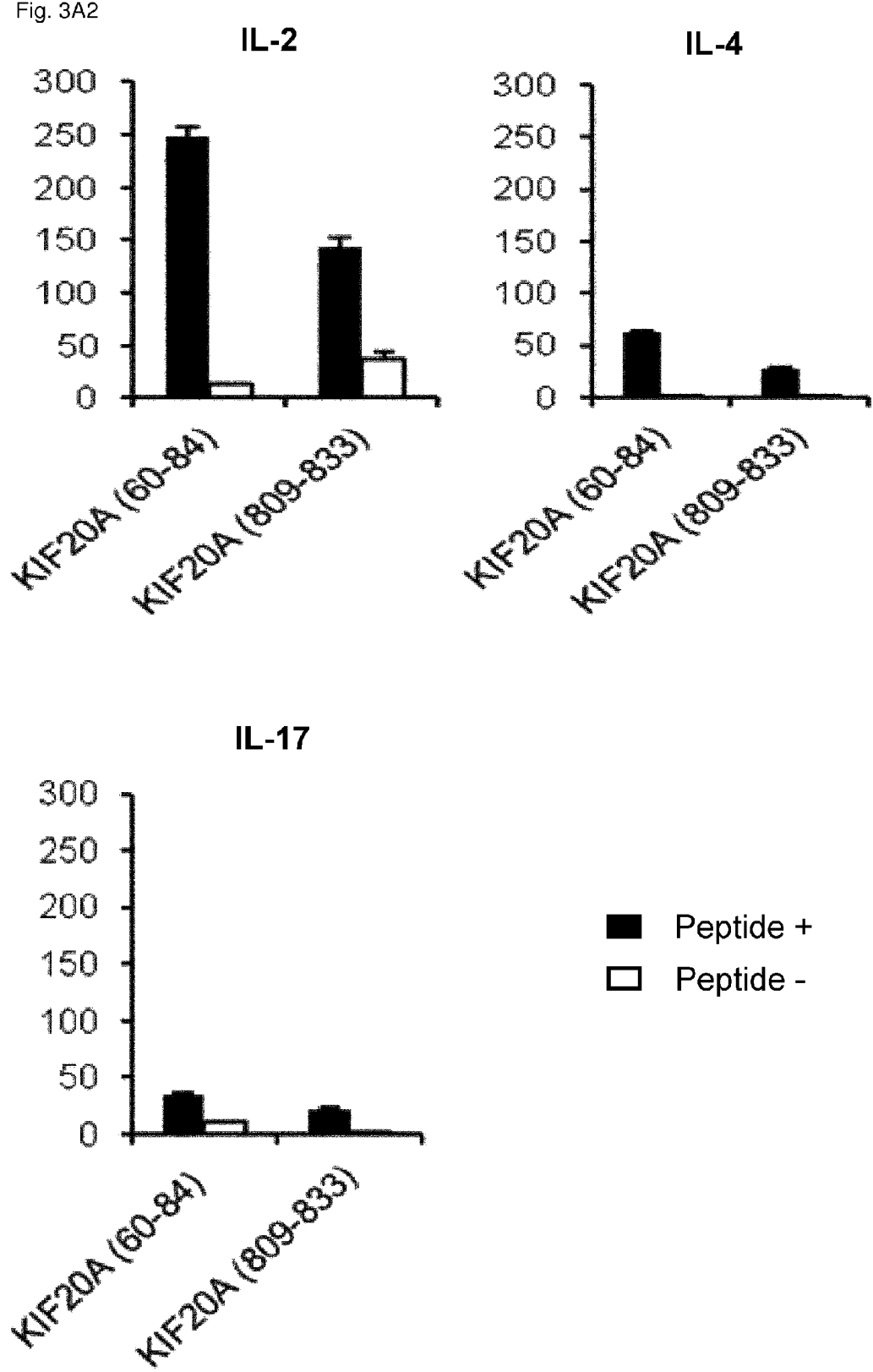

Fig. 4A-B
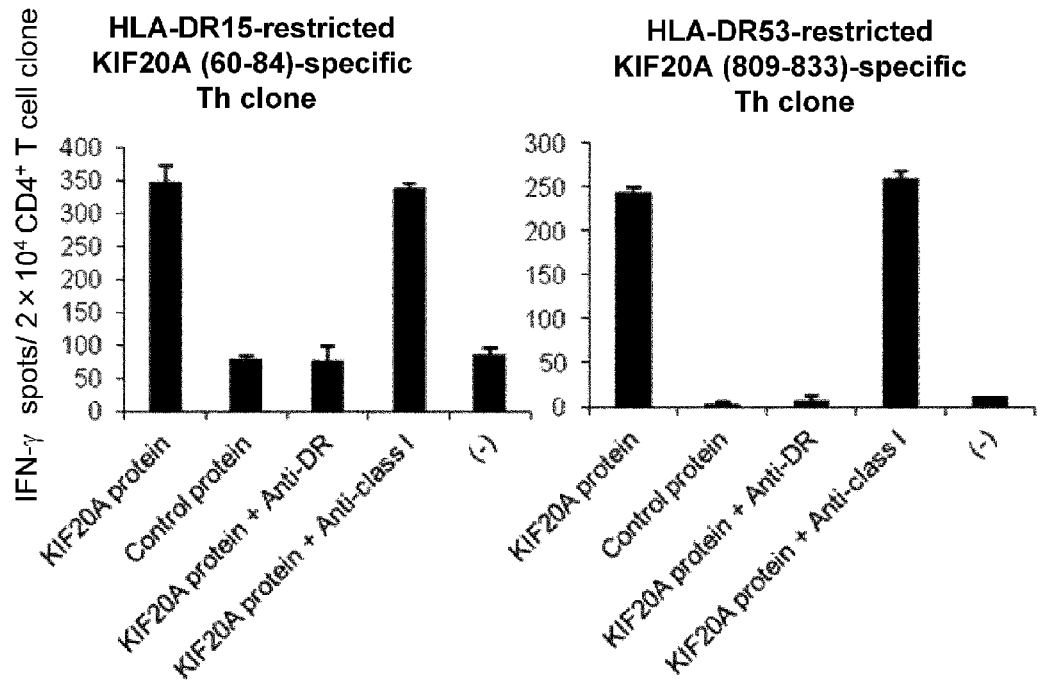
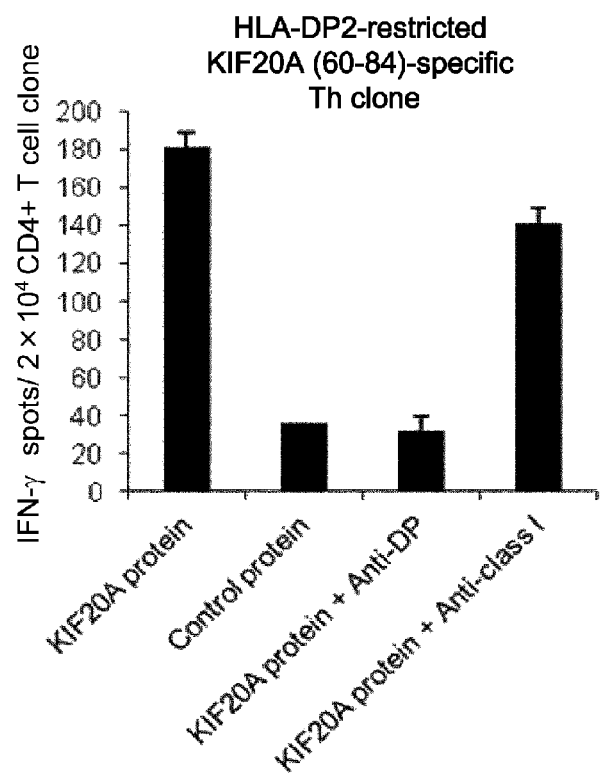

Fig. 5B-C
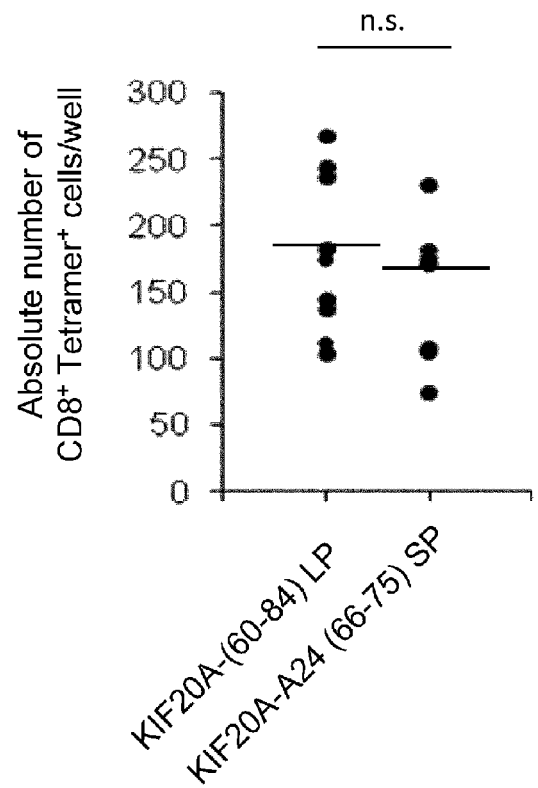
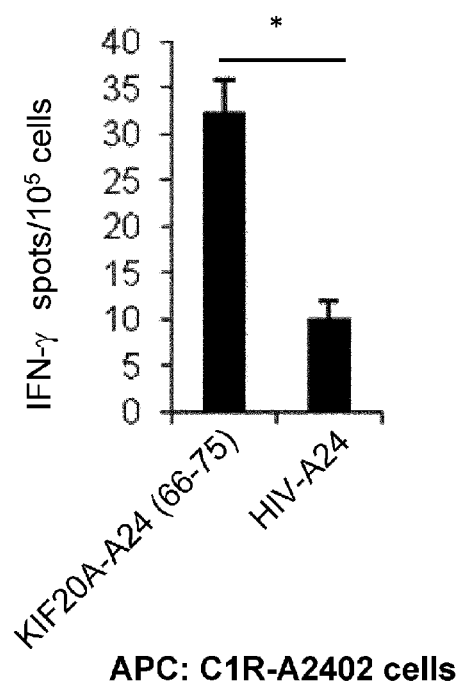
APC: C1R-A2402 cells

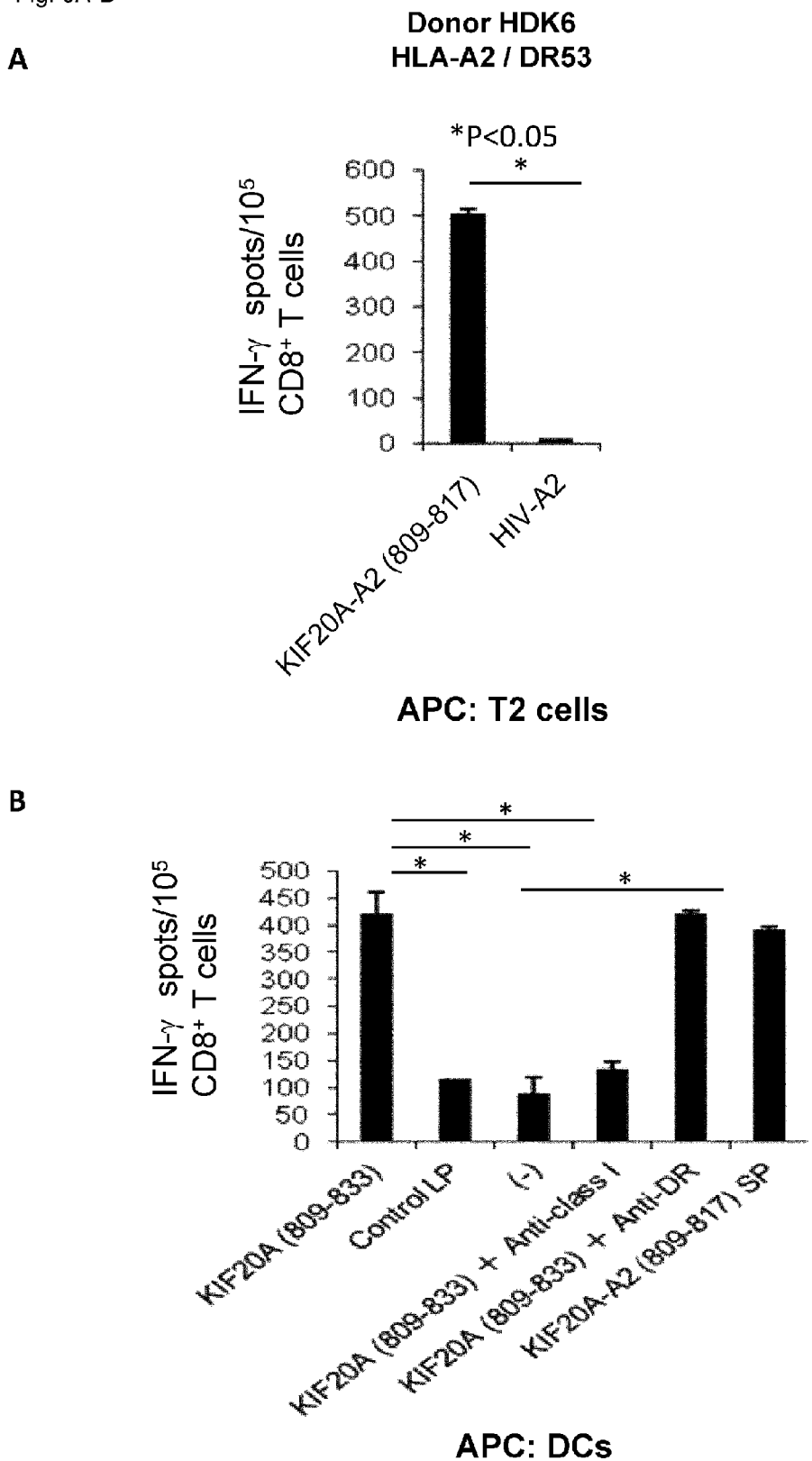
Fig. 6A-B

Fig. 7C-D
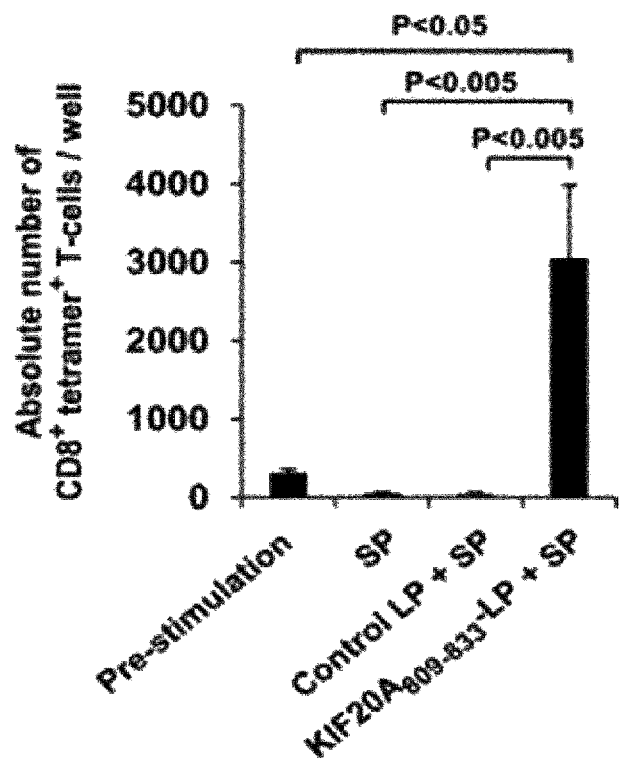
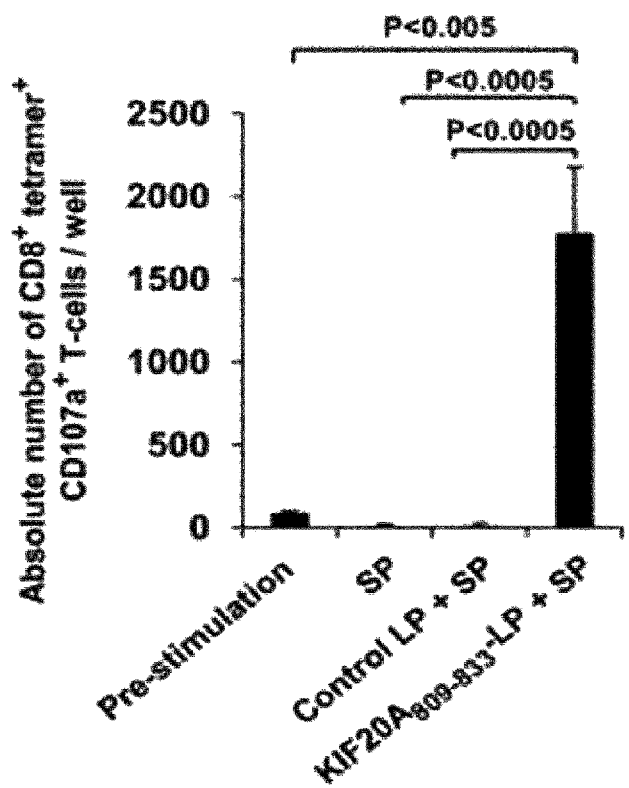

A

Fig. 8B
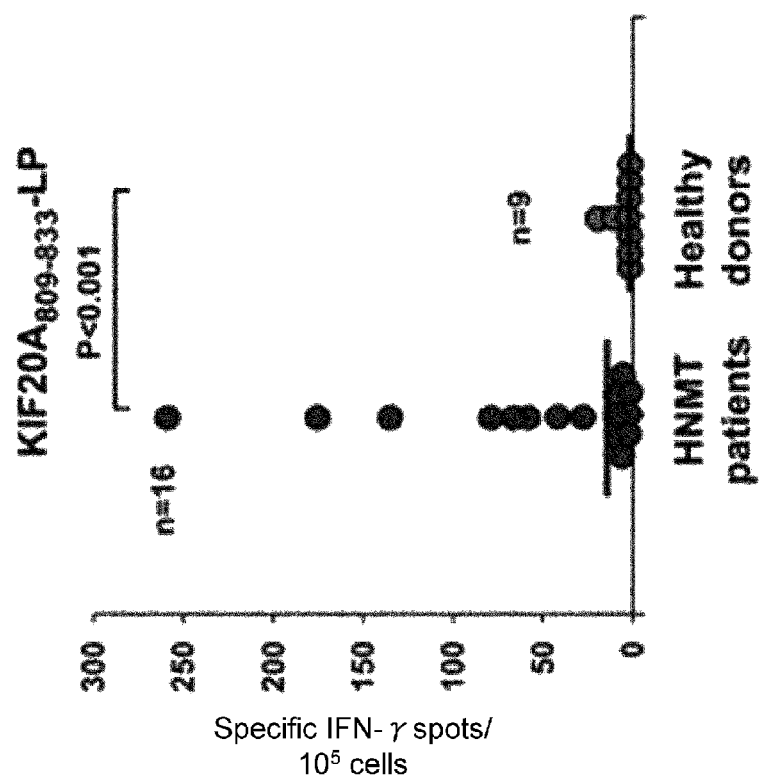
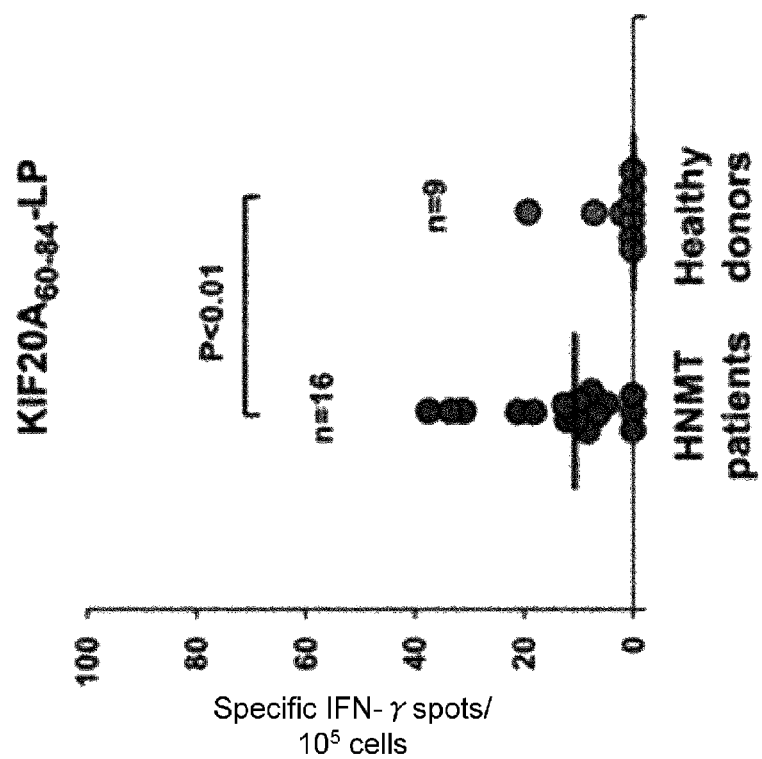

Fig. 8C-D
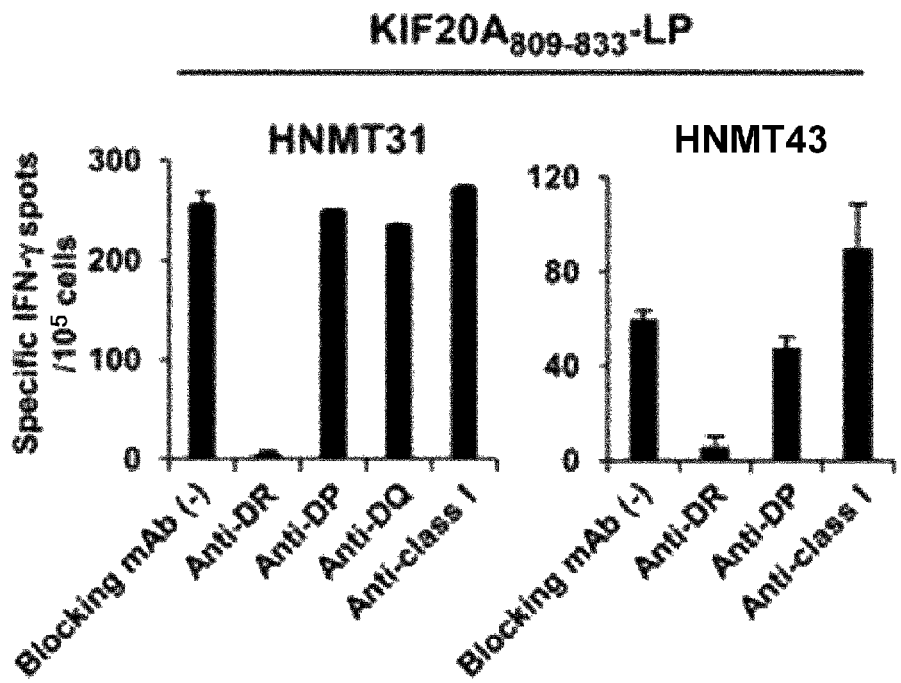
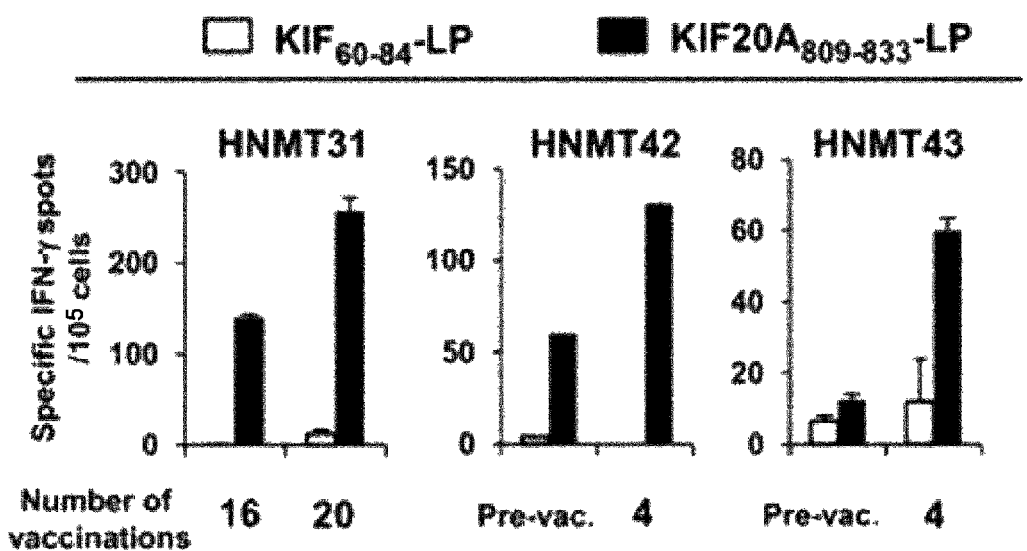

Fig. 8F

Clinical characteristics of HNMT patients

| Patient ID | Age/Sex | KIF20A-specific CD4+ T-cell responses[a] | | Histologic subtype | IHC analysis of KIF20A Staining | HLA-DRB1 | HLA-DRB4 | HLA-DPB1 |
|---|---|---|---|---|---|---|---|---|
| | | KIF20A$_{66-84}$-LP | KIF20A$_{809-833}$-LP | | | | | |
| CTR-8379 | | Positive / Total | | | | | | |
| | | 2/16 (13%) | 7/16 (44%) | | | | | |
| HNMT10 | 61/M | - | - | Squamous Cell Carcinoma | n.t. | 01:01 / 04:05 | DR53 | 05:01 / - |
| HNMT20 | 57/F | - | + | Squamous Cell Carcinoma | n.t. | 01:01 / 09:01 | DR53 | 02:01 / 05:01 |
| HNMT26 | 70/M | - | - | Basaloid Squamous Cell Carcinoma | n.t. | 04:05 / 15:02 | DR53 | 05:01 / 09:01 |
| HNMT29 | 64/F | - | + | Squamous Cell Carcinoma | n.t. | 09:01 / 14:54 | DR53 | 03:01 / 05:01 |
| HNMT31 | 69/F | - | + | Adenoid Cystic Carcinoma | Positive | 01:01 / 11:01 | - | 02:01 / 04:02 |
| HNMT34 | 65/M | - | + | Squamous Cell Carcinoma | n.t. | 08:03 / 15:02 | - | 02:01 / 05:01 |
| HNMT35 | 85/F | - | + | Squamous Cell Carcinoma | n.t. | 04:05 / 08:02 | DR53 | 05:01 / - |
| HNMT39 | 77/M | - | - | Adenoid Cystic Carcinoma | n.t. | 04:06 / 14:54 | DR53 | 05:01 / 19:01 |
| HNMT40 | 76/M | - | + | Squamous Cell Carcinoma | n.t. | 01:01 / 09:01 | DR53 | 04:02 / 05:01 |
| HNMT41 | 51/F | + | + | Adenoid Cystic Carcinoma | n.t. | 01:01 / 04:05 | DR53 | 04:02 / 05:01 |
| HNMT42 | 36/F | - | + | Unknown | n.t. | 01:01 / 08:02 | - | 04:02 / 05:01 |
| HNMT43 | 50/M | - | + | Squamous Cell Carcinoma | n.t. | 08:02 / 09:01 | DR53 | 05:01 / - |
| CTR-8380 | | | | | | | | |
| HNMT102 | 80/F | - | - | Squamous Cell Carcinoma | Negative | 15:02 / - | - | 02:01 / 09:01 |
| HNMT105 | 65/M | - | - | Angiosarcoma | Negative | 04:05 / 13:02 | DR53 | 03:01 / 04:01 |
| HNMT107 | 20/M | - | - | Osteosarcoma | Negative | 09:01 / - | DR53 | 02:01 / 02:02 |
| HNMT108 | 41/M | + | - | Osteosarcoma | Positive | 04:05 / 09:01 | DR53 | 05:01 / - |

SEQUENCE LISTING

<160> NUMBER OF SEQ ID NOS: 11

<210> SEQ ID NO 1
<211> LENGTH: 25
<212> TYPE: PRT
<213> ORGANISM: Artificial Sequence
<220> FEATURE:
<223> OTHER INFORMATION: An artificially synthesized peptide

<400> SEQUENCE: 1

Asp Ser Met Glu Lys Val Lys Val Tyr Leu Arg Val Arg Pro Leu Leu
1               5                   10                  15

Pro Ser Glu Leu Glu Arg Gln Glu Asp
            20                  25

<210> SEQ ID NO 2
<211> LENGTH: 25
<212> TYPE: PRT
<213> ORGANISM: Artificial Sequence
<220> FEATURE:
<223> OTHER INFORMATION: An artificially synthesized peptide

<400> SEQUENCE: 2

Cys Ile Ala Glu Gln Tyr His Thr Val Leu Lys Leu Gln Gly Gln Val
1               5                   10                  15

Ser Ala Lys Lys Arg Leu Gly Thr Asn
            20                  25

<210> SEQ ID NO 3
<211> LENGTH: 24
<212> TYPE: PRT
<213> ORGANISM: Artificial Sequence
<220> FEATURE:
<223> OTHER INFORMATION: An artificially synthesized peptide

<400> SEQUENCE: 3

Thr Leu His Val Ala Lys Phe Ser Ala Ile Ala Ser Gln Leu Val His
1               5                   10                  15

Ala Pro Pro Met Gln Leu Gly Phe
            20

<210> SEQ ID NO 4
<211> LENGTH: 21
<212> TYPE: PRT
<213> ORGANISM: Artificial Sequence
<220> FEATURE:
<223> OTHER INFORMATION: An artificially synthesized peptide

<400> SEQUENCE: 4

Pro Pro Gly Lys Lys Pro Phe Leu Arg Asn Leu Leu Pro Arg Thr Pro
1               5                   10                  15

Thr Cys Gln Ser Ser
            20

<210> SEQ ID NO 5
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 5

Cys Ile Ala Glu Gln Tyr His Thr Val
1               5

```
<210> SEQ ID NO 6
<211> LENGTH: 10
<212> TYPE: PRT
<213> ORGANISM: Artificial Sequence
<220> FEATURE:
<223> OTHER INFORMATION: An artificially synthesized peptide

<400> SEQUENCE: 6

Lys Val Tyr Leu Arg Val Arg Pro Leu Leu
1               5                   10

<210> SEQ ID NO 7
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 7

Arg Tyr Leu Arg Asp Gln Gln Leu Leu
1               5

<210> SEQ ID NO 8
<211> LENGTH: 9
<212> TYPE: PRT
<213> ORGANISM: Artificial Sequence
<220> FEATURE:
<223> OTHER INFORMATION: An artificially synthesized peptide

<400> SEQUENCE: 8

Ser Leu Tyr Asn Thr Tyr Ala Thr Leu
1               5

<210> SEQ ID NO 9
<211> LENGTH: 16
<212> TYPE: PRT
<213> ORGANISM: Artificial Sequence
<220> FEATURE:
<223> OTHER INFORMATION: An artificially synthesized peptide

<400> SEQUENCE: 9

Lys Arg Tyr Phe Lys Leu Ser His Leu Gln Met His Ser Arg Lys His
1               5                   10                  15

<210> SEQ ID NO 10
<211> LENGTH: 3471
<212> TYPE: DNA
<213> ORGANISM: Homo sapiens
<220> FEATURE:
<221> NAME/KEY: CDS
<222> LOCATION: (497)..(3169)

<400> SEQUENCE: 10
tttttcccct taagacaaag caagcaccct aaaccagtta ccctgtgcac tcctgttaag      60
attgttgcta aggaaggaca ggagttggct gctgaagcct caagatttcc tttaggctct     120
taggtaagaa atgtctaagg ttcaaggaaa aaggttaagt tggaagaatc ccaggcaaaa     180
taagtgcgaa tccacgacag ttggtaaccc ggacccacat tagaactcag aggtcaagca     240
gaagcgaacg actggaattc cagtcaggcc cgccccttt ccttacgcgg attggtagct      300
gcaggcttcc ctatctgatt ggccgaacga acgcagcgcg taatttaaaa tattgtatct     360
gtaacaaagc tgcacctcgt gggcggagtt gtgctctgcg gctgcgaaag tccagcttcg     420
gcgactaggt gtgagtaagc cagtatccca ggaggagcaa gtggcacgtc ttcggaccta     480
```

-continued

```
ggctgcccct gccgtc atg tcg caa ggg atc ctt tct ccg cca gcg ggc ttg       532
               Met Ser Gln Gly Ile Leu Ser Pro Pro Ala Gly Leu
                 1               5                  10 ctg tcc gat gac gat gtc gta gtt tct ccc atg ttt gag tcc aca gct         580
Leu Ser Asp Asp Asp Val Val Val Ser Pro Met Phe Glu Ser Thr Ala
         15              20              25 gca gat ttg ggg tct gtg gta cgc aag aac ctg cta tca gac tgc tct         628
Ala Asp Leu Gly Ser Val Val Arg Lys Asn Leu Leu Ser Asp Cys Ser
     30              35              40 gtc gtc tct acc tcc cta gag gac aag cag cag gtt cca tct gag gac         676
Val Val Ser Thr Ser Leu Glu Asp Lys Gln Gln Val Pro Ser Glu Asp
45              50              55              60 agt atg gag aag gtg aaa gta tac ttg agg gtt agg ccc tta cct             724
Ser Met Glu Lys Val Lys Val Tyr Leu Arg Val Arg Pro Leu Leu Pro
                 65              70              75 tca gag ttg gaa cga cag gaa gat cag ggt tgt gtc cgt att gag aat         772
Ser Glu Leu Glu Arg Gln Glu Asp Gln Gly Cys Val Arg Ile Glu Asn
             80              85              90 gtg gag acc ctt gtt cta caa gca ccc aag gac tct ttt gcc ctg aag         820
Val Glu Thr Leu Val Leu Gln Ala Pro Lys Asp Ser Phe Ala Leu Lys
         95              100             105 agc aat gaa cgg gga att ggc caa gca aca cac agg ttc acc ttt tcc         868
Ser Asn Glu Arg Gly Ile Gly Gln Ala Thr His Arg Phe Thr Phe Ser
110             115             120 cag atc ttt ggg cca gaa gtg gga cag gca tcc ttc ttc aac cta act         916
Gln Ile Phe Gly Pro Glu Val Gly Gln Ala Ser Phe Phe Asn Leu Thr
125             130             135             140 gtg aag gag atg gta aag gat gta ctc aaa ggg cag aac tgg ctc atc         964
Val Lys Glu Met Val Lys Asp Val Leu Lys Gly Gln Asn Trp Leu Ile
                 145             150             155 tat aca tat gga gtc act aac tca ggg aaa acc cac acg att caa ggt         1012
Tyr Thr Tyr Gly Val Thr Asn Ser Gly Lys Thr His Thr Ile Gln Gly
             160             165             170 acc atc aag gat gga ggg att ctc ccc cgg tcc ctg gcg ctg atc ttc         1060
Thr Ile Lys Asp Gly Gly Ile Leu Pro Arg Ser Leu Ala Leu Ile Phe
         175             180             185 aat agc ctc caa ggc caa ctt cat cca aca cct gat ctg aag ccc ttg         1108
Asn Ser Leu Gln Gly Gln Leu His Pro Thr Pro Asp Leu Lys Pro Leu
190             195             200 ctc tcc aat gag gta atc tgg cta gac agc aag cag atc cga cag gag         1156
Leu Ser Asn Glu Val Ile Trp Leu Asp Ser Lys Gln Ile Arg Gln Glu
205             210             215             220 gaa atg aag aag ctg tcc ctg cta aat gga ggc ctc caa gag gag gag         1204
Glu Met Lys Lys Leu Ser Leu Leu Asn Gly Gly Leu Gln Glu Glu Glu
                 225             230             235 ctg tcc act tcc ttg aag agg agt gtc tac atc gaa agt cgg ata ggt         1252
Leu Ser Thr Ser Leu Lys Arg Ser Val Tyr Ile Glu Ser Arg Ile Gly
             240             245             250 acc agc acc agc ttc gac agt ggc att gct ggg ctc tct tct atc agt        1300
Thr Ser Thr Ser Phe Asp Ser Gly Ile Ala Gly Leu Ser Ser Ile Ser
         255             260             265 cag tgt acc agc agt agc cag ctg gat gaa aca agt cat cga tgg gca         1348
Gln Cys Thr Ser Ser Ser Gln Leu Asp Glu Thr Ser His Arg Trp Ala
270             275             280 cag cca gac act gcc cca cta cct gtc ccg gca aac att cgc ttc tcc         1396
Gln Pro Asp Thr Ala Pro Leu Pro Val Pro Ala Asn Ile Arg Phe Ser
285             290             295             300 atc tgg atc tca ttc ttt gag atc tac aac gaa ctg ctt tat gac cta         1444
Ile Trp Ile Ser Phe Phe Glu Ile Tyr Asn Glu Leu Leu Tyr Asp Leu
                 305             310             315
```

| | |
|---|---|
| tta gaa ccg cct agc caa cag cgc aag agg cag act ttg cgg cta tgc<br>Leu Glu Pro Pro Ser Gln Gln Arg Lys Arg Gln Thr Leu Arg Leu Cys<br>320                           325                      330 | 1492 |
| gag gat caa aat ggc aat ccc tat gtg aaa gat ctc aac tgg att cat<br>Glu Asp Gln Asn Gly Asn Pro Tyr Val Lys Asp Leu Asn Trp Ile His<br>        335                       340                       345 | 1540 |
| gtg caa gat gct gag gag gcc tgg aag ctc cta aaa gtg ggt cgt aag<br>Val Gln Asp Ala Glu Glu Ala Trp Lys Leu Leu Lys Val Gly Arg Lys<br>350                         355                      360 | 1588 |
| aac cag agc ttt gcc agc acc cac ctc aac cag aac tcc agc cgc agt<br>Asn Gln Ser Phe Ala Ser Thr His Leu Asn Gln Asn Ser Ser Arg Ser<br>365                       370                       375                 380 | 1636 |
| cac agc atc ttc tca atc agg atc cta cac ctt cag ggg gaa gga gat<br>His Ser Ile Phe Ser Ile Arg Ile Leu His Leu Gln Gly Glu Gly Asp<br>                 385                       390                       395 | 1684 |
| ata gtc ccc aag atc agc gag ctg tca ctc tgt gat ctg gct ggc tca<br>Ile Val Pro Lys Ile Ser Glu Leu Ser Leu Cys Asp Leu Ala Gly Ser<br>400                         405                      410 | 1732 |
| gag cgc tgc aaa gat cag aag agt ggt gaa cgg ttg aag gaa gca gga<br>Glu Arg Cys Lys Asp Gln Lys Ser Gly Glu Arg Leu Lys Glu Ala Gly<br>                 415                       420                       425 | 1780 |
| aac att aac acc tct cta cac acc ctg ggc cgc tgt att gct gcc ctt<br>Asn Ile Asn Thr Ser Leu His Thr Leu Gly Arg Cys Ile Ala Ala Leu<br>430                         435                      440 | 1828 |
| cgt caa aac cag cag aac cgg tca aag cag aac ctg gtt ccc ttc cgt<br>Arg Gln Asn Gln Gln Asn Arg Ser Lys Gln Asn Leu Val Pro Phe Arg<br>445                       450                       455                 460 | 1876 |
| gac agc aag ttg act cga gtg ttc caa ggt ttc ttc aca ggc cga ggc<br>Asp Ser Lys Leu Thr Arg Val Phe Gln Gly Phe Phe Thr Gly Arg Gly<br>                 465                       470                       475 | 1924 |
| cgt tcc tgc atg att gtc aat gtg aat ccc tgt gca tct acc tat gat<br>Arg Ser Cys Met Ile Val Asn Val Asn Pro Cys Ala Ser Thr Tyr Asp<br>                       480                       485                       490 | 1972 |
| gaa act ctt cat gtg gcc aag ttc tca gcc att gct agc cag ctt gtg<br>Glu Thr Leu His Val Ala Lys Phe Ser Ala Ile Ala Ser Gln Leu Val<br>                 495                       500                       505 | 2020 |
| cat gcc cca cct atg caa ctg gga ttc cca tcc ctg cac tcg ttc atc<br>His Ala Pro Pro Met Gln Leu Gly Phe Pro Ser Leu His Ser Phe Ile<br>510                         515                      520 | 2068 |
| aag gaa cat agt ctt cag gta tcc ccc agc tta gag aaa ggg gct aag<br>Lys Glu His Ser Leu Gln Val Ser Pro Ser Leu Glu Lys Gly Ala Lys<br>525                       530                      535                 540 | 2116 |
| gca gac aca ggc ctt gat gat gat att gaa aat gaa gct gac atc tcc<br>Ala Asp Thr Gly Leu Asp Asp Asp Ile Glu Asn Glu Ala Asp Ile Ser<br>                 545                       550                       555 | 2164 |
| atg tat ggc aaa gag gag ctc cta caa gtt gtg gaa gcc atg aag aca<br>Met Tyr Gly Lys Glu Glu Leu Leu Gln Val Val Glu Ala Met Lys Thr<br>560                         565                      570 | 2212 |
| ctg ctt ttg aag gaa cga cag gaa aag cta cag ctg gag atg cat ctc<br>Leu Leu Leu Lys Glu Arg Gln Glu Lys Leu Gln Leu Glu Met His Leu<br>                 575                       580                       585 | 2260 |
| cga gat gaa att tgc aat gag atg gta gaa cag atg caa cag cgg gaa<br>Arg Asp Glu Ile Cys Asn Glu Met Val Glu Gln Met Gln Gln Arg Glu<br>590                         595                      600 | 2308 |
| cag tgg tgc agt gaa cat ttg gac acc caa aag gaa cta ttg gag gaa<br>Gln Trp Cys Ser Glu His Leu Asp Thr Gln Lys Glu Leu Leu Glu Glu<br>605                       610                      615                 620 | 2356 |
| atg tat gaa gaa aaa cta aat atc ctc aag gag tca ctg aca agt ttt<br>Met Tyr Glu Glu Lys Leu Asn Ile Leu Lys Glu Ser Leu Thr Ser Phe | 2404 |

-continued

|     |     |     |     |     | 625 |     |     |     | 630 |     |     |     |     | 635 |     |      |
|-----|-----|-----|-----|-----|-----|-----|-----|-----|-----|-----|-----|-----|-----|-----|-----|------|
| tac | caa | gaa | gag | att | cag | gag | cgg | gat | gaa | aag | att | gaa | gag | cta | gaa | 2452 |
| Tyr | Gln | Glu | Glu | Ile | Gln | Glu | Arg | Asp | Glu | Lys | Ile | Glu | Glu | Leu | Glu |      |
|     |     |     | 640 |     |     |     |     | 645 |     |     |     |     | 650 |     |     |      |

| gct | ctc | ttg | cag | gaa | gcc | aga | caa | cag | tca | gtg | gcc | cat | cag | caa | tca | 2500 |
|-----|-----|-----|-----|-----|-----|-----|-----|-----|-----|-----|-----|-----|-----|-----|-----|------|
| Ala | Leu | Leu | Gln | Glu | Ala | Arg | Gln | Gln | Ser | Val | Ala | His | Gln | Gln | Ser |      |
|     |     |     |     | 655 |     |     |     |     | 660 |     |     |     |     | 665 |     |      |

| ggg | tct | gaa | ttg | gcc | cta | cgg | cgg | tca | caa | agg | ttg | gca | gct | tct | gcc | 2548 |
|-----|-----|-----|-----|-----|-----|-----|-----|-----|-----|-----|-----|-----|-----|-----|-----|------|
| Gly | Ser | Glu | Leu | Ala | Leu | Arg | Arg | Ser | Gln | Arg | Leu | Ala | Ala | Ser | Ala |      |
|     |     | 670 |     |     |     |     | 675 |     |     |     |     | 680 |     |     |     |      |

| tcc | acc | cag | cag | ctt | cag | gag | gtt | aaa | gct | aaa | tta | cag | cag | tgc | aaa | 2596 |
|-----|-----|-----|-----|-----|-----|-----|-----|-----|-----|-----|-----|-----|-----|-----|-----|------|
| Ser | Thr | Gln | Gln | Leu | Gln | Glu | Val | Lys | Ala | Lys | Leu | Gln | Gln | Cys | Lys |      |
| 685 |     |     |     |     | 690 |     |     |     |     | 695 |     |     |     |     | 700 |      |

| gca | gag | cta | aac | tct | acc | act | gaa | gag | ttg | cat | aag | tat | cag | aaa | atg | 2644 |
|-----|-----|-----|-----|-----|-----|-----|-----|-----|-----|-----|-----|-----|-----|-----|-----|------|
| Ala | Glu | Leu | Asn | Ser | Thr | Thr | Glu | Glu | Leu | His | Lys | Tyr | Gln | Lys | Met |      |
|     |     |     |     | 705 |     |     |     |     | 710 |     |     |     |     | 715 |     |      |

| tta | gaa | cca | cca | ccc | tca | gcc | aag | ccc | ttc | acc | att | gat | gtg | gac | aag | 2692 |
|-----|-----|-----|-----|-----|-----|-----|-----|-----|-----|-----|-----|-----|-----|-----|-----|------|
| Leu | Glu | Pro | Pro | Pro | Ser | Ala | Lys | Pro | Phe | Thr | Ile | Asp | Val | Asp | Lys |      |
|     |     |     | 720 |     |     |     |     | 725 |     |     |     |     | 730 |     |     |      |

| aag | tta | gaa | gag | ggc | cag | aag | aat | ata | agg | ctg | ttg | cgg | aca | gag | ctt | 2740 |
|-----|-----|-----|-----|-----|-----|-----|-----|-----|-----|-----|-----|-----|-----|-----|-----|------|
| Lys | Leu | Glu | Glu | Gly | Gln | Lys | Asn | Ile | Arg | Leu | Leu | Arg | Thr | Glu | Leu |      |
|     |     |     | 735 |     |     |     |     | 740 |     |     |     |     | 745 |     |     |      |

| cag | aaa | ctt | ggt | gag | tct | ctc | caa | tca | gca | gag | aga | gct | tgt | tgc | cac | 2788 |
|-----|-----|-----|-----|-----|-----|-----|-----|-----|-----|-----|-----|-----|-----|-----|-----|------|
| Gln | Lys | Leu | Gly | Glu | Ser | Leu | Gln | Ser | Ala | Glu | Arg | Ala | Cys | Cys | His |      |
|     | 750 |     |     |     |     | 755 |     |     |     |     | 760 |     |     |     |     |      |

| agc | act | ggg | gca | gga | aaa | ctt | cgt | caa | gcc | ttg | acc | act | tgt | gat | gac | 2836 |
|-----|-----|-----|-----|-----|-----|-----|-----|-----|-----|-----|-----|-----|-----|-----|-----|------|
| Ser | Thr | Gly | Ala | Gly | Lys | Leu | Arg | Gln | Ala | Leu | Thr | Thr | Cys | Asp | Asp |      |
| 765 |     |     |     |     | 770 |     |     |     |     | 775 |     |     |     |     | 780 |      |

| atc | tta | atc | aaa | cag | gac | cag | act | ctg | gct | gaa | ctg | cag | aac | aac | atg | 2884 |
|-----|-----|-----|-----|-----|-----|-----|-----|-----|-----|-----|-----|-----|-----|-----|-----|------|
| Ile | Leu | Ile | Lys | Gln | Asp | Gln | Thr | Leu | Ala | Glu | Leu | Gln | Asn | Asn | Met |      |
|     |     |     |     | 785 |     |     |     |     | 790 |     |     |     |     | 795 |     |      |

| gtg | cta | gtg | aaa | ctg | gac | ctt | cgg | aag | aag | gca | gca | tgt | att | gct | gag | 2932 |
|-----|-----|-----|-----|-----|-----|-----|-----|-----|-----|-----|-----|-----|-----|-----|-----|------|
| Val | Leu | Val | Lys | Leu | Asp | Leu | Arg | Lys | Lys | Ala | Ala | Cys | Ile | Ala | Glu |      |
|     |     |     | 800 |     |     |     |     | 805 |     |     |     |     | 810 |     |     |      |

| cag | tat | cat | act | gtg | ttg | aaa | ctc | caa | ggc | cag | gtt | tct | gcc | aaa | aag | 2980 |
|-----|-----|-----|-----|-----|-----|-----|-----|-----|-----|-----|-----|-----|-----|-----|-----|------|
| Gln | Tyr | His | Thr | Val | Leu | Lys | Leu | Gln | Gly | Gln | Val | Ser | Ala | Lys | Lys |      |
|     |     |     | 815 |     |     |     |     | 820 |     |     |     |     | 825 |     |     |      |

| cgc | ctt | ggt | acc | aac | cag | gaa | aat | cag | caa | cca | aac | caa | caa | cca | cca | 3028 |
|-----|-----|-----|-----|-----|-----|-----|-----|-----|-----|-----|-----|-----|-----|-----|-----|------|
| Arg | Leu | Gly | Thr | Asn | Gln | Glu | Asn | Gln | Gln | Pro | Asn | Gln | Gln | Pro | Pro |      |
|     | 830 |     |     |     |     | 835 |     |     |     |     | 840 |     |     |     |     |      |

| ggg | aag | aaa | cca | ttc | ctt | cga | aat | tta | ctt | ccc | cga | aca | cca | acc | tgc | 3076 |
|-----|-----|-----|-----|-----|-----|-----|-----|-----|-----|-----|-----|-----|-----|-----|-----|------|
| Gly | Lys | Lys | Pro | Phe | Leu | Arg | Asn | Leu | Leu | Pro | Arg | Thr | Pro | Thr | Cys |      |
| 845 |     |     |     |     | 850 |     |     |     |     | 855 |     |     |     |     | 860 |      |

| caa | agc | tca | aca | gac | tgc | agc | cct | tat | gcc | cgg | atc | cta | cgc | tca | cgg | 3124 |
|-----|-----|-----|-----|-----|-----|-----|-----|-----|-----|-----|-----|-----|-----|-----|-----|------|
| Gln | Ser | Ser | Thr | Asp | Cys | Ser | Pro | Tyr | Ala | Arg | Ile | Leu | Arg | Ser | Arg |      |
|     |     |     |     | 865 |     |     |     |     | 870 |     |     |     |     | 875 |     |      |

| cgt | tcc | cct | tta | ctc | aaa | tct | ggg | cct | ttt | ggc | aaa | aag | tac | taa |     | 3169 |
|-----|-----|-----|-----|-----|-----|-----|-----|-----|-----|-----|-----|-----|-----|-----|-----|------|
| Arg | Ser | Pro | Leu | Leu | Lys | Ser | Gly | Pro | Phe | Gly | Lys | Lys | Tyr |     |     |      |
|     |      | 880 |     |     |     |     | 885 |     |     |     |     | 890 |     |     |     |      |

| ggctgtgggg aaagagaaga gcagtcatgg ccctgaggtg ggtcagctac tctcctgaag | 3229 |
|---|---|
| aaataggtct cttttatgct ttaccatata tcaggaatta tatccaggat gcaatactca | 3289 |
| gacactagct ttttctcac ttttgtatta taaccaccta tgtaatctca tgttgttgtt | 3349 |
| tttttttatt tacttatatg atttctatgc acacaaaaac agttatatta aagatattat | 3409 |
| tgttcacatt ttttattgaa ttccaaatgt agcaaaatca ttaaaacaaa ttataaaagg | 3469 |
| ga | 3471 |

<210> SEQ ID NO 11
<211> LENGTH: 890
<212> TYPE: PRT
<213> ORGANISM: Homo sapiens

<400> SEQUENCE: 11

Met Ser Gln Gly Ile Leu Ser Pro Pro Ala Gly Leu Leu Ser Asp Asp
1               5                   10                  15

Asp Val Val Ser Pro Met Phe Glu Ser Thr Ala Ala Asp Leu Gly
            20                  25                  30

Ser Val Val Arg Lys Asn Leu Leu Ser Asp Cys Ser Val Val Ser Thr
            35                  40                  45

Ser Leu Glu Asp Lys Gln Gln Val Pro Ser Glu Asp Ser Met Glu Lys
        50                  55                  60

Val Lys Val Tyr Leu Arg Val Arg Pro Leu Leu Pro Ser Glu Leu Glu
65                  70                  75                  80

Arg Gln Glu Asp Gln Gly Cys Val Arg Ile Glu Asn Val Glu Thr Leu
                85                  90                  95

Val Leu Gln Ala Pro Lys Asp Ser Phe Ala Leu Lys Ser Asn Glu Arg
            100                 105                 110

Gly Ile Gly Gln Ala Thr His Arg Phe Thr Phe Ser Gln Ile Phe Gly
        115                 120                 125

Pro Glu Val Gly Gln Ala Ser Phe Phe Asn Leu Thr Val Lys Glu Met
130                 135                 140

Val Lys Asp Val Leu Lys Gly Gln Asn Trp Leu Ile Tyr Thr Tyr Gly
145                 150                 155                 160

Val Thr Asn Ser Gly Lys Thr His Thr Ile Gln Gly Thr Ile Lys Asp
                165                 170                 175

Gly Gly Ile Leu Pro Arg Ser Leu Ala Leu Ile Phe Asn Ser Leu Gln
            180                 185                 190

Gly Gln Leu His Pro Thr Pro Asp Leu Lys Pro Leu Leu Ser Asn Glu
        195                 200                 205

Val Ile Trp Leu Asp Ser Lys Gln Ile Arg Gln Glu Glu Met Lys Lys
210                 215                 220

Leu Ser Leu Leu Asn Gly Gly Leu Gln Glu Glu Glu Leu Ser Thr Ser
225                 230                 235                 240

Leu Lys Arg Ser Val Tyr Ile Glu Ser Arg Ile Gly Thr Ser Thr Ser
                245                 250                 255

Phe Asp Ser Gly Ile Ala Gly Leu Ser Ser Ile Ser Gln Cys Thr Ser
            260                 265                 270

Ser Ser Gln Leu Asp Glu Thr Ser His Arg Trp Ala Gln Pro Asp Thr
        275                 280                 285

Ala Pro Leu Pro Val Pro Ala Asn Ile Arg Phe Ser Ile Trp Ile Ser
290                 295                 300

Phe Phe Glu Ile Tyr Asn Glu Leu Leu Tyr Asp Leu Leu Glu Pro Pro
305                 310                 315                 320

Ser Gln Gln Arg Lys Arg Gln Thr Leu Arg Leu Cys Glu Asp Gln Asn
                325                 330                 335

Gly Asn Pro Tyr Val Lys Asp Leu Asn Trp Ile His Val Gln Asp Ala
            340                 345                 350

Glu Glu Ala Trp Lys Leu Leu Lys Val Gly Arg Lys Asn Gln Ser Phe
        355                 360                 365

Ala Ser Thr His Leu Asn Gln Asn Ser Ser Arg Ser His Ser Ile Phe
370                 375                 380

-continued

```
Ser Ile Arg Ile Leu His Leu Gln Gly Glu Gly Asp Ile Val Pro Lys
385                 390                 395                 400

Ile Ser Glu Leu Ser Leu Cys Asp Leu Ala Gly Ser Glu Arg Cys Lys
            405                 410                 415

Asp Gln Lys Ser Gly Glu Arg Leu Lys Glu Ala Gly Asn Ile Asn Thr
        420                 425                 430

Ser Leu His Thr Leu Gly Arg Cys Ile Ala Ala Leu Arg Gln Asn Gln
    435                 440                 445

Gln Asn Arg Ser Lys Gln Asn Leu Val Pro Phe Arg Asp Ser Lys Leu
450                 455                 460

Thr Arg Val Phe Gln Gly Phe Phe Thr Gly Arg Gly Arg Ser Cys Met
465                 470                 475                 480

Ile Val Asn Val Asn Pro Cys Ala Ser Thr Tyr Asp Glu Thr Leu His
            485                 490                 495

Val Ala Lys Phe Ser Ala Ile Ala Ser Gln Leu Val His Ala Pro Pro
        500                 505                 510

Met Gln Leu Gly Phe Pro Ser Leu His Ser Phe Ile Lys Glu His Ser
    515                 520                 525

Leu Gln Val Ser Pro Ser Leu Glu Lys Gly Ala Lys Ala Asp Thr Gly
530                 535                 540

Leu Asp Asp Asp Ile Glu Asn Glu Ala Asp Ile Ser Met Tyr Gly Lys
545                 550                 555                 560

Glu Glu Leu Leu Gln Val Val Glu Ala Met Lys Thr Leu Leu Leu Lys
            565                 570                 575

Glu Arg Gln Glu Lys Leu Gln Leu Glu Met His Leu Arg Asp Glu Ile
        580                 585                 590

Cys Asn Glu Met Val Glu Gln Met Gln Gln Arg Glu Gln Trp Cys Ser
    595                 600                 605

Glu His Leu Asp Thr Gln Lys Glu Leu Leu Glu Glu Met Tyr Glu Glu
610                 615                 620

Lys Leu Asn Ile Leu Lys Glu Ser Leu Thr Ser Phe Tyr Gln Glu Glu
625                 630                 635                 640

Ile Gln Glu Arg Asp Glu Lys Ile Glu Glu Leu Glu Ala Leu Leu Gln
            645                 650                 655

Glu Ala Arg Gln Gln Ser Val Ala His Gln Gln Ser Gly Ser Glu Leu
        660                 665                 670

Ala Leu Arg Arg Ser Gln Arg Leu Ala Ala Ser Ala Ser Thr Gln Gln
    675                 680                 685

Leu Gln Glu Val Lys Ala Lys Leu Gln Gln Cys Lys Ala Glu Leu Asn
690                 695                 700

Ser Thr Thr Glu Glu Leu His Lys Tyr Gln Lys Met Leu Glu Pro Pro
705                 710                 715                 720

Pro Ser Ala Lys Pro Phe Thr Ile Asp Val Asp Lys Lys Leu Glu Glu
            725                 730                 735

Gly Gln Lys Asn Ile Arg Leu Leu Arg Thr Glu Leu Gln Lys Leu Gly
        740                 745                 750

Glu Ser Leu Gln Ser Ala Glu Arg Ala Cys Cys His Ser Thr Gly Ala
    755                 760                 765

Gly Lys Leu Arg Gln Ala Leu Thr Thr Cys Asp Asp Ile Leu Ile Lys
770                 775                 780

Gln Asp Gln Thr Leu Ala Glu Leu Gln Asn Asn Met Val Leu Val Lys
785                 790                 795                 800

Leu Asp Leu Arg Lys Lys Ala Ala Cys Ile Ala Glu Gln Tyr His Thr
```

-continued

```
                805                 810                 815
Val Leu Lys Leu Gln Gly Gln Val Ser Ala Lys Lys Arg Leu Gly Thr
            820                 825                 830

Asn Gln Glu Asn Gln Gln Pro Asn Gln Gln Pro Pro Gly Lys Lys Pro
        835                 840                 845

Phe Leu Arg Asn Leu Leu Pro Arg Thr Pro Thr Cys Gln Ser Ser Thr
        850                 855                 860

Asp Cys Ser Pro Tyr Ala Arg Ile Leu Arg Ser Arg Arg Ser Pro Leu
865                 870                 875                 880

Leu Lys Ser Gly Pro Phe Gly Lys Lys Tyr
                885                 890
```

KIF20A EPITOPE PEPTIDES FOR TH1 CELLS AND VACCINES CONTAINING THE SAME

TECHNICAL FIELD

The present invention relates to the field of biological science, more specifically to the field of cancer therapy. In particular, the present invention relates to novel peptides that are extremely effective as cancer vaccines and drugs for either or both of treating and preventing tumors.

CROSS-REFERENCES TO RELATED APPLICATIONS

This application is a National Stage of International Application No. PCT/JP2013/004248, filed Jul. 9, 2013, and which claims the benefit of U.S. Provisional Application No. 61/669,999, filed on Jul. 10, 2012, the entire contents of which are incorporated by reference herein.

REFERENCE TO SEQUENCE LISTING

This application includes a Sequence Listing as a text file named "87331-927963-SEQLIST.txt" created Dec. 17, 2014, and containing 8,548,730 bytes. The material contained in this text file is incorporated by reference in its entirety for all purposes.

BACKGROUND ART

CD8 positive cytotoxic T lymphocytes (CTLs) have been shown to recognize epitope peptides derived from the tumor-associated antigens (TAAs) found on the major histocompatibility complex (MHC) class I molecule, and then kill the tumor cells. Since the discovery of the melanoma antigen (MAGE) family as the first example of TAAs, many other TAAs have been discovered, primarily through immunological approaches (NPL 1, 2). Some of these TAAs are currently undergoing clinical development as immunotherapeutic targets.

TAAs which are indispensable for proliferation and survival of cancer cells are valiant as targets for immunotherapy, because the use of such TAAs may minimize the well-described risk of immune escape of cancer cells attributable to deletion, mutation, or down-regulation of TAAs as a consequence of therapeutically driven immune selection. Accordingly, the identification of new TAAs capable of inducing potent and specific anti-tumor immune responses, warrants further development. Thus, the clinical application of peptide vaccination strategies for various types of cancer is ongoing (NPL 3-10). To date, there have been several reports of clinical trials using these tumor-associated antigen derived peptides. Unfortunately, so far, these cancer vaccine trials have yielded only a low objective response rate has been observed in these cancer vaccine trials so far (NPL 11-13). Accordingly, there remains a need in the art for new TAAs suitable for use as immunotherapeutic targets.

The KIF20A gene (RAB6KIFL) has been first identified to play a role in the dynamics of the Golgi apparatus through direct interaction with Rab6 small GTPase (NPL 14). KIF20A belongs to the kinesin superfamily of motor proteins, which have critical functions in trafficking of molecules and organelles (NPL 15, NPL 16, NPL 17). Recently, Taniuchi K et al. reported that KIF20A was overexpressed in pancreatic cancer tissues (NPL 18). They found evidence for a critical role of KIF20A in pancreatic carcinogenesis.

Through gene expression profile analysis using a genome-wide cDNA microarray containing 23,040 genes, KIF20A was recently shown to be up-regulated in several cancers such as bladder cancer (PTL 1), small cell lung cancer (SCLC) (PTL 2) and hormone-refractory prostate cancer (HRPC) (PTL 3), the disclosures of which are incorporated by reference herein. Further, some epitope peptides of KIF20A gene products were also identified (PTL 4).

Taken together, this data suggests that KIF20A is a novel, potentially universal on-coantigen. Accordingly, epitope peptides derived from KIF20A may be applicable as cancer immunotherapeutics for the treatment of a wide array of cancers.

Recently, highly immunogenic KIF20A-derived cytotoxic T lymphocytes (CTL)-epitopes that can induce tumor-reactive and HLA-A2 (A*02:01)-restricted CTL from PBMCs of healthy volunteers (NPL 19, PTL 5) have been identified. Furthermore, KIF20A-derived HLA-A24-restricted CTL-epitopes have been also identified (PTL 6). Therefore, KIF20A remains an attractive target molecule applicable to cancer immunotherapy.

Tumor-specific $CD4^+$ helper T (Th) cells, especially T-helper type 1 (Th1) cells play a critical role in efficient induction of CTL-mediated antitumor immunity (NPL 20). The IFN-gamma primarily produced by Th1 cells is critical for induction and maintenance of long lived CTL responses, providing help through multiple interactions which are critical in the preservation of immunological memory (NPL 21, 22). The IFN-gamma secreted by Th1 cells also mediates direct antitumor or anti-angiogenic effect (NPL 23). Furthermore, it has been shown that Th cells must pave the way for entry of CTLs at tumor site (NPL 24). Therefore, identification of tumor-associated antigen (TAA)-derived Th cell epitopes that can activate specific Th1 cell is important for induction of an effective tumor immunity in tumor-bearing hosts; ideally, the design of effective vaccines should include multiple epitopes to stimulate both CTL and Th1 cells (NPL 25). However, no such epitope derived from KIF20A has yet been identified.

CITATION LIST

Patent Literature

[PTL 1] WO2006/085684
[PTL 2] WO2007/013665
[PTL 3] WO2008/102906
[PTL 4] WO2008/102557
[PTL 5] WO2010/047062
[PTL 6] WO2008/102557

Non Patent Literature

[NPL 1] Boon T, Int J Cancer 1993 May 8, 54(2): 177-80
[NPL 2] Boon T and van der Bruggen P, J Exp Med 1996 Mar. 1, 183(3): 725-9
[NPL 3] Harris C C, J Natl Cancer Inst 1996 Oct. 16, 88(20): 1442-55
[NPL 4] Butterfield L H et al., Cancer Res 1999 Jul. 1, 59(13): 3134-42
[NPL 5] Vissers J L et al., Cancer Res 1999 Nov. 1, 59(21): 5554-9
[NPL 6] van der Burg S H et al., J Immunol 1996 May 1, 156(9): 3308-14
[NPL 7] Tanaka F et al., Cancer Res 1997 Oct. 15, 57(20): 4465-8

[NPL 8] Fujie T et al., Int J Cancer 1999 Jan. 18, 80(2): 169-72
[NPL 9] Kikuchi M et al., Int J Cancer 1999 May 5, 81(3): 459-66
[NPL 10] Oiso M et al., Int J Cancer 1999 May 5, 81(3): 387-94
[NPL 11] Belli F et al., J Clin Oncol 2002 Oct. 15, 20(20): 4169-80
[NPL 12] Coulie P G et al., Immunol Rev 2002 October, 188: 33-42
[NPL 13] Rosenberg S A et al., Nat Med 2004 September, 10(9): 909-15
[NPL 14] Echard A, et al. Science 1998; 279:580-5.
[NPL 15] Echard A, et al. Science 1998; 279:580-5.
[NPL 16] Hirokawa N, et al. Curr Opin Cell Biol 1998; 10:60-73.
[NPL 17] Allan V J, and Schroer T A. Curr Opin Cell Biol 1999; 11:476-82.
[NPL 18] Taniuchi K, et al. Cancer Res 2005; 65:105-12.
[NPL 19] Imai K, et al. Br J Cancer; 104: 300-7.
[NPL 20] Chamoto K et al. Cancer Res 2004; 64: 386-90.
[NPL 21] Bevan M J. Nat Rev Immunol 2004; 4: 595-602.
[NPL 22] Shedlock D J and Shen H. Science 2003; 300: 337-9.
[NPL 23] Street S E et al. Blood 2001; 97: 192-7.
[NPL 24] Bos R, and Sherman L A. Cancer Res; 70: 8368-77.
[NPL 25] Melief C J et al. Nat Rev Cancer 2008; 8: 351-60.

SUMMARY OF INVENTION

In the context of the present invention, the present inventors considered an ideal peptide vaccine for cancer immunotherapy to be one that includes a single polypeptide containing epitopes for both CTL and Th cell, both of which are naturally proximal to each other (Kenter G G et al. N Engl J Med 2009; 361: 1838-47.).

To that end, the present inventors designed a strategy to identify novel KIF20A-derived Th1 cell epitopes recognized in the context of promiscuous HLA class II molecules and containing CTL epitopes, working on the presumption that epitopes so characterized would induce more efficient T cell-mediated tumor immunity. A computer algorithm predicting HLA class II-binding peptides and known CTL epitope sequences recognized by HLA-A24 (A*24:02) or A2-restricted CTLs was used to select candidate promiscuous HLA-class II-restricted Th1 cell epitopes containing CTL epitopes.

The present invention is based, at least in part, on the discovery of suitable epitope peptides that serve as targets of immunotherapy for inducing Th1 cell response. Recognizing that the KIF20A gene is up-regulated in a number of cancer types, including bladder cancer, breast cancer, cholangiocellular carcinoma, esophageal cancer, non-small cell lung cancer (NSCLC), pancreatic cancer, prostate cancer, renal carcinoma, small cell lung cancer (SCLC) and head-and-neck malignant tumor (HNMT), the present invention targets for further analysis the gene product of kinesin family member 20A (KIF20A) gene, more particularly the polypeptide set forth in SEQ ID NO: 11 encoded by the gene of GenBank Accession No. NM_005733 (SEQ ID NO: 10). KIF20A gene products containing epitope peptides that elicit Th1 cells specific to the corresponding molecule were particularly selected for further study. For example, peripheral blood mononuclear cells (PBMCs) obtained from a healthy donor or HNMT patients were stimulated using promiscuous HLA-DRs and/or DPs binding peptide derived from human KIF20A. Th1 cells that recognize HLA-DRs or DPs positive target cells pulsed with the respective candidate peptides were established, and HLA-DRs and/or DPs restricted epitope peptides that can induce potent and specific immune responses against KIF20A were identified. These results demonstrate that KIF20A is strongly immunogenic and the epitopes thereof are effective for tumor immunotherapy mediated through Th1 cell response. Additional studies revealed that the promiscuous HLA-DRs and/or DPs binding peptides containing at least one CTL epitope can also stimulate CTL response in the same donor in a KIF20A specific manner. These results confirm that KIF20A is strongly immunogenic and that epitopes thereof containing both Th cell and CTL epitopes are effective for tumor immunotherapy mediated through both Th1 cell and CTL responses.

It is therefore an object of the present invention to provide peptides having Th1 cell inducibility as well as an amino acid sequence selected from among SEQ ID NOs: 1, 2, 3 and 4. The present invention contemplates modified peptides, i.e., peptides having Th1 cell inducibility that are up to 30 amino acids in length and have a contiguous amino acid sequence selected from the amino acid sequence of SEQ ID NO: 11 (KIF20A), as well as functional equivalents thereof. Alternatively, the present invention also provides peptides having both Th1 cell and CTL inducibilities. In some embodiments, the peptides of the present invention correspond to the an amino acid sequence of SEQ ID NO: 1, 2, 3 or 4 or modified versions thereof, in which one, two or several amino acids are substituted, deleted, inserted and/or added, while the ability to induce Th1 cells is maintained.

When administered to a subject, the present peptides are preferably presented on the surface of one or more antigen-presenting cells that in turn induce Th1 cells. When the peptide of the present invention further contains at least one CTL epitope, such APCs also process the peptides to present CTL epitopes generated from the present peptides, and thus induce CTLs targeting the respective peptides. Therefore, it is a further object of the present invention to provide antigen-presenting cells presenting any of the present peptides or fragments thereof, as well as methods for inducing antigen-presenting cells.

Administration of one or more peptides of the present invention or polynucleotide(s) encoding such peptides, or antigen-presenting cells which present such peptides or fragments thereof results in the induction of a strong anti-tumor immune response. Accordingly, it is yet another object of the present invention to provide pharmaceutical agents or compositions that contain as active ingredient(s) one or more of the following: (a) one or more peptides of the present invention, (b) one or more polynucleotides encoding such peptide(s), and (c) one or more antigen-presenting cells of the present invention. Such pharmaceutical agents or compositions of the present invention find particular utility as vaccines.

It is yet a further object of the present invention to provide methods for the treatment and/or prophylaxis (i.e., prevention) of cancers (i.e., tumors), and/or prevention of a postoperative recurrence thereof. Methods for inducing Th1 cells or for inducing anti-tumor immunity that include the step of administering one or more peptides, polynucleotides, antigen-presenting cells or pharmaceutical agents or compositions of the present invention are also contemplated. Furthermore, the Th1 cells of the present invention also find use as vaccines against cancer, examples of which include, but are not limited to, bladder cancer, breast cancer, cholangiocellular carcinoma, esophageal cancer, non-small cell lung cancer (NSCLC), pancreatic cancer, prostate cancer, renal carcinoma, small cell lung cancer (SCLC) and head-and-neck malignant tumor (HNMT).

Examples of specifically contemplated objects of the present invention include the following:

[1] An isolated peptide having 10-30 amino acids in length and comprising a part of the amino acid sequence of SEQ ID NO: 11, wherein said peptide comprises an amino acid sequence selected from the group consisting of:

(a) a contiguous amino acid sequence having more than 9 amino acids in length selected from the amino acid sequence of SEQ ID NO: 1, 2, 3 or 4; and (b) an amino acid sequence in which one, two or several amino acids are substituted, deleted, inserted, and/or added in the amino acid sequence of (a), wherein said peptide has ability to induce T helper type 1 (Th1) cells.

[2] The isolated peptide of [1], wherein the peptide or fragment thereof has abilities to bind at least two kinds of MHC class II molecules.

[3] The isolated peptide of [2], wherein the MHC class II molecules are selected from the group consisting of HLA-DR4, HLA-DR15, HLA-DR53 and HLA-DP2.

[4] The isolated peptide of any one of [1] to [3], wherein said peptide comprises an amino acid sequence of a peptide having KIF20A-specific cytotoxic T lymphocyte (CTL) inducibility.

[5] The isolated peptide of [4], wherein said peptide comprises the amino acid sequence selected from the group consisting of:

(a) an amino acid sequence selected from the group consisting of SEQ ID NOs: 1, 2, 3 and 4; and (b) an amino acid sequence in which one, two or several amino acids are substituted, deleted, inserted, and/or added in the amino acid sequence of (a).

[6] An isolated polynucleotide encoding the peptide of any one of [1] to [5].

[7] A composition for inducing at least one of the cells selected from the group consisting of (i) Th1 cells, (ii) CTLs, (iii) antigen-presenting cells (APCs) having an ability to induce Th1 cells, and (iv) APCs having an ability to induce CTLs, wherein the composition comprises one or more peptide(s) of any one of [1] to [5], or one or more polynucleotide(s) encoding them, or a composition for inducing at least one type of cell selected from the group consisting of (i) Th1 cells, (ii) CTLs, (iii) antigen-presenting cells (APCs) having an ability to induce Th1 cells, and (iv) APCs having an ability to induce CTLs, wherein the composition comprises one or more peptide(s) of any one of [1] to [5], or one or more polynucleotide(s) encoding them.

[8] A pharmaceutical composition, wherein the composition comprises at least one active ingredient selected from the group consisting of:

(a) one or more peptide(s) of any one of [1] to [5];

(b) one or more polynucleotide(s) of [6];

(c) one or more APC(s) presenting the peptide of any one of [1] to [5] or fragment thereof on their surface;

(d) one or more Th1 cells that recognize(s) an APC presenting the peptide of any one of [1] to [5] or fragment thereof on its surface; and (e) combination of any two or more of (a) to (d) above; and is formulated for a purpose selected from the group consisting of:

(i) cancer treatment, (ii) cancer prevention, (iii) prevention of post-operative recurrence in cancer, and (iv) combinations of any two or more of (i) to (iii) above.

[9] The pharmaceutical composition of [8], wherein said composition is formulated for administration to a subject that has at least one selected from the group consisting of HLA-DR4, HLA-DR15, HLA-DR53 and HLA-DP2 as a MHC class II molecule, or the pharmaceutical composition of [8], wherein said composition is formulated for administration to a subject that has at least one MHC class II molecule selected from the group consisting of HLA-DR4, HLA-DR15, HLA-DR53 and HLA-DP2.

[10] The pharmaceutical composition of [8] or [9], wherein said composition further comprises one or more peptides having CTL inducibility.

[11] A composition for enhancing an immune response mediated with an MHC class II molecule, wherein the composition comprises at least one active ingredient selected from the group consisting of:

(a) one or more peptide(s) of any one of [1] to [5];

(b) one or more polynucleotide(s) of [6];

(c) one or more APC(s) presenting the peptide of any one of [1] to [5] or fragment thereof on their surface;

(d) one or more Th1 cell(s) that recognize(s) an APC presenting the peptide of any one of [1] to [5] or fragment thereof on its surface; and (e) combination of any two or more of (a) to (d) above.

[12] A method for inducing an APC having an ability to induce a Th1 cell, said method comprising a step of contacting an APC with the peptide of any one of [1] to [5] in vitro, ex vivo or in vivo.

[13] A method for inducing an APC having an ability to induce a CTL, said method comprising a step selected from the group consisting of:

(a) contacting an APC with the peptide of any one of [1] to [5] in vitro, ex vivo or in vivo; and (b) introducing a polynucleotide encoding the peptide of any one of [1] to [5] into an APC.

[14] A method for inducing a Th1 cell, said method comprising a step selected from the group consisting of:

(a) co-culturing a CD4-positive T cell with an APC that presents on its surface a complex of an MHC class II molecule and the peptide of any one of [1] to [5] or fragment thereof; and (b) introducing a polynucleotide encoding both of T cell receptor (TCR) subunits, or polynucleotides encoding each of TCR subunits into a CD4-positive T cell, wherein the TCR can bind to a complex of an MHC class II molecule and the peptide of any one of [1] to [5] or fragment thereof presented on cell surface, or a method for inducing a Th1 cell, said method comprising a step selected from the group consisting of:

(a) co-culturing a CD4-positive T cell with an APC that presents on its surface a complex of an MHC class II molecule and the peptide of any one of [1] to [5] or fragment thereof; and (b) introducing a single polynucleotide encoding both T cell receptor (TCR) subunits, or multiple polynucleotides each encoding a separate TCR subunit into a CD4-positive T cell, wherein the TCR can bind to a complex of an MHC class II molecule and the peptide of any one of [1] to [5] or fragment thereof presented on a cell surface of an APC.

[15] A method for inducing a CTL, said method comprising the step selected from the group consisting of:
(a) co-culturing both of a CD4-positive T cell and a CD8-positive T cell with APCs contacted with the peptide of [4] or [5]; and
(b) co-culturing a CD8-positive T cell with an APC contacted with the peptide of [4] or [5].

[16] A method for enhancing an immune response mediated by an MHC class II molecule, wherein the method comprises a step of administering to a subject at least one active ingredient selected from the group consisting of:
(a) one or more peptide(s) of any one of [1] to [5];
(b) one or more polynucleotide(s) of [6];
(c) one or more APC(s) presenting the peptide of any one of [1] to [5] or fragment thereof on their surface;
(d) one or more Th1 cell(s) that recognize(s) an APC presenting the peptide of any one of [1] to [5] or fragment thereof on its surface; and
(e) combination of any two or more of (a) to (d) above.

[17] An isolated APC that presents on its surface a complex of an MHC class II molecule and the peptide of any one of [1] to [5] or fragment thereof.

[18] The APC induced by the method of [12] or [13].

[19] An isolated Th1 cell that recognizes the peptide of any one of [1] to [5] or fragment thereof presented on a surface of an APC.

[20] The Th1 cell induced by the method of [14].

[21] A method of inducing an immune response against cancer in a subject in need thereof, said method comprising the step of administering to the subject a composition comprising at least one active ingredient selected from the group consisting of:
(a) one or more peptide(s) of any one of [1] to [5];
(b) one or more polynucleotide(s) of [6];
(c) one or more APC(s) presenting the peptide of any one of [1] to [5] or fragment thereof on their surface;
(d) one or more Th1 cell(s) that recognize(s) an APC presenting the peptide of any one of [1] to [5] or fragment thereof on its surface; and
(e) combination of any two or more of (a) to (d) above.

[22] An antibody or immunologically active fragment thereof against the peptide of any one of [1] to [5].

[23] A vector comprising a nucleotide sequence encoding the peptide of any one of [1] to [5].

[24] A host cell transformed or transfected with the expression vector of [23].

[25] A diagnostic kit comprising the peptide of any one of [1] to [5], the polynucleotide of [6] or the antibody of [22].

In addition to the above, other objects and features of the invention will become more fully apparent when the following detailed description is read in conjunction with the accompanying figures and examples. However, it is to be understood that both the foregoing summary of the invention and the following detailed description are of exemplified embodiments, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments which follows.

FIG. 1 presents promiscuous HLA class II-binding KIF20A-derived peptides including CTL epitopes predicted by the computer algorithm (consensus method). Part A depicts the results of the analysis of the amino acid sequence of the human KIF20A protein using a computer algorithm (IEDB analysis resource, consensus method, tools.immuneepitope.org/analyze/html/mhc_II_binding.html). The numbers of horizontal axis indicate the amino acid residue positions of N-terminus of KIF20A-derived 15-mer peptides. A small numbered percentile rank indicates high affinity to HLA class II molecules.

[FIG. 1B] Part B depicts the four long peptides (KIF20A (60-84), 25-mer; KIF20A (494-517), 24-mer; KIF20A (809-833), 25-mer; KIF20A (843-863), 22-mer) that have overlapping high consensus percentile ranks for multiple HLA-class II allelic products (DRB1*04:05, DRB1*15:02, and DRB4*01:03) were selected (A, black bars numbered 1-4). KIF20A (60-84) and KIF20A (809-833) include 10-mer or 9-mer peptides recognized in the context of HLA-A24 or -A2 respectively by CTLs.

[FIG. 2A1] FIG. 2 presents the induction of KIF20A-specific CD4$^+$ T cells by stimulation with long peptides and identification of restriction HLA-class II molecules. CD4$^+$ T cell lines were generated from 2 healthy donors with various HLA-class II genotypes after at least 3 rounds of stimulation with KIF20A (60-84) or KIF20A (809-833), and the numbers of IFN-gamma-producing CD4$^+$ T cells were analyzed by ELISPOT assay. In Part A, responses against KIF20A (60-84)- or KIF20A (809-833)-pulsed autologous PBMCs are shown for 3 healthy donors. The CD4$^+$ T cells were stimulated with PBMC alone (−), PBMC pulsed with KIF20A (60-84) or KIF20A (809-833) (10 micro-g/ml), or PBMC pulsed with KIF20A (60-84) or KIF20A (809-833) in the presence of 5 micro-g/ml of mAb specific to HLA-DR, HLA-DP or HLA-DQ.

[FIG. 2A2] Responses against KIF20A (809-833)-pulsed autologous PBMCs are shown for 3 healthy donors.

[FIG. 2B] In part B, An HLA-DP-restricted and KIF20A (60-84)-specific CD4$^+$ T cell clone derived from a donor HDK1 was co-cultured with allogeneic PBMCs pulsed or unpulsed with KIF20A (60-84), or allogeneic PBMCs isolated from HLA-DP2-positive or negative four donors and pulsed with KIF20A (60-84) in the presence of anti-HLA-DR or anti-HLA-DP-blocking mAb (upper panel). A KIF20A (60-84)-specific bulk CD4$^+$ T cell line established from an HLA-DR15-positive healthy donor HDK2 was co-cultured with L-DR15 pulsed or unpulsed with KIF20A (60-84), or L-DR15 pulsed with KIF20A (60-84) in the presence of anti-HLA-DR or anti-HLA class I-blocking mAb, or L-DR8 pulsed or unpulsed with KIF20A (60-84). The numbers of IFN-gamma-producing Th cells were analyzed by an ELISPOT assay (lower panel).

[FIG. 2D] In part D, responses against KIF20A (494-517)-pulsed autologous PBMCs are shown for an HLA-DR4-positive healthy donor. The CD4$^+$ T cells were stimulated with PBMC alone (−), PBMC pulsed with KIF20A (494-517) (10 micro-g/ml), or PBMC pulsed with KIF20A (494-517) in the presence of 5 micro-g/ml of mAb specific to HLA-DR or HLA-DP (upper panel). A KIF20A (494-517)-specific CD4$^+$ T cell line established from an HLA-DR4-positive healthy donor HDK1 was co-cultured with L-DR4 pulsed or unpulsed with KIF20A (494-517), L-DR4 pulsed with WT1-peptide, L-DR4 pulsed with KIF20A (494-517) in the presence of anti-HLA-DR or anti-HLA class I blocking mAb, or L-DR53 pulsed or unpulsed with KIF20A (494-517). The numbers of IFN-gamma-producing Th cells were analyzed by an ELISPOT assay (lower panel).

[FIG. 3A1] FIG. 3 presents the functional characterization of bulk KIF20A-specific CD4$^+$ Th cell line. In part A, after 20 h incubation period of T cells ($1\times10^4$) co-cultured with KIF20A (60-84)-pulsed autologous PBMC ($3\times10^4$) or KIF20A (809-833)-pulsed L-DR53 ($5\times10^4$), the culture medium were collected and the concentration of cytokines (IFN-gamma, TNF-alpha, GM-CSF, MIP1beta, IL-2, IL-4 and IL-7) were measured using Bio-Plex assay system. Data are presented as the mean+/−SD of triplicate assays.

FIG. 3A2 is a continuation of FIG. 3A1.

[FIG. 4A-B] FIG. 4 presents KIF20A (60-84)- and KIF20A (809-833)-specific Th clones recognizing autologous DCs loaded with the KIF20A protein. In part A, the HLA-DR15-restricted KIF20A (60-84)-specific Th clone established from donor HDK2 (left panel) or the HLA-DR53-restricted KIF20A (809-833)-specific Th clone established from donor HDK1 ($2\times10^4$/well) (right panel) were co-cultured with autologous DCs ($5\times10^3$/well) loaded with the recombinant KIF20A protein (50 micro-g/ml) in the presence of anti-HLA-DR or anti-HLA class I blocking mAb, control protein, or unloaded DCs. The numbers of IFN-gamma-producing Th clone were analyzed by an ELISPOT assay. Data are presented as the mean+/−SD of duplicate assays. Representative data from three independent experiments with similar results are shown. In part B, the HLA-DP2-restricted KIF20A (60-84)-specific Th clone established from the donor HDK1 ($2\times10^4$/well) were co-cultured with autologous DCs ($5\times10^3$/well) loaded with the recombinant KIF20A protein (50 micro-g/ml) in the presence of anti-HLA-DP or anti-HLA class I-blocking mAb, control protein. The numbers of IFN-gamma-producing Th clone were analyzed by an ELISPOT assay. Data are presented as the mean+/−SD of duplicate assays. Representative data from two independent experiments with similar results are shown.

FIG. 5 presents the KIF20A (60-84) LP inducing an expansion of KIF20A-A24 (66-75)-specific CD8$^+$ T cells in vitro. In part A, PBMCs ($2\times10^6$/well) were incubated with KIF20A (60-84) LP (7 micro-M) or KIF20A-A24 (66-75) SP (7 micro-M) for 2 weeks without addition of any cytokine. On days 0 and 7, KIF20A-derived LP and SP were added, then on day 14 of in vitro stimulation with peptides, the cells were harvested, stained with a PE-labeled tetramer of the HLA-A*24:02/KIF20A-A24 (66-75) peptide complex in combination with a FITC-labeled anti-human CD8 mAb, and analyzed by flow cytometry. Dots in the upper right quadrant represent CD8$^+$ tetramer$^+$ T cells. Events shown are gated for CD8$^+$ T cells. The numbers inside the plots indicate the percentage of the cell population with the upper right quadrant characteristic (CD8$^+$ tetramer$^+$ T cells). Data are representative of many independent experiments with similar results from two HLA-A24-positive healthy donors.

[FIG. 5B-C] In Part B, absolute number of CD8$^+$ tetramer$^+$ cells in individual culture wells (each dot represents the absolute number of KIF20A-A24 (66-75)-specific CTL in a culture well) among PBMC from an HLA-A24-positive healthy donor HDK5 (one of two HLA-A24-positive healthy donors). The lines within each group of plots show the median and "n.s." represent statistical "not significant" results analyzed by a nonparametric Mann-Whitney U test. In Part C, the cells were harvested on day 14 of in vitro stimulation with the peptides and assessed by IFN-gamma ELISPOT assay. Bars indicate the number of IFN-gamma spots when the cells ($1\times10^5$/well) were re-stimulated with C1R2402 cells ($2\times10^4$/well) loaded with KIF20A (66-75) or irrelevant HIV-A24 peptides. Representative data from 4 independent experiments with similar results are shown. Data are presented as the mean+/−SD of duplicate assays. Statistically significant differences ($p<0.05$) are indicated with asterisks.

[FIG. 6A-B] FIG. 6 presents the KIF20A (809-833) LP stimulating KIF20A-A2 (809-817)-specific CD8$^+$ T cells in vitro. In Part A, the frequency of CD8$^+$ T cells specific to the KIF20A-A2 (809-817) SP in the CTL lines generated from a donor HDK6 was examined by IFN-gamma ELISPOT assay. The number of IFN-gamma producing KIF20A-A2 (809-817) SP-specific bulk CTL upon stimulation with the KIF20A-A2 (809-817) SP or an irrelevant SP-pulsed T2 cells was counted. In Part B, the number of IFN-gamma producing KIF20A-A2 (809-817) SP-specific bulk CTL upon stimulation with the KIF20A (809-833) LP-loaded or unloaded DCs, an irrelevant LP-loaded DCs, or KIF20A (809-833) LP-loaded DCs in the presence of anti-HLA-DR or anti-HLA class I blocking mAb was counted by an ELISPOT assay. Data are presented as the mean+/−SD of duplicate assays. Statistically significant differences ($p<0.05$) are indicated with asterisks.

FIG. 7 presents the enhanced induction of KIF20A-SP-specific CTLs by KIF20A-LP-specific CD4+ T-cells. In Part A, PBMCs from an HLA-A2+/DR53+ healthy donor (HDK1), from which an HLA-DR53-restricted KIF20A (809-833) LP-specific Th-clone was generated, were cultured for 11 days with KIF20A-A2 (809-817) SP (SP), KIF20A (809-833) LP (LP), KIF20A-A2 (809-817) SP+KIF20A (809-833) LP (SP+LP), KIF20A (809-833) LP+KIF20A (809-833) LP-specific Th clone (LP+Th-clone) or SP+LP+KIF20A (809-833) LP-specific Th-clone (SP+LP+Th-clone). On day 11, the cells were stained with KIF20A-A2 (809-817) SP-specific tetramer with an anti-human CD8 mAb and were analyzed by flow cytometry.

[FIG. 7C-D] In Part C, CD107a expression of KIF20A-A24 (66-75) SP-specific CD8+ T-cells expanded by activated KIF20A (809-833) LP-specific Th cells. KIF20A (809-833) LP-specific bulk CD4+ T-cells and KIF20A-A24 (66-75) SP-specific bulk CD8+ T-cells derived from HLA-A24+/DR15+ (HDK5) were cultured with autologous DCs in the presence of KIF20A-A24 (66-75) SP (SP alone), KIF20A-A24 (66-75) SP+Control LP (Control LP+SP), or KIF20A-A24 (66-75) SP+KIF20A (809-833) LP (KIF20A (809-833)-LP+SP) without addition of any cytokine. After 1-week in vitro culture with peptides, the cultured cells were stained with PE-labeled tetramer of the HLA-A*24:02/KIF20A-A24 (67-75) complex and PerCP-labeled anti-human CD8 mAb. Data are presented as the mean+/−SD of triplicate assays. Representative data from 3 independent experiments with similar results are shown. In Part D, After 1-week in vitro culture with peptides, the cultured cells were re-stimulated with KIF20A-A24 (66-75) SP and stained with PE-labeled tetramer of the HLA-A*24:02/KIF20A-A24 (67-75) complex, FITC-labeled anti-human CD107a mAb, and PerCP-labeled anti-human CD8 mAb. The absolute number of KIF20A-A24 (66-75) SP-specific CTLs expressing CD107a on the cell surface after re-stimulation with KIF20A-A24 (66-75) SP was shown. Data are presented as the mean+/−SD of triplicate assays. Representative data from 3 independent experiments with similar results are shown.

FIG. 8 presents the presence of KIF20A-LPs-specific Th cells in PBMCs isolated from patients with HNMT receiving immunotherapy with TAA-derived CTL-epitope peptides. In Part A, after in vitro stimulation of PBMCs with a mixture of KIF20A (60-84) LP and KIF20A (809-833) LP for 1 week, the frequency of individual KIF20A-LPs-specific T-cells was detected by IFN-gamma ELISPOT assay.

[FIG. 8B] In Part B, KIF20A-LPs-specific Th1 cell responses were assessed in 16 patients with HNMT receiving immunotherapy and in 9 healthy donors. The results represent specific IFN-gamma spots after background subtraction. Each dot represents an individual donor. Horizontal lines denote median values, and p values represent statistical results from a nonparametric Mann-Whitney U test.

[FIG. 8C-D] In Part C, HLA class II-restriction of the IFN-gamma-producing KIF20A (809-833) LP-specific Th cells in HNMT31 and HNMT43. Peripheral blood mononuclear cells stimulated with LPs for 1 week were restimulated with KIF20A (809-833) LP in the presence of mAbs specific to HLA-DR, -DP, -DQ, or HLA-class I. In Part D, KIF20A-LPs-specific Th1 cell responses in patients with HNMT were detected during the course of immunotherapy.

[FIG. 8F] In Part F, clinical characteristics of HNMT patients are shown. KIF20A-specific T-cell responses measured by IFN-gamma ELISPOT assay as detailed in the Materials and Methods section. Positive and negative responses are denoted by (+) and (−), respectively. The underlined HLA-class II alleles encode HLA-class II-molecules presenting KIF20A-LP to Th cells in healthy donors (FIG. 2; HLA-DRB1*15:02, DR53, and DPB1*02:01). IHC, Immunohistochemistry; CTR, Clinical Trials Registry; HNMT, Head-and-neck malignant tumor; M/F, male/female; LP, long peptide; n.t., not tested; DR53, DRB4*01:03.

DESCRIPTION OF EMBODIMENTS

Figure 1A:
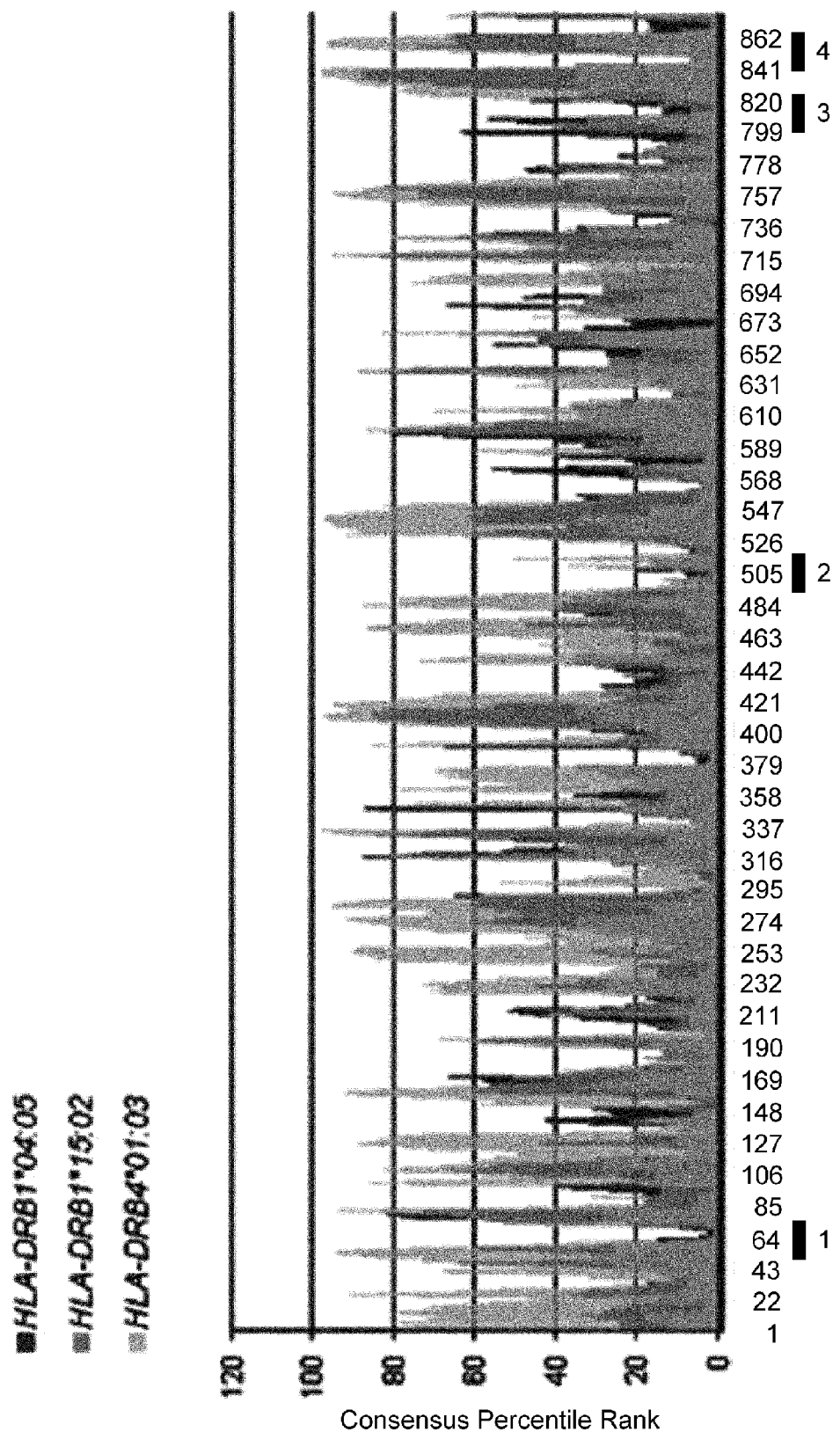
[FIG. 1A]

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

I. DEFINITIONS

Unless otherwise defined, all technical and scientific terms used herein have the same meaning as commonly understood by one of ordinary skill in the art to which the present invention belongs. However, in case of conflict, the present specification, including definitions, will control.

The words "a", "an", and "the" as used herein mean "at least one" unless otherwise specifically indicated.

The terms "isolated" and "purified" used in relation with a substance (e.g., peptide, antibody, polynucleotide, etc.) indicates that the substance is substantially free from at least one substance that may else be included in the natural source. Thus, an isolated or purified peptide refers to peptide that are substantially free of cellular material such as carbohydrate, lipid, or other contaminating proteins from the cell or tissue source from which the peptide is derived, or substantially free of chemical precursors or other chemicals when chemically synthesized. The term "substantially free of cellular material" includes preparations of a peptide in which the peptide is separated from cellular components of the cells from which it is isolated or recombinantly produced. Thus, a peptide that is substantially free of cellular material includes preparations of polypeptide having less than about 30%, 20%, 10%, or 5% (by dry weight) of heterologous protein (also referred to herein as a "contaminating protein"). When the peptide is recombinantly produced, it is also preferably substantially free of culture medium, which includes preparations of peptide with culture medium less than about 20%, 10%, or 5% of the volume of the peptide preparation. When the peptide is produced by chemical synthesis, it is preferably substantially free of chemical precursors or other chemicals, which includes preparations of peptide with chemical precursors or other chemicals involved in the synthesis of the peptide less than about 30%, 20%, 10%, 5% (by dry weight) of the volume of the peptide preparation. That a particular peptide preparation contains an isolated or purified peptide can be shown, for example, by the appearance of a single band following sodium dodecyl sulfate (SDS)-polyacrylamide gel electrophoresis of the protein preparation and Coomassie Brilliant Blue staining or the like of the gel. In a preferred embodiment, peptides and polynucleotides of the present invention are isolated or purified.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly function to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine, sulfoxide, methionine methyl sulfonium). The phrase "amino acid mimetic" refers to chemical compounds that have different structures but similar functions to general amino acids.

Amino acids may be referred to herein by their commonly known three letter symbols or the one-letter symbols recommended by the IUPAC-IUB Biochemical Nomenclature Commission.

The terms "gene", "polynucleotide" and "nucleic acid" are used interchangeably herein and, unless otherwise specifically indicated, are referred to by their commonly accepted single-letter codes.

The terms "agent" and "composition" are used interchangeably herein to refer to a product that includes specified ingredients in specified amounts, as well as any product that results, directly or indirectly, from combination of the specified ingredients in the specified amounts. Such term in relation to pharmaceutical composition, is intended to encompass a product including the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically or physiologically acceptable carrier.

The term "active ingredient" herein refers to a substance in a composition that is bio-logically or physiologically active. Particularly, in the context of a pharmaceutical composition, the term "active ingredient" refers to a component substance that shows an objective pharmacological effect. For example, in case of pharmaceutical compositions for use in the treatment or prevention of cancer, active ingredients in the compositions may lead to at least one biological or physiological action on cancer cells and/or tissues directly or indirectly. Preferably, such action may include reducing or inhibiting cancer cell growth, damaging or killing cancer cells and/or tissues, and so on. Typically, indirect effect of active ingredients is inductions of immune responses mediated by MHC Class II molecules. Before being formulated, the "active ingredient" may also be referred to as "bulk", "drug substance" or "technical product".

The phrase "pharmaceutically acceptable carrier" or "physiologically acceptable carrier", as used herein, means a pharmaceutically or physiologically acceptable material, composition, substance or vehicle, including, but are not limited to, a liquid or solid filler, diluent, excipient, solvent or encapsulating material.

Unless otherwise defined, the term "cancer" refers to cancers overexpressing KIF20A gene, including, for example, bladder cancer, breast cancer, cholangiocellular carcinoma, esophageal cancer, non-small cell lung cancer (NSCLC), pancreatic cancer, prostate cancer, renal carcinoma, small cell lung cancer (SCLC) and head-and-neck malignant tumor (HNMT).

Unless otherwise defined, the terms "T lymphocyte" and "T cell" are used interchangeably herein.

Unless otherwise defined, the term "cytotoxic T lymphocyte", "cytotoxic T cell" and "CTL" are used interchangeably herein and, otherwise specifically indicated, refer to a sub-group of T lymphocytes that are capable of recognizing non-self cells (e.g., tumor cells, virus-infected cells) and inducing the death of such cells. CTLs are differentiated from $CD8^+$ T lymphocytes and can recognize peptides presented by MHC class I molecules.

Unless otherwise defined, the terms "HLA-A24" refers to the HLA-A24 type containing the subtypes, examples of which include, but are not limited to, HLA-A*2401, HLA-A*2402, HLA-A*2403, HLA-A*2404, HLA-A*2407, HLA-A*2408, HLA-A*2420, HLA-A*2425 and HLA-A*2488.

Unless otherwise defined, "HLA-A2", as used herein, representatively refers to the subtypes, examples of which include, but are not limited to, HLA-A*0201, HLA-A*0202, HLA-A*0203, HLA-A*0204, HLA-A*0205, HLA-A*0206, HLA-A*0207, HLA-A*0210, HLA-A*0211, HLA-A*0213, HLA-A*0216, HLA-A*0218, HLA-A*0219, HLA-A*0228 and HLA-A*0250.

Unless otherwise defined, the terms "T helper type 1 cell" and "Th1 cell" are used interchangeably herein and, otherwise specifically indicated, refer to a sub-group of CD4+ T lymphocytes that are capable of recognizing peptides presented by an MHC class II molecules, and associated with cellular immunity. Unless otherwise defined, the terms "Th cell", "CD4+ T cell" and "CD4+ helper T cell" are also used interchangeably herein. Th1 cells secrete a variety of cytokines (such as IFN-gamma, IL-2, TNF-beta, GM-CSF, TNF-alpha, and so on) to help activation and/or stimulation of other immune cells relating to cellular immunity (e.g., CTL, macrophage).

Unless otherwise defined, the terms "HLA-DR4" refers to the subtypes, examples of which include, but are not limited to, HLA-DRB1*04:01, HLA-DRB1*04:02, HLA-DRB1*04:03, LA-DRB1*04:04, HLA-DRB1*04:05, HLA-DRB1*04:06, HLA-DRB1*04:07, HLA-DRB1*04:08, HLA-DRB1*04:09, HLA-DRB1*04:10 and HLA-DRB1*04:11.

Unless otherwise defined, the term "HLA-DR9" refers to the subtypes, examples of which include, but are not limited to, HLA-DRB1*09:01, HLA-DRB1*09:02, HLA-DRB1*09:03, LA-DRB1*09:04, HLA-DRB1*09:05, HLA-DRB1*09:06, HLA-DRB1*09:07, HLA-DRB1*09:08 and HLA-DRB1*09:09.

Unless otherwise defined, the term "HLA-DR15" refers to the subtypes, examples of which include, but are not limited to, HLA-DRB1*15:01, HLA-DRB1*15:02, HLA-DRB1*15:03, LA-DRB1*15:04, HLA-DRB1*15:05, HLA-DRB1*15:06, HLA-DRB1*15:07, HLA-DRB1*15:08, HLA-DRB1*15:09, HLA-DRB1*15:10 and HLA-DRB1*15:11.

Unless otherwise defined, the term "HLA-DR53" refers to the subtypes, examples of which include, but are not limited to, HLA-DRB4*01:01 and HLA-DRB4*01:03. Unless otherwise defined, the term "HLA-DP2" refers to the subtypes, examples of which include, but are not limited to, HLA-DPB1*0201 and HLA-DPB1*02:02.

Unless otherwise defined, the phrase "immune response mediated with an MHC class II molecule" refers to immune responses induced by presentation of peptide by MHC class II molecule. Herein, "immune response mediated with an MHC class II antigen" includes immune responses induced by CD4+ T cells, in particular, Th1 cells. Examples of such immune responses include, but not limited to, production of cytokines (such as IFN-gamma, IL-2, TNF-beta, GM-CSF, TNF-alpha, and so on) and activation and/or stimulation of other immune cells (such as CTL, macrophage, and so on).

Unless otherwise defined, the phrase "Th1 cell specific to KIF20A" refers to a Th1 cell that is specifically activated with an antigen presenting cell presenting a peptide derived from KIF20A, but not with other antigen presenting cells.

Unless otherwise defined, the phrase "KIF20A-specific CTL" refers to a CTL that specifically shows cytotoxicity against a target cell expressing KIF20A.

Unless otherwise defined, when used in the context of peptides, the phrase "CTL inducibility" refers to an ability of a peptide to induce a CTL when presented on an antigen-presenting cell.

Unless otherwise defined, the term "kit" as used herein, is used in reference to a combination of reagents and other materials. It is contemplated herein that the kit may include microarray, chip, marker, and so on. It is not intended that the term "kit" be limited to a particular combination of reagents and/or materials.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an antibody herein is used in the broadest sense and specifically covers intact monoclonal antibodies, polyclonal antibodies, multispecific antibodies (e.g., bispecific antibodies) formed from at least two intact antibodies, and antibody fragments so long as they exhibit the desired biological activity. An "antibody" indicates all classes (e.g., IgA, IgD, IgE, IgG and IgM).

Unless otherwise defined, all technical and scientific terms used herein have the same meaning as commonly understood by one of ordinary skill in the art to which this invention belongs.

II. PEPTIDES

Peptides of the present invention described in detail below may be referred to as "KIF20A peptide(s)" or "KIF20A polypeptide(s)".

To demonstrate that peptides derived from KIF20A function as an antigen recognized by T helper type 1 (Th1) cells, peptides derived from KIF20A (SEQ ID NO: 11) were analyzed to determine whether they were antigen epitopes promiscuously restricted by MHC class II molecules. Candidates of promiscuous MHC class II binding peptides derived from KIF20A were identified based on their binding affinities to HLA-DR4, HLA-DR15, HLA-DR53 and HLA-DP2. After in vitro stimulation of CD 4+ T-cells by dendritic cells (DCs) loaded with these peptides, Th1 cells were successfully established using each of the following peptides:

```
                                          (SEQ ID NO: 1)
KIF20A (60-84)/DSMEKVKVYLRVRPLLPSELERQED, (SEQ ID NO: 2)
KIF20A (809-833)/CIAEQYHTVLKLQGQVSAKKRLGTN, (SEQ ID NO: 3)
KIF20A (494-517)/TLHVAKFSAIASQLVHAPPMQLGF,
and (SEQ ID NO: 4)
KIF20A (843-863)/PPGKKPFLRNLLPRTPTCQSS.
```

These established Th1 cells noted above showed potent specific Th1 cell activity in response to stimulation of antigen presenting cells pulsed with respective peptides. Furthermore, the aforementioned peptides could stimulate Th1 cells restricted by several HLA-DR and HLA-DP molecules (e.g., HLA-DR4, HL-DR15, HLA-DR53 and HLA-DP2) which are frequently observed in the Japanese population. These results demonstrate that KIF20A is an antigen recognized by Th1 cells and that the peptides are epitope peptides of KIF20A promiscuously restricted by several HLA-class II molecules (such as HLA-DR4, HLA-DR53, HLA-DR15, and HLA-DP2); accordingly, such peptides may be effective as target antigens for cytotoxicity by CTLs.

The above identified peptides additionally contained an amino acid sequence of a CTL epitope having an ability to induce a CTL specific to KIF20A and, as demonstrated herein, such peptides can induce CTLs specific to KIF20A as well as Th1 cells. Accordingly, those peptides may be suitable peptides for induction of immune responses against cancer expressing KIF20A. Since the KIF20A gene is over-expressed in most cancer tissues, including, for example, bladder cancer, breast cancer, cholangiocellular carcinoma, esophageal cancer, non-small cell lung cancer (NSCLC), pancreatic cancer, prostate cancer, renal carcinoma, small cell lung cancer (SCLC) and head-and-neck malignant tumor (HNMT), it represents a good target for immunotherapy.

Accordingly, the present invention provides peptides having ability induce Th1 cells specific to KIF20A. The peptides of the present invention can bind at least one MHC class II molecule and be presented on antigen presenting cells. Alternatively, the fragment of the peptides of the present invention may bind at least one MHC class II molecule and be presented on antigen presenting cells. Those fragments of the peptides may be produced by processing within antigen presenting cells. In preferred embodiments, the peptides of the present invention or fragment thereof have abilities to bind two or more kinds of MHC class II molecules (e.g., HLA-DR4 and HLA-DR15, HLA-DR4 and HLA-DP2, HLA-DR15 and HLA-DP2, HLA-DR4, HLA-DR15 and HLA-DP2, HLA-DR15 and HLA-DR53, HLA-DP2 and HLA-DR53, or HLA-DR15, HLA-DR53 and HLA-DP2). In other words, the peptides of the present invention may have an ability to induce Th1 cells that are restricted by two or more kinds of MHC class II molecules. In another embodiment, the peptides of the present invention include an amino acid sequence of a peptide having KIF20A-specific CTL inducibility. The typical examples of such peptides having KIF20A-specific CTL inducibility include peptides having an amino acid sequence of SEQ ID NO: 5 or 6.

Since the binding groove in an MHC class II molecule is open at both ends, MHC class II binding peptides are allowed to have flexibility in their length. The core binding motif for MHC class II molecule is composed of 9 amino acid residues, and MHC class II binding peptides generally have other amino acid residues flanking with the core binding motif. The number of flanking amino acid residues is not restricted. Thus, all amino acid residues of SEQ ID NO: 1, 2, 3 or 4 are not indispensable for binding an MHC class II molecule. Accordingly, the peptide of the present invention can be a peptide having ability to induce a Th1 cell, such peptide including an amino acid sequence selected from the group consisting of:

(a) an amino acid sequence having more than 9 contiguous amino acids from the amino acid sequence of SEQ ID NO: 1, 2, 3 or 4; and (b) an amino acid sequence of (a) in which one, two or several amino acids are substituted, deleted, inserted, and/or added.

The length of an MHC class II binding peptides is generally 10-30 amino acids. In that the amino acid sequences of SEQ ID NO: 1, 2, 3 and 4 are composed of a part of the amino acid sequence of KIF20A (SEQ ID NO: 11), the peptides of the present invention can be a following peptide of [1] to [5]:

[1] An isolated peptide having 10-30 amino acids in length and including a part of the amino acid sequence of SEQ ID NO: 11, wherein such peptide comprises an amino acid sequence selected from the group consisting of:

(a) a contiguous amino acid sequence having more than 9 amino acids in length selected from the amino acid sequence of SEQ ID NO: 1, 2, 3 or 4; and (b) an amino acid sequence of (a) in which one, two or several amino acids are substituted, deleted, inserted, and/or added, wherein such peptide has ability to induce Th1 cell(s);

[2] The isolated peptide of [1], wherein the peptide or fragment thereof has abilities to bind at least two kinds of MHC class II molecules;

[3] The isolated peptide of [2], wherein the MHC class II molecules are selected from the group consisting of HLA-DR4, DR15, DR53 and DP2;

[4] The isolated peptide of any one of [1] to [3], wherein said peptide comprises an amino acid sequence of a peptide having KIF20A-specific cytotoxic T lymphocyte (CTL) inducibility; and

[5] The isolated peptide of [4], wherein said peptide comprises the amino acid sequence selected from the group consisting of:

(a) an amino acid sequence selected from the group consisting of SEQ ID NOs: 1, 2, 3 and 4; and (b) an amino acid sequence of (a) in which one, two or several amino acids are substituted, deleted, inserted, and/or added.

Th1 cells induced by the peptide of the present invention are specific to KIF20A.

Therefore, in some embodiments, the present invention provides peptides of less than 30 amino acid residues consisting of a partial amino acid sequence of the amino acid sequence of SEQ ID NO: 11, wherein the peptides comprise the amino acid sequence of SEQ ID NO: 1, 2, 3 or 4.

Generally, software programs presently available on the Internet, such as those described in Wang P et al. 2008. PLoS Comput Biol. 4(4):e1000048. 11:568; and Wang P et al. 2010. BMC Bioinformatics. can be used to calculate the binding affinities between various peptides and HLA antigens in silico. Binding affinity with HLA antigens can be measured as described, for example, in Nielsen M and Lund O. 2009. BMC Bioinformatics. 10:296; Nielsen M et al. 2007. BMC Bioinformatics. 8:238. Bui H H, et al. 2005. Immunogenetics. 57:304-314. Sturniolo T et al. 1999. Nat Biotechnol. 17(6):555-561 and Nielsen M et al. 2008. PLoS Comput Biol. 4(7)e1000107. Thus, the present invention encompasses peptides of KIF20A which are determined to bind with HLA antigens identified using such known programs.

As described above, since MHC class II binding peptides have flexibility in their length, the amino acid sequence of SEQ ID NO: 1, 2, 3 or 4 can be optionally flanked with additional amino acid residues so long as the resulting peptide retains the requisite Th1 cell inducibility. Such peptides having Th1 cell inducibility are typically, less than about 30 amino acids, often less than about 29 amino acids, and usually less than about 28 or 27 amino acids. The particular amino acid sequence(s) flanking the amino acid sequence selected from among SEQ ID NOs: 1, 2, 3 and 4 are not limited and can be composed of any kind of amino acids, so long as such flanking amino acid sequences do not impair the Th1 cell inducibility of the original peptide. In typical embodiments, such flanking amino acid sequence(s) may be selected from among the amino acid sequence of SEQ ID NO: 11 adjacent to the amino acid sequence of SEQ ID NO: 1, 2, 3 or 4; however, the present invention is not limited thereto. As such, the present invention also provides peptides having Th1 cell inducibility and an amino acid sequence selected from among SEQ ID NOs: 1, 2, 3 and 4.

On the other hand, since a core binding motif for an MHC class II molecule is composed of 9 amino acid residues, the full length of the amino acid sequence of SEQ ID NO: 1, 2, 3 or 4 is not indispensable for binding an MHC class II molecule and induction of Th1 cells. Thus, a peptide of the present invention can take the form of an amino acid having more than 9 contiguous amino acids of SEQ ID NO: 1, 2, 3 or 4, provided said peptide retains the requisite Th1 cell inducibility. Peptides having Th1 cell inducibility are typically, more than about 10 amino acids, often more than 11 or 12 amino acids, and usually more than 13 or 14 amino acids. Accordingly, the peptides of the present invention can be peptides having Th cell inducibility and an amino acid sequence having more than 9, 10, 11, 12, 13 or 14 contiguous amino acids from the amino acid sequence of SEQ ID NO: 1, 2, 3 or 4.

It is generally known that the modification of one, two, or more amino acids in a protein will not influence the function of the protein, and in some cases will even enhance the desired function of the original protein. In fact, modified peptides (i.e., peptides composed of an amino acid sequence in which one, two or several amino acid residues have been modified (i.e., substituted, added, deleted or inserted) as compared to an original reference sequence) have been known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention may have both Th1 cell inducibility and an amino acid sequence selected from among SEQ ID NO: 1, 2, 3 and 4, wherein one, two or even more amino acids are added, inserted, deleted and/or substituted. Alternatively, the peptides of the present invention may have both of Th1 cell inducibility and an amino acid sequence in which one, two or several amino acids are added, inserted, deleted and/or substituted in the amino acid sequence of SEQ ID NO: 1, 2, 3 or 4.

Those of skilled in the art recognize that individual additions or substitutions to an amino acid sequence which alter a single amino acid or a small percentage of amino acids tend to result in the conservation of the properties of the original amino acid side-chain. As such, they are often referred to as "conservative substitutions" or "conservative modifications", wherein the alteration of a protein results in a modified protein having a function analogous to the original protein. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also considered to be the peptides of the present invention. However, the peptides of the present invention are not restricted thereto and can include non-conservative modifications, so long as the modified peptide retains the Th1 cell inducibility of the original peptide. Furthermore, modified peptides should not exclude Th1 cell inducible peptides of polymorphic variants, interspecies homologues, and alleles of KIF20A.

To retain the requisite Th1 cell inducibility, one can modify (insert, add, deletion and/or substitute) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably, 15% of less, even more preferably 10% or 8%, less or 1 to 5%.

Homology analysis of preferred peptides of the present invention, namely SEQ ID NOs: 1, 2, 3 and 4 (KIF20A 60-84, 809-833, 494-517, 843-863), confirm that these peptides do not have significant homology with peptides derived from any other known human gene products. Thus, the possibility of these peptides generating unknown or undesired immune responses when used for immunotherapy is significantly lowered. Accordingly, these peptides are expected to be highly useful for eliciting immunity in cancer patients against KIF20A.

When used in the context of immunotherapy, the peptides of the present invention or fragment thereof should be presented on the surface of an antigen presenting cell, preferably as a complex with an HLA class II antigen. Therefore, it is preferable to select peptides that not only induce Th1 cells but also possess high binding affinity to the HLA class II antigen. To that end, the peptides can be modified by substitution, insertion, deletion and/or addition of the amino acid residues to yield a modified peptide having improved binding affinity.

The present invention also contemplates the addition of one to two amino acids to the N and/or C-terminus of the described peptides. Such modified peptides having high HLA antigen binding affinity and retained Th1 cell inducibility are also included in the present invention.

For example, the present invention provides an isolated peptide of less than 31, 30, 29, 28, 27, or 26 amino acids in length which binds an HLA class II antigen, has Th1 cell inducibility, and comprises the amino acid sequence in which one, two or several amino acid(s) are modified in the amino acid sequence selected from the group consisting of SEQ ID NOs: 1, 2, 3 and 4.

These peptides may also be processed in an APC to present a processed fragment thereon, when these peptides are contacted with, or introduced into APC. For example, the peptide of the present invention may be processed into a fragment composed of usually 11-26 (typically 15-25) amino acid residues to be presented on a surface of an APC.

However, when the peptide sequence is identical to a portion of the amino acid sequence of an endogenous or exogenous protein having a different function, negative side effects such as autoimmune disorders and/or allergic symptoms against specific substances may be induced. Therefore, it may be desirable to first perform homology searches using available databases to avoid situations in which the sequence of the peptide matches the amino acid sequence of another protein. When it becomes clear from the homology searches that no peptide identical to or having 1, 2, 3 or 4 amino acid differences as compared to the objective peptide exists in nature, the objective peptide can be modified in order to increase its binding affinity with HLA antigens, and/or increase its Th1 cell and/or CTL inducibility without any danger of such side effects.

Although peptides having high binding affinity to the HLA class II antigens as described above are expected to be highly effective, the candidate peptides, which are selected according to the presence of high binding affinity as an indicator, are further examined for the presence of Th1 cell inducibility. Herein, the phrase "Th1 cell inducibility" indicates an ability of a peptide to confer an ability to induce a Th1 cell on an APC when contacted with the APC. Further, "Th1 cell inducibility" includes the ability of the peptide to induce Th1 cell activation and/or Th1 cell proliferation, promote Th1 cell mediated-cytokines production including IFN-gamma production to help and/or stimulate other cells (e.g. CTL, macrophage).

Confirmation of Th1 cell inducibility is accomplished by inducing antigen-presenting cells carrying human MHC antigens (for example, B-lymphocytes, macrophages, and dendritic cells (DCs)), or more specifically DCs derived from human peripheral blood mononuclear leukocytes, and after stimulation with the peptides, mixing with CD4-positive T cells (CD4$^+$ T cells), and then measuring the IFN-gamma produced and released by CD4$^+$ T cells. Alternatively, Th1 cell inducibility of the peptide can be assessed based on CTL activation by Th1 cells. For example, CD4$^+$ T cells are co-cultured with DCs stimulated with a test peptide, and then mixing with CTLs and target cells for CTLs. The target cells can be radiolabeled with $^{51}$Cr and such, and cytotoxic activity of CTLs activated by the cytokines secreted from Th1 cells can be calculated from radioactivity released from the target cells. Alternatively, Th1 cells inducibility can be assessed by measuring IFN-gamma produced and released by Th1 cells in the presence of antigen-presenting cells (APCs) stimulated with a test peptide, and visualizing the inhibition zone on the media using anti-IFN-gamma monoclonal antibodies.

In addition to the above-described modifications, the peptides of the present invention can also be linked to other substances, so long as the resulting linked peptide retains the Th1 cell inducibility of the original peptide. Examples of suitable substances include, for example: peptides, lipids, sugar and sugar chains, acetyl groups, natural and synthetic polymers, etc. The peptides of the present invention can contain modifications such as glycosylation, side chain oxidation, or phosphorylation, etc., provided the modifications do not destroy the biological activity of the original peptide. These kinds of modifications can be performed to confer additional functions (e.g., targeting function, and delivery function) or to stabilize the peptide.

For example, to increase the in vivo stability of a peptide, it is known in the art to introduce D-amino acids, amino acid mimetics or unnatural amino acids; this concept can also be adapted to the peptides of the present invention. The stability of a peptide can be assayed in a number of ways. For instance, peptidases and various biological media, such as human plasma and serum, can be used to test stability (see, e.g., Verhoef et al., Eur J Drug Metab Pharmacokin 1986, 11: 291-302).

The peptides of the present invention may be presented on the surface of an APC as complexes in combination with HLA class II antigens and then induce Th1 cells. Therefore, the peptides forming complexes with HLA class II antigens on the surface of an APC are also included in the present invention. The APCs presenting the peptides of the present invention can be inoculated as vaccines.

The type of HLA antigens contained in the above complexes must match that of the subject requiring treatment and/or prevention. For example, in the Japanese population, HLA-DR4, DR53, DR15, and DP2 are prevalent and therefore would be appropriate for treatment of a Japanese patient. Typically, in the clinic, the type of HLA antigen of the patient requiring treatment is investigated in advance, which enables the appropriate selection of peptides having binding ability to the particular HLA class II antigen. In preferred embodiments, the peptides of the present invention can induce Th1 cells in a promiscuous manner. Herein, when a peptide can induce Th1 cells restricted by at least two different kinds of MHC class II molecules, the Th1 cell inducibility of the peptide is "promiscuous". In other word, when a peptide is recognized by at least two different kinds of MHC class II molecules, such antigen recognition is deemed "promiscuous". When used in the context of peptides, the phrase "recognized by at least two different kinds of MHC class II molecules" indicates that the peptide or fragment thereof can bind at least two different kinds of MHC class II molecules. For example, KIF20A (60-84) (SEQ ID NO: 1) is recognized by HLA-DR15, DP2 and DR4 or DR53, and KIF20A (809-833) (SEQ ID NO: 2) is recognizes by HLA-DR15 and DR53. Therefore, these peptides are typical examples of "promiscuous" epitope.

When using HLA-DR4, HLA-DR15, HLA-DR53 or HLA-DP2 positive APCs, the peptides having the amino acid sequence of SEQ ID NO: 1 are preferably used. When using HLA-DR15 or HLA-DR53 positive APCs, the peptides having the amino acid sequence of SEQ ID NO: 2 are preferably used. When using HLA-DR4 positive APCs, the peptides having the amino acid sequence of SEQ ID NO: 3 are preferably used. On the other hand, when using HLA-DR4 or DR53 positive APCs, preferred peptides are peptides having the amino acid sequence of SEQ ID NO: 4.

Accordingly, in preferred embodiments, peptides having the amino acid sequence of SEQ ID NO: 1 may be used for the induction of Th1 cells in a subject that has been identified as having HLA-DR4, HLA-DR15, HLA-DR53 or HLA-DP2 prior to the induction. Likewise, peptides having the amino acid sequence of SEQ ID NO: 2 may be used for the induction of Th1 cells in a subject that has been identified as having HLA-DR15 or HLA-DR53 prior to the induction. Similarly, peptides having the amino acid sequence of SEQ ID NO: 3 may be used for the induction of Th1 cells in a subject that has been identified as having HLA-DR4 prior to the induction. Peptides having the amino acid sequence of SEQ ID NO: 4 also may be used for the induction of Th1 cells in a subject that has been identified as having HLA-DR4 or HLA-DR53 prior to the induction.

III. PREPARATION OF KIF20A PEPTIDES

The peptides of the present invention can be prepared using well known techniques. For example, the peptides of the present invention can be prepared synthetically, using recombinant DNA technology or chemical synthesis. The peptide of the present invention can be synthesized individually or as longer polypeptides composed of two or more peptides. The peptides of the present invention can be then be isolated, i.e., purified, so as to be substantially free of other naturally occurring host cell proteins and fragments thereof, or any other chemical substances.

The peptides of the present invention may contain modifications, such as glycosylation, side chain oxidation, or phosphorylation; provided the modifications do not destroy the biological activity of the original reference peptides. Other illustrative modifications include incorporation of D-amino acids or other amino acid mimetics that can be used, for example, to increase the serum half life of the peptides.

Peptides of the present invention can be obtained through chemical synthesis based on the selected amino acid sequence. Examples of conventional peptide synthesis methods that can be adapted for the synthesis include:
 (i) Peptide Synthesis, Interscience, New York, 1966;
 (ii) The Proteins, Vol. 2, Academic Press, New York, 1976;
 (iii) Peptide Synthesis (in Japanese), Maruzen Co., 1975;
 (iv) Basics and Experiment of Peptide Synthesis (in Japanese), Maruzen Co., 1985;
 (v) Development of Pharmaceuticals (second volume) (in Japanese), Vol. 14 (peptide synthesis), Hirokawa, 1991;
 (vi) WO99/67288; and
 (vii) Barany G. & Merrifield R. B., Peptides Vol. 2, "Solid Phase Peptide Synthesis", Academic Press, New York, 1980, 100-118.

Alternatively, the peptides of the present invention can be obtained adapting any known genetic engineering method for producing peptides (e.g., Morrison J, J Bacteriology 1977, 132: 349-51; Clark-Curtiss & Curtiss, Methods in Enzymology (eds. Wu et al.) 1983, 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptide of the present invention can also be produced in vitro adopting an in vitro translation system.

IV. POLYNUCLEOTIDES

The present invention also provides a polynucleotide which encodes any of the aforementioned peptides of the present invention. These include polynucleotides derived from the natural occurring KIF20A gene (GenBank Accession No. NM_005733 (SEQ ID NO: 10)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. As is well known in the art, a DNA is suitably composed of bases such as A, T, C, and G, and T is replaced by U in an RNA. One of skill will recognize that non-naturally occurring bases may be included in polynucleotides, as well.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

V. ANTIGEN-PRESENTING CELLS (APCs)

The present invention also provides antigen-presenting cells (APCs) that present complexes formed between HLA class II antigens and the peptides of the present invention or fragment thereof on its surface. The APCs that are obtained by contacting the peptides of the present invention can be derived from patients who are subject to treatment and/or prevention, and can be administered as vaccines by themselves or in combination with other drugs including the peptides of the present invention, Th1 cells or CTLs.

The APCs are not limited to a particular kind of cells and include dendritic cells (DCs), Langerhans cells, macrophages, B cells, and activated T cells, which are known to present proteinaceous antigens on their cell surface so as to be recognized by lymphocytes. Since a DC is a representative APC having the strongest Th1 cell-inducing activity among APCs, DCs find use as the APCs of the present invention.

Moreover, in preferred embodiments, the peptides of the present invention can also induce CTL response mediated with the MHC class I antigen, as well as Th1 (class-II). In general, it is well known that the length of epitope recognized by the MHC-class I antigen is shorter (e.g. 8-10 amino acid residues) than that of MHC-class II (15 or more). Therefore, a processed product of the peptide of the present invention leads to induce CTL. In fact, CTL induced from KIF20A (60-84) (SEQ ID NO: 1) recognizes the fragment (KVYLRVRPLL: SEQ ID NO: 6) which has already been identified as a CTL recognition epitope. Likewise, KIF20A (809-833) (SEQ ID NO: 2) also comprises the CTL recognition epitope sequence CIAEQYHTV (SEQ ID NO: 5) in the amino acid sequence. Accordingly, peptides of the present invention induce not only Th1 but also CTL after processing of them in APCs. In other words, APCs contacted with the peptides of the present invention process them to present fragments thereof with MHC-class I antigens, as well as the whole of them presented with MHC-class-II antigens. Consequently, both of Th1 which recognizes the peptides of the present invention presented on APCs with the MHC class II antigen, and CTL induced via processed fragments of the peptide can be induced by using the peptides present invention.

For example, an APC can be obtained by inducing DCs from peripheral blood monocytes and then contacting (stimulating) them with the peptides of the present invention in vitro, ex vivo or in vivo. When the peptides of the present invention are administered to the subjects, APCs that present the peptides of the present invention or fragments thereof are induced in the body of the subject. Herein, the phrase "inducing an APC" includes contacting (stimulating) an APC with the peptides of the present invention to present complexes formed between HLA class II antigens and the peptides of the present invention or fragments thereof on their surface. Alternatively, after introducing the peptides of the present invention to APCs to allow the APCs to present the peptides or fragments thereof, the APCs can be administered to the subject as a vaccine. For example, the ex vivo administration can include steps of:

a: collecting APCs from a first subject,
b: contacting the APCs of step a, with the peptide of the present invention and
c: administering the peptide-loaded APCs to a second subject.

The first subject and the second subject may be the same individual, or can be different individuals. Alternatively, according to the present invention, use of the peptides of the present invention for manufacturing a pharmaceutical composition inducing antigen-presenting cells is provided. In addition, the present invention provides a method or process for manufacturing a pharmaceutical composition inducing antigen-presenting cells, wherein the method comprises the step for admixing or formulating the peptide of the present invention with a pharmaceutically acceptable carrier. Further, the present invention also provides the peptides of the present invention for inducing antigen-presenting cells. The APCs obtained by step (b) can be administered to the subject as a vaccine.

In one aspect of the present invention, the APCs of the present invention have a high level of Th1 cell inducibility. Herein, in the phrase "high level of Th1 cell inducibility", the high level is relative to the level of that by APCs contacting with no peptide or peptides which can not induce Th1 cells. Herein, when used in the context of APCs, the phrase "Th1 cell inducibility" indicates an ability of an APC to induce a Th1 cell when contacted with a CD4$^+$ T cell. Such APCs having a high level of Th1 cell inducibility can be prepared by a method which includes the step of transferring genes containing polynucleotides that encode the peptides of the present invention to APCs in vitro. The introduced genes can be in the form of DNAs or RNAs. Examples of methods for introduction include, without particular limitations, various methods conventionally performed in this field, such as lipofection, electroporation, and calcium phosphate method can be used. More specifically, it can be performed as described in Cancer Res 1996, 56: 5672-7; J Immunol 1998, 161: 5607-13; J Exp Med 1996, 184: 465-72; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present peptides. Alternatively, the APCs of the present invention can be prepared by a method which induces the step of contacting APCs with the peptide of the present invention.

In preferred embodiments, the APCs of the present invention can be APCs that present complexes of an MHC class II molecule selected from the group among HLA-DR4, HLA-DR15, HLA-DR53 and HLA-DP2 and the peptide of the present invention (including an amino acid sequence of SEQ ID NO: 1) on their surface. In another embodiment, the APCs of the present invention can be APCs that present complexes of an MHC class II molecule selected from the group among HLA-DR53 and HLA-DR15 and the peptide of the present invention (including an amino acid sequence of SEQ ID NO: 2) on their surface. In another embodiment, the APCs of the present invention can be APCs that present complexes of an HLA-DR4 and the peptide of the present invention (including an amino acid sequence of SEQ ID NO: 3) on their surface. In another embodiment, the APCs of the present invention can be APCs that present complexes of an MHC class II molecule selected from the group among HLA-DR4 and HLA-DR53 and the peptide of the present invention (including an amino acid sequence of SEQ ID NO: 4) on their surface. Preferably, HLA-DR4, HLA-DR15, HLA-DR53 and HLA-DP2 may be HLA-DRB1*04:05, HLA-DRB1*15:02, DRB4*01:03 and HLA-DPB1*02:01, respectively.

VI. T HELPER TYPE 1 CELLS (TH1 CELLS)

A Th1 cell induced against any of the peptides of the present invention strengthens immune responses of any of effector cells including CTLs targeting cancer cells in vivo, and thus serve as vaccines, in a fashion similar to the peptides per se. Thus, the present invention also provides isolated Th1 cells that are specifically induced or activated by any of the peptides of the present invention.

Such Th1 cells can be obtained by (1) administering one or more peptides of the present invention to a subject, collecting Th1 cells from the subject, (2) contacting (stimulating) APCs and CD4$^+$ T cells, or peripheral blood mononuclear leukocytes in vitro with the peptides of the present invention, and then isolating Th1 cells, (3) contacting CD4$^+$ T cells or peripheral blood mononuclear leukocytes in vitro with the APCs of the present invention, or (4) introducing a polynucleotide encoding both of T cell receptor (TCR) subunits or polynucleotides encoding each of TCR subunits into a CD4$^+$ T cell, wherein the TCR can bind to a complex of a MHC class II molecule and the peptide of the present invention. Such APCs for the method of (3) can be prepared by the methods described above. Details of the method of (4) is described bellow in section "VII. T cell receptor (TCR)".

Th1 cells that have been induced by stimulation with APCs of the present invention can be derived from patients who are subject to treatment and/or prevention, and can be administered by themselves or in combination with other drugs including the peptides of the present invention for the purpose of regulating effects. The obtained Th1 cells can activate and/or stimulate immune cells responsible for cellular immunity (e.g., CTL, macrophage). Such immune cells that can be activated by the Th1 cells of the present invention include CTLs that show cytotoxicity against target cells such as cancer cells. For example, target cells for such CTLs may be cells that endogenously express KIF20A (e.g., cancer cells), or cells that are transfected with the KIF20A gene. In preferred embodiments, the peptides of the present invention can contain at least one amino acid sequence of a CTL epitope peptide and also induce CTLs against KIF20A expressing cells such as cancer cells, in addition to Th1 cells. In this case, the peptide of the present invention can induce Th1 cells and CTLs simultaneously or sequentially in vivo, and the induced Th1 cells can effectively activate the induced CTLs. Accordingly, such peptides containing at least one amino acid sequence of a CTL epitope peptide are suitable peptides for cancer immunotherapy.

Furthermore, the Th1 cells of the present invention secrete various cytokines (e.g. IFN-gamma) which activate and/or stimulate any CTLs against other target cells in an antigen independent manner. Accordingly, the Th1 cells of the present invention can also contribute to enhance CTL activity targeting cells expressing a tumor associated antigen (TAA) other than KIF20A. Thus, the Th cells of the present invention are useful for immunotherapy for not only tumor expressing KIF20A, but also tumor expressing other TAAs, as well as the peptides and APCs of the present invention.

In some embodiments, the Th1 cells of the present invention are Th1 cells that recognize cells presenting complexes of an HLA-DR or HLA-DP antigen and the peptide of the present invention. In the context of Th1 cells, the phrase "recognize a cell" refers to binding of a complex of an MHC class II molecule and the peptide of the present invention on the cell surface via its TCR and being activated in an antigen specific manner. Herein, the phrase "activated in antigen specific manner" refers to being activated in response to a particular MHC class II molecule and peptide and cytokine production from the activated Th1 cells are induced. In preferred embodiments, HLA-DR may be selected from the group consisting of HLA-DR4, HLA-DR53 and HLA-DR15. Preferably, HLA-DR4, HLA-DR53 and HLA-DR15 may be HLA-DRB1*04:05, HLA-DRB4*0103 and HLA-DRB1*15:02, respectively. On the other hand, HLA-DP2 is a preferable example of the HLA-DP antigens. More preferably, HLA-DP2 may be HLA-DPB1*02:01.

VII. T CELL RECEPTOR (TCR)

The present invention also provides a composition containing one or more polynucleotides encoding one or more polypeptides that are capable of forming a subunit of a T cell receptor (TCR), and methods of using the same. Such TCR subunits have the ability to form TCRs that confer specificity to CD4+ T cells against APCs presenting KIF20A peptides. By using the known methods in the art, the nucleic acids of alpha- and beta-chains as the TCR subunits of Th cells induced by the peptides of the present invention can be identified (WO2007/032255 and Morgan et al., J Immunol, 171, 3288 (2003)). The derivative TCRs can bind APCs displaying KIF20A peptides with high avidity, and optionally mediate efficient cytokine productions.

The polynucleotide/polynucleotides encoding the TCR subunits (i.e., a single polynucleotide encoding both of the TCR subunits or multiple polynucleotides each encoding a separate TCR subunits) can be incorporated into suitable vectors e.g. retroviral vectors. These vectors are well known in the art. The polynucleotides or the vectors containing them usefully can be transferred into a CD4+ T cell, for example, a CD4+ T cell from a patient. Advantageously, the present invention provides an off-the-shelf composition allowing rapid modification of a patient's own T cells (or those of another mammal) to rapidly and easily produce modified T cells having excellent cancer cell killing properties.

The present invention further provides Th1 cells which are prepared by transduction with the polynucleotide encoding both of the TCR subunits or polynucleotides encoding each of TCR subunits, wherein the TCR subunit can bind to the KIF20A peptide (e.g. SEQ ID NO: 1 in the context of HLA-DR4, HLA-DR15, HLA-DR53 or HLA-DP2, SEQ ID NO: 2 in the context of HLA-DR53 or HLA-DR15, SEQ ID NO: 3 in the context of HLA-DR4 and SEQ ID NO: 4 in the context of HLA-DR4 or HLA-DR53). The transduced Th1 cells are capable of homing to cancer cells in vivo, and can be expanded by well known culturing methods in vitro (e.g., Kawakami et al., J Immunol., 142, 3452-3461 (1989)). The Th1 cells prepared as described above can be used to form an immunogenic composition useful in treating or the prevention of cancer in a patient in need of therapy or protection.

VIII. PHARMACEUTICAL AGENTS OR COMPOSITIONS

To the extent that the methods and compositions of the present invention find utility in the context of the "treatment" of cancer, a treatment is deemed "efficacious" if it leads to clinical benefit such as, reduction in expression of KIF20A gene, or a decrease in size, prevalence, or metastatic potential of the cancer in the subject. When the treatment is applied prophylactically, "efficacious" means that it retards or prevents cancers from forming or prevents or alleviates a clinical symptom of cancer. Efficaciousness is determined in association with any known method for diagnosing or treating the particular tumor type.

To the extent that the methods and compositions of the present invention find utility in the context of the "prevention" and "prophylaxis" of cancer, such terms are interchangeably used herein to refer to any activity that reduces the burden of mortality or morbidity from disease. Prevention and prophylaxis can occur "at primary, secondary and tertiary prevention levels." While primary prevention and prophylaxis avoid the development of a disease, secondary and tertiary levels of prevention and prophylaxis encompass activities aimed at the prevention and prophylaxis of the progression of a disease and the emergence of symptoms as well as reducing the negative impact of an already established disease by restoring function and reducing disease-related complications. Alternatively, prevention and prophylaxis include a wide range of prophylactic therapies aimed at alleviating the severity of the particular disorder, e.g. reducing the proliferation and metastasis of tumors, reducing angiogenesis.

In the context of the present invention, the treatment and/or prophylaxis of cancer and/or the prevention of post-operative recurrence thereof include any of the following steps, such as surgical removal of cancer cells, inhibition of the growth of cancerous cells, involution or regression of a tumor, induction of remission and suppression of occurrence of cancer, tumor regression, and reduction or inhibition of metastasis. Effectively treating and/or the prophylaxis of cancer decreases mortality and improves the prognosis of individuals having cancer, decreases the levels of tumor markers in the blood, and alleviates detectable symptoms accompanying cancer. For example, reduction or improvement of symptoms constitutes effectively treating and/or the prophylaxis include 10%, 20%, 30% or more reduction, or stable disease.

As described above, the Th1 cells induced by the peptides of the present invention can help immune cells responsible for cellular immunity. Such immune cells include CTLs against not only cancer cells expressing KIF20A, but also cancer cells expressing other TAAs, since cytokines secreted by Th1 cells can affect CTLs in antigen independent manner. Accordingly, the present invention provides a pharmaceutical agent or composition comprising at least one peptide of the present invention. In the pharmaceutical agent or composition, such peptide is present in a therapeutically or pharmaceutically effective amount. A pharmaceutical agent or composition of the present invention is useful for helping, stimulating and/or enhancing any immune cells responsible for cellular immunity (e.g., CTLs, macrophage), since Th1 cells induced by the agent or composition of the present invention can secrete cytokines that affects any immune cells responsible for cellular immunity. Therefore, the agent or composition of the present invention is useful for any purposes of enhancing or promoting immune responses mediated with such immune cells including CTLs. For example, the present invention provides agent or compositions comprising at least one of the peptide of the present invention, for use in treatment and/or prevention of cancer since the agent or composition of the present invention can enhance or promote immune responses against cancer or tumor mediated with such immune cells. The amount of the peptide in such agent or composition may be an amount that is effective in significantly enhancing or stimulating immunological response in a subject carrying a cancer expressing KIF20A.

Furthermore, as shown in FIGS. 5 and 6, KIF20A derived peptides identified in the course of the present invention have been confirmed to enhance CTL induction compared with stimulation with a CTL epitope only. Therefore, the present invention also provides an agent or composition for enhancing or stimulating immunological responses mediated with an MHC class I antigen, such as HLA-A2 and HLA-A24. In another embodiment, the present invention further provides a use of the peptide of the present invention for manufacturing an agent or composition for enhancing or stimulating an immunological response mediated with an MHC class I antigen.

In preferred embodiments, KIF20A derived peptides identified in the course of the present invention can induce Th1 cells, as well as CTLs against KIF20A-expressing cells. Accordingly, the present invention also provides agents or compositions comprising at least one of the peptide of the present invention, for use in the induction of CTLs against cancer or tumor expressing KIF20A.

Moreover, the agent or composition comprising at least one of the peptides of the present invention can be used in enhancing or promoting immune responses mediated by MHC class II molecules.

Since KIF20A expression is specifically elevated in several cancer types, including bladder cancer, breast cancer, cholangiocellular carcinoma, esophageal cancer, non-small cell lung cancer (NSCLC), pancreatic cancer, prostate cancer, renal carcinoma and small cell lung cancer (SCLC) as compared with normal tissue (WO2006/085684, WO2007/013665, WO2008/102906, WO2008/102557, WO2010/047062, WO2008/102557), the peptides of the present invention or polynucleotides encoding the peptides can be used for the treatment and/or prophylaxis of cancer or tumor, and/or for the prevention of postoperative recurrence thereof. Thus, the present invention provides a pharmaceutical agent or a composition for treating and/or for the prophylaxis of cancer or tumor, and/or prevention of postoperative recurrence thereof, which comprises one or more of the peptides of the present invention, or polynucleotides encoding the peptides as an active ingredient. Alternatively, the present peptides can be expressed on the surface of any of the foregoing cells, such as APCs for the use as pharmaceutical agents or compositions. In addition, the aforementioned Th1 cells can also be used as active ingredients of the present pharmaceutical agents or compositions.

In another embodiment, the present invention also provides the use of an active ingredient selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention
in manufacturing a pharmaceutical composition or agent for treating cancer or tumor.

Alternatively, the present invention further provides an active ingredient selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention
for use in treating cancer or tumor.

Alternatively, the present invention further provides a method or process for manufacturing a pharmaceutical composition or agent for treating cancer or tumor, wherein the method or process includes the step of formulating a pharmaceutically or physiologically acceptable carrier with an active ingredient selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention
as active ingredients.

In another embodiment, the present invention also provides a method or process for manufacturing a pharmaceutical composition or agent for treating cancer or tumor, wherein the method or process includes the step of admixing an active ingredient with a pharmaceutically or physiologically acceptable carrier, wherein the active ingredient is selected from among:
(a) a peptide of the present invention,
(b) a polynucleotide encoding such a peptide as disclosed herein in an expressible form,
(c) an APC presenting on its surface a peptide of the present invention or fragment thereof, and
(d) a Th1 cell of the present invention.

Alternatively, the pharmaceutical composition or agent of the present invention may be used for either or both of the prophylaxis of cancer or tumor and prevention of postoperative recurrence thereof.

The present pharmaceutical agents or compositions find use as a vaccine. In the context of the present invention, the phrase "vaccine" (also referred to as an immunogenic composition) refers to a composition that has the function to induce anti-tumor immunity upon inoculation into animals.

The pharmaceutical agents or compositions of the present invention can be used to treat and/or prevent cancers or tumors, and/or prevent postoperative or metastatic recurrence thereof in subjects or patients. Examples of such subjects include humans as well as other mammals including, but not limited to, mouse, rat, guinea-pig, rabbit, cat, dog, sheep, goat, pig, cattle, horse, monkey, baboon, and chimpanzee, particularly a commercially important animal or a domesticated animal.

In the course of the present invention, the peptides having an amino acid sequence selected from among SEQ ID NOs: 1, 2, 3 and 4 have been found to be promiscuous Th1 cell epitopes restricted by several HLA-DR and/or HLA-DP molecules (i.e., HLA-DR4, HLA-DR53, HLA-DR15, HLA-DP2) and can be candidates that can induce potent and specific immune response against cancer due to immune responses mediated with MHC class II molecules. Therefore, the present pharmaceutical agents or compositions which include any of these peptides having the amino acid sequences of SEQ ID NOs: 1, 2, 3 or 4 are particularly suited for the administration to subjects that have at least one selected from among HLA-DR4, HLA-DR15, HLA-DR53 and HLA-DP2 as an MHC class II molecule. The same applies to pharmaceutical agents or compositions which contain polynucleotides encoding any of these peptides. Alternatively, in preferred embodiments, a peptide identified in the course of the present invention can also induce CTLs specific to KIF20A, when the peptide is applied to a subject having HLA-A2 or HLA-A24. Accordingly, through the administration of the peptide of the present invention, it is further expected that CTL response against cancer expressing KIF20A can be induced in addition to Th1 cell induction. Moreover, the peptide of the present invention can not only induce CTL response against KIF20A-expressing cells via processing thereof, but also enhance it by Th1 cell induction mediated thereby. Accordingly, in order to achieve inductions of both of Th1 cells and KIF20A-specific CTLs in the same subject, for example, the subject to be treated preferably has at least one selected from among HLA-DR4, HLA-DR15, HLA-DR53 and HLA-DP2 as a MHC class II molecule and HLA-A24 as an MHC class I molecule, when administering peptides having the amino acid sequence of SEQ ID NO: 1. Likewise, by administration of a peptide having the amino acid sequence of SEQ ID NO:2 to a subject having HLA-DR53 and/or DR15 as a MHC class II molecule and HLA-A2 as an MHC class I molecule, inductions of both of Th1 cells and KIF20A-specific CTLs can be achieved in the subject.

In another embodiment, the present invention provides an immunological cancer therapy dependent on Th1 cell induction. The therapeutic strategy provided by the present invention is applicable to and effective for any cancers independent of KIF20A expression, as long as immune cells activated by cytokines secreted from Th1 cells target objective cancer cells.

Cancers or tumors to be treated by the pharmaceutical agents or compositions of the present invention include, but are not limited and preferred examples of such cancers include any kinds of cancers or tumors expressing KIF20A, including for example, bladder cancer, breast cancer, cholangiocellular carcinoma, esophageal cancer, non-small cell lung cancer (NSCLC), pancreatic cancer, prostate cancer, renal carcinoma and small cell lung cancer (SCLC), and head-and-neck malignant tumor (HNMT).

The present pharmaceutical agents or compositions can contain in addition to the aforementioned active ingredients, other peptides that have the ability to induce Th1 cells or CTLs, other polynucleotides encoding the other peptides, other cells that present the other peptides or fragment thereof, and the like. Examples of such "other" peptides having the ability to induce Th1 cells or CTLs include, but are not limited to, peptides derived from cancer specific antigens (e.g., identified TAAs), but are not limited thereto.

If necessary, the pharmaceutical agents or compositions of the present invention can optionally include other therapeutic substances as an additional active ingredient, so long as the substance does not inhibit the antitumoral effect of the active ingredient, e.g., any of the present peptides. For example, formulations can include anti-inflammatory agents, pain killers, chemotherapeutics, and the like. In addition to including other therapeutic substances in the medicament itself, the medicaments of the present invention can also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

Those of skill in the art will recognize that, in addition to the ingredients particularly mentioned herein, the pharmaceutical agents or compositions of the present invention can include other agents conventional in the art having regard to the type of formulation in question (e.g., fillers, binders, diluents, excipients, etc.).

In one embodiment of the present invention, the present pharmaceutical agents or compositions can be included in articles of manufacture and kits containing materials useful for treating the pathological conditions of the disease to be treated, e.g., cancer. The article of manufacture can include a container of any of the present pharmaceutical agents or compositions with a label. Suitable containers include bottles, vials, and test tubes. The containers can be formed from a variety of materials, such as glass or plastic. The label on the container should indicate the agent is used for treating or prevention of one or more conditions of the disease. The label can also indicate directions for administration and so on.

In addition to the container described above, a kit including a pharmaceutical agent or composition of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical agents or compositions can, if desired, be packaged in a pack or dispenser device that can contain one or more unit dosage forms containing the active ingredient. The pack can, for example, include metal or plastic foil, such as a blister pack. The pack or dispenser device can be accompanied by instructions for administration.

(1) Pharmaceutical Agents or Compositions Containing the Peptides as the Active Ingredient The peptide of the present invention can be administered directly as a pharmaceutical agent or composition, or if necessary, that has been formulated by conventional formulation methods. In the latter case, in addition to the peptides of the present invention, carriers, excipients, and such that are ordinarily used for drugs can be included as appropriate without particular limitations. Examples of such carriers include, but are not limited to, sterilized water, physiological saline, phosphate buffer, culture fluid and such. Furthermore, the pharmaceutical agents or compositions can contain as necessary, stabilizers, suspensions, preservatives, surfactants and such. The pharmaceutical agents or compositions of the present invention can be used for anticancer purposes.

The peptides of the present invention can be prepared in a combination, composed of two or more of peptides of the present invention to induce Th1 cells in vivo. The peptide combination can take the form of a cocktail or can be conjugated to each other using standard techniques. For example, the peptides can be chemically linked or expressed as a single fusion polypeptide sequence. The peptides in the combination can be the same or different.

By administering the peptides of the present invention, the peptides or fragments thereof are presented at a high density by the HLA class II antigens on APCs, then Th1 cells that specifically react toward the complex formed between the displayed peptide and the HLA class II antigen are induced. Alternatively, APCs (e.g., DCs) are removed from subjects and then stimulated by the peptides of the present invention to obtain APCs that present any of the peptides of this invention or fragments thereof on their surface. These APCs can be readministered to the subjects to induce Th1 cells in the subjects, and as a result, aggressiveness towards the tumor-associated endothelium can be increased.

The pharmaceutical agents or compositions for the treatment and/or prevention of cancer or tumor that include a peptide of the present invention as the active ingredient can also include an adjuvant known to effectively establish cellular immunity. Alternatively, the pharmaceutical agents or compositions can be administered with other active ingredients or can be administered by formulation into granules. An adjuvant refers to a compound that enhances the immune response against the protein when administered together (or successively) with the protein having immunological activity. Adjuvants contemplated herein include those described in the literature (Clin Microbiol Rev 1994, 7: 277-89). Examples of suitable adjuvants include, but are not limited to, aluminum phosphate, aluminum hydroxide, alum, cholera toxin, *salmonella* toxin, Incomplete Freund's adjuvant (IFA), Complete Freund's adjuvant (CFA), ISCOMatrix, GM-CSF, CpG, O/W emulsion, and the like.

Furthermore, liposome formulations, granular formulations in which the peptide is bound to few-micrometers diameter beads, and formulations in which a lipid is bound to the peptide may be conveniently used.

In another embodiment of the present invention, the peptides of the present invention may also be administered in the form of a pharmaceutically acceptable salt. Examples of preferred salts include salts with an alkali metal, salts with a metal, salts with an organic base, salts with an organic acid (e.g., acetic acid, formic acid, propionic acid, fumaric acid, maleic acid, succinic acid, tartaric acid, citric acid, malic acid, oxalic acid, benzoic acid, methanesulfonic acid and so on) and salts with an inorganic acid (e.g., hydrochloric acid, phosphoric acid, hydrobromic acid, sulfuric acid and so on). As used herein, the phrase "pharmaceutically acceptable salt" refers to those salts that retain the biological effectiveness and properties of the compound and which are obtained by reaction with inorganic acids or bases such as hydrochloric acid, hydrobromic acid, sulfuric acid, nitric acid, phosphoric acid, methanesulfonic acid, ethanesulfonic acid, p-toluenesulfonic acid, salicylic acid and the like.

In some embodiments, the pharmaceutical agents or compositions of the present invention may further include a component which primes Th1 cells and optionally CTLs. Lipids have been identified as agents capable of priming Th1 cells and optionally CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of Th1 cell and optionally CTL responses, *E. coli* lipoproteins, such as tripalmitoyl-S-glycerylcysteinlyseryl-serine (P3CSS) can be used to prime Th1 cells and optionally CTLs when covalently attached to an appropriate peptide (see, e.g., Deres et al., Nature 1989, 342: 561-4).

Examples of suitable methods of administration include, but are not limited to, oral, intradermal, subcutaneous, intramuscular, intraosseous, peritoneal, and intravenous injection, or such, and systemic administration or local administration to the vicinity of the targeted sites (i.e., direct injection). The administration can be performed by single administration or boosted by multiple administrations. A pharmaceutically or therapeutically effective amount of the peptide can be administered to a subject in need of treatment of cancer expressing KIF20A. Alternatively, an amount of the peptide of the present invention sufficient to enhance or stimulate immunological response mediated with Th1 cells, and/or to induce CTLs against cancer or tumor expressing KIF20A can be administered to a subject carrying a cancer expressing KIF20A. The dose of the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, for example, 0.5 mg to 5 mg, and can be administered once in a few days to few months. One skilled in the art can readily determine suitable and optimal dosages.

(2) Pharmaceutical Agents or Compositions Containing Polynucleotides as the Active Ingredient The pharmaceutical agents or compositions of the present invention can also contain polynucleotides encoding the peptides disclosed herein in an expressible form. Herein, the phrase "in an expressible form" means that the polynucleotide, when introduced into a cell, will be expressed in vivo as a polypeptide that induces anti-tumor immunity. In an illustrative embodiment, the nucleic acid sequence of the polynucleotide of interest includes regulatory elements necessary for expression of the polynucleotide. The polynucleotide(s) can be equipped so to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922, 687).

The peptides of the present invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide into a subject can be either direct, in which case the subject is directly exposed to a polynucleotide-carrying vector, or indirect, in which case, cells are first transformed with the polynucleotide of interest in vitro, then the cells are transplanted into the subject. These two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215). Methods commonly known in the art of recombinant DNA technology which can also be used for the present invention are described in eds. Ausubel et al., Current Protocols in Molecular Biology, John Wiley & Sons, NY, 1993; and Krieger, Gene Transfer and Expression, A Laboratory Manual, Stockton Press, NY, 1990.

Like administration of peptides, administration of polynucleotides may be performed by oral, intradermal, subcutaneous, intravenous, intramuscular, intraosseous, and/or peritoneal injection, or such, and via systemic administration or local administration to the vicinity of the targeted sites finds use. The administration can be performed by single administration or boosted by multiple administrations. A pharmaceutically or therapeutically effective amount of the polynucleotide can be administered to a subject in need of treatment of cancer expressing KIF20A. Alternatively, an amount of the polynucleotide of the present invention sufficient to enhance or stimulate immunological response mediated with Th1 cells, and/or to induce CTLs against cancer or tumor expressing KIF20A can be administered to a subject carrying a cancer expressing KIF20A. The dose of the polynucleotide in the suitable carrier or cells transformed with the polynucleotide encoding the peptides of the present invention can be adjusted appropriately according to the disease to be treated, age of the patient, weight, method of administration, and such, and is ordinarily 0.001 mg to 1000 mg, for example, 0.01 mg to 100 mg, for example, 0.1 mg to 10 mg, for example, 0.5 mg to 5 mg, and can be administered once every a few days to once every few months. One skilled in the art can readily determine suitable and optimal dosages.

IX. METHODS USING THE PEPTIDES, APCs OR TH1 CELLS

The peptides of the present invention and polynucleotides encoding such peptides can be used for inducing APCs and Th1 cells of the present invention. The APCs of the present invention can be also used for inducing Th1 cells of the present invention. The peptides, polynucleotides, and APCs can be used in combination with any other compounds so long as the compounds do not inhibit their Th1 cell inducibility. Thus, any of the aforementioned pharmaceutical agents or compositions of the present invention can be used for inducing Th1 cells, and in addition thereto, those including the peptides and polynucleotides can be also used for inducing APCs as discussed below.

(1) Method of Inducing Antigen-Presenting Cells (APCs)

The present invention provides methods of inducing APCs using the peptides of the present invention or polynucleotides encoding the peptides. The induction of APCs can be performed as described above in section "VI. Antigen-presenting cells". The present invention also provides a method for inducing APCs having Th cell inducibility, the induction of which has been also mentioned under the item of "VI. Antigen-presenting cells", supra.

Alternatively, the present invention provides a method for preparing an antigen-presenting cell (APC) which has ability to induce a Th1 cell, wherein the method can include one of the following steps:

(a) contacting an APC with a peptide of the present invention in vitro, ex vivo or in vivo; and (b) introducing a polynucleotide encoding a peptide of the present invention into an APC.

Alternatively, the present invention provides methods for inducing an APC having Th1 cell inducibility, wherein the methods include the step selected from the group consisting of:

(a) contacting an APC with the peptide of the present invention, and (b) introducing the polynucleotide encoding the peptide of the present invention into an APC.

The methods of the present invention can be carried out in vitro, ex vivo or in vivo. Preferably, the methods of the present invention can be carried out in vitro or ex vivo. In preferred embodiment, APCs used for induction of APCs having Th1 cell inducibility can be preferably APCs expressing at least one selected from among HLA-DR4, HLA-DR15, HLA-DR53 and HLA-DP2 as an MHC class II molecule. Such APCs can be prepared by the methods well-known in the arts from peripheral blood mononuclear cells (PBMCs) obtained from a subject having at least one selected from among HLA-DR4, HLA-DR15, HLA-DR53 and HLA-DP2 as an MHC class II molecule. The APCs induced by the method of the present invention can be APCs that present a complex of the peptide of the present invention or fragment thereof and HLA class II antigen (e.g., HLA-DR4, HLA-DR15, HLA-DR53, HLA-DP2) on their surface. When APCs induced by the method of the present invention are administered to a subject in order to induce immune responses against cancer in the subject, the subject is preferably the same one from whom APCs are derived. However, the subject may be a different one from the APC donor so long as the subject has the same HLA type with the APC donor.

In another embodiment, the present invention provide agents or compositions for use in inducing an APC having Th1 cell inducibility, and such agents or compositions include one or more peptides or polynucleotides of the present invention.

In another embodiment, the present invention provides the use of the peptide of the present invention or the polynucleotide encoding the peptide in the manufacture of an agent or composition formulated for inducing APCs.

Alternatively, the present invention further provides the peptide of the present invention or the polypeptide encoding the peptide for use in inducing an APC having Th1 cell inducibility.

In preferred embodiments, the peptides of the present invention can induce not only Th1 response but also CTL response after processing them. Accordingly, in preferred embodiments, APCs prepared by the method of the present invention can be also useful for inducing CTLs against KIF20A expressing cells, including cancer cells. For example, when induced by the peptides containing the amino acid sequence of SEQ ID NO: 5, APCs expressing HLA-A2 are suitable for inducing KIF20A-specific CTLs. Alternatively, when induced by the peptides containing the amino acid sequence of SEQ ID NO: 6, APCs expressing HLA-A24 are suitable for inducing KIF20A-specific CTLs.

(2) Method of Inducing Th1 Cells

Furthermore, the present invention provides methods for inducing Th1 cells using the peptides of the present invention, polynucleotides encoding the peptides or APCs presenting the peptides of the present invention or fragments thereof. The present invention also provides methods for inducing Th1 cells using a polynucleotide encoding a polypeptide that is capable of forming a T cell receptor (TCR) subunit recognizing a complex of the peptides of the present invention and HLA class II antigens. Preferably, the methods for inducing Th1 cells comprise at least one step selected from the group consisting of:

a: contacting a CD4-positive T cell with an antigen-presenting cell that presents on its surface a complex of an HLA class II antigen and the peptide of the present invention or fragment thereof, and b: introducing a polynucleotide encoding both of TCR subunits or polynucleotides encoding each of TCR subunits, wherein the TCR can recognize or bind to a complex of the peptide of the present invention or fragment thereof and an HLA class II antigen, into a CD4-positive T cell.

When the peptides of the present invention are administered to a subject, Th1 cells are induced in the body of the subject, and immune responses mediated by MHC class II molecules (e.g., immune responses targeting cancer cells) are enhanced. Alternatively, the peptides and polynucleotides encoding the peptides can be used for an ex vivo therapeutic method, in which subject-derived APCs and CD4-positive cells, or peripheral blood mononuclear leukocytes are contacted (stimulated) with the peptides of the present invention in vitro, and after inducing Th1 cells, the activated Th1 cells are returned to the subject. For example, the method can include the steps of:

a: collecting APCs from subject, b: contacting the APCs of step a, with the peptide of the present invention, c: mixing the APCs of step b with CD4$^+$ T cells, and co-culturing for inducing Th1 cells: and d: collecting CD4$^+$ T cells from the co-culture of step c.

Furthermore, Th1 cells can be induced by introducing a polynucleotide encoding both of TCR subunits or polynucleotides encoding each of TCR subunits, wherein the TCR can bind to a complex of the peptide of the present invention or fragment thereof and an HLA class II antigen, into CD4-positive T cells. Such transduction can be performed as described above in section "VII. T cell receptor (TCR)".

The methods of the present invention can be carried out in vitro, ex vivo or in vivo. Preferably, the methods of the present invention can be carried out in vitro or ex vivo. CD4 positive T cells used for induction of Th1 cells can be prepared by well-known methods in the art from PBMCs obtained from a subject. In preferred embodiments, the donor for CD4-positive T cells can be a subject having at least one selected from among HLA-DR4, HLA-DR15, HLA-DR53 and HLA-DP2 as an MHC class II molecule. The Th1 cells induced by the methods of the present invention can be Th1 cells that can recognize APCs presenting a complex of the peptide of the present invention or fragment thereof and HLA class II antigen on its surface. When Th1 cells induced by the method of the present invention are administered to a subject in order to induce immune responses against cancer in the subject (or immune responses mediated by MHC class I molecules), the subject is preferably the same one from whom CD4-positive T cells are derived. However, the subject may be a different one from the CD4-positive T cell donor so long as the subject has the same HLA type with the CD4-positive T cell donor.

In preferred embodiments, the peptides of the present invention can induce CTLs against KIF20A expressing cells, as well as Th1 cells. Therefore, the present invention further provides a method for inducing a CTL, which comprises at least one step selected from the group consisting of:

a: co-culturing both of a CD4-positive T cell and a CD8-positive T cell with APCs contacted with the peptide of the present invention; and b: co-culturing a CD8-positive T cell with an APC contacted with the peptide of the present invention.

In such methods of inducing CTLs, the peptides of the present invention are processed in APCs to produce CTL epitope peptides, and produced CTL epitope peptides are presented on APC's surface.

Alternatively, according to the present invention, use of the peptides of the present invention for manufacturing a pharmaceutical agent or composition inducing Th1 cells is provided. In addition, the present invention provides a method or process for manufacturing a pharmaceutical agent or composition inducing Th1 cells, wherein the method comprises the step for admixing or formulating the peptide of the present invention with a pharmaceutically acceptable carrier. Further, the present invention also provides the peptide of the present invention for inducing Th1 cells.

The CD4$^+$ T cells induced by the method of the present invention can be administered to a subject as a vaccine.

In the context of the present invention, cancer overexpressing KIF20A can be treated with these active ingredients. Examples of such cancers include, but are not limited to, bladder cancer, breast cancer, cholangiocellular carcinoma, esophageal cancer, non-small cell lung cancer (NSCLC), pancreatic cancer, prostate cancer, renal carcinoma, small cell lung cancer (SCLC) and head-and-neck malignant tumor (HNMT). Accordingly, prior to the administration of the vaccines or pharmaceutical compositions comprising the active ingredients, it is preferable to confirm whether the expression level of KIF20A in the cancer cells or tissues to be treated is enhanced as compared with normal cells of the same organ. Thus, in one embodiment, the present invention provides a method for treating cancer (over)expressing KIF20A, which method may include the steps of:

i) determining the expression level of KIF20A in cancer cells or tissue(s) obtained from a subject with the cancer to be treated;

ii) comparing the expression level of KIF20A with normal control; and iii) administrating at least one component selected from the group consisting of (a) to (d) described above to a subject with cancer overexpressing KIF20A compared with normal control.

Alternatively, the present invention may provide a vaccine or pharmaceutical composition that includes at least one component selected from the group consisting of (a) to (d) described above, for use in administrating to a subject having cancer overexpressing KIF20A. In other words, the present invention further provides a method for identifying a subject to be treated with a KIF20A polypeptide of the present invention, such method including the step of determining an expression level of KIF20A in subject-derived cancer cells or tissue(s), wherein an increase of the level compared to a normal control level of the gene indicates that the subject has cancer which may be treated with the KIF20A polypeptide of the present invention. Methods of treating cancer of the present invention are described in more detail below.

Further, in preferred embodiments, the HLA type of a subject may be identified before administering the peptides of the present invention. For example, peptides having the amino acid sequence of SEQ ID NO: 1 are preferably administered to a subject identified as having HLA-DR4, HLA-DR15, HLA-DR53 or HLA-DP2. Alternatively, peptides having the amino acid sequence of SEQ ID NO: 2 are preferably administered to a subject identified as having HLA-DR15 or HLA-DR53. In another embodiment, peptides having the amino acid sequence of SEQ ID NO: 3 are preferably administered to a subject identified as having HLA-DR4. In some embodiments, peptides having the amino acid sequence of SEQ ID NO: 4 are preferably administered to a subject identified as having HLA-DR4 or DR53.

Any subject-derived cell or tissue can be used for the determination of KIF20A expression so long as it includes the objective transcription or translation product of KIF20A. Examples of suitable samples include, but are not limited to, bodily tissues and fluids, such as blood, sputum and urine. Preferably, the subject-derived cell or tissue sample contains a cell population including an epithelial cell, more preferably a cancerous epithelial cell or an epithelial cell derived from tissue suspected to be cancerous. Further, if necessary, the cell may be purified from the obtained bodily tissues and fluids, and then used as the subjected-derived sample.

A subject to be treated by the present method is preferably a mammal. Exemplary mammals include, but are not limited to, e.g., human, non-human primate, mouse, rat, dog, cat, horse, and cow.

According to the present invention, the expression level of KIF20A in cancer cells or tissues obtained from a subject is determined. The expression level can be determined at the transcription (nucleic acid) product level, using methods known in the art. For example, the mRNA of KIF20A may be quantified using probes by hybridization methods (e.g., Northern hybridization). The detection may be carried out on a chip or an array. The use of an array is preferable for detecting the expression level of KIF20A. Those skilled in the art can prepare such probes utilizing the sequence information of KIF20A. For example, the cDNA of KIF20A may be used as the probes. If necessary, the probes may be labeled with a suitable label, such as dyes, fluorescent substances and isotopes, and the expression level of the gene may be detected as the intensity of the hybridized labels.

Furthermore, the transcription product of KIF20A (e.g., SEQ ID NO: 10) may be quantified using primers by amplification-based detection methods (e.g., RT-PCR). Such primers may be prepared based on the available sequence information of the gene.

Specifically, a probe or primer used for the present method hybridizes under stringent, moderately stringent, or low stringent conditions to the mRNA of KIF20A. As used herein, the phrase "stringent (hybridization) conditions" refers to conditions under which a probe or primer will hybridize to its target sequence, but not to other sequences. Stringent conditions are sequence-dependent and will be different under different circumstances. Specific hybridization of longer sequences is observed at higher temperatures than shorter sequences. Generally, the temperature of a stringent condition is selected to be about 5 degree Centigrade lower than the thermal melting point (Tm) for a specific sequence at a defined ionic strength and pH. The Tm is the temperature (under a defined ionic strength, pH and nucleic acid concentration) at which 50% of the probes complementary to their target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 degree Centigrade for short probes or primers (e.g., 10 to 50 nucleotides) and at least about 60 degree Centigrade for longer probes or primers. Stringent conditions may also be achieved with the addition of destabilizing agents, such as formamide.

Alternatively, the translation product may be detected for the diagnosis of the present invention. For example, the quantity of KIF20A protein (SEQ ID NO: 11) may be determined. Methods for determining the quantity of the protein as the translation product include immunoassay methods that use an antibody specifically recognizing the protein. The antibody may be monoclonal or polyclonal. Furthermore, any fragment or modification (e.g., chimeric antibody, scFv, Fab, F(ab')$_2$, Fv, etc.) of the antibody may be used for the detection, so long as the fragment or modified antibody retains the binding ability to the KIF20A protein. Methods to prepare these kinds of antibodies for the detection of proteins are well known in the art, and any method may be employed in the present invention to prepare such antibodies and equivalents thereof.

As another method to detect the expression level of KIF20A gene based on its translation product, the intensity of staining may be measured via immunohistochemical analysis using an antibody against the KIF20A protein. Namely, in this measurement, strong staining indicates increased presence/level of the protein and, at the same time, high expression level of KIF20A gene.

The expression level of a target gene, e.g., the KIF20A gene, in cancer cells can be determined to be increased if the level increases from the control level (e.g., the level in normal cells) of the target gene by, for example, 10%, 25%, or 50%; or increases to more than 1.1 fold, more than 1.5 fold, more than 2.0 fold, more than 5.0 fold, more than 10.0 fold, or more.

The control level may be determined at the same time as the cancer cells, by using a sample(s) previously collected and stored from a subject/subjects whose disease state(s) (cancerous or non-cancerous) is/are known. In addition, normal cells obtained from non-cancerous regions of an organ that has the cancer to be treated may be used as normal control. Alternatively, the control level may be determined by a statistical method based on the results obtained by analyzing previously determined expression level(s) of KIF20A gene in samples from subjects whose disease states are known. Furthermore, the control level can be derived from a database of expression patterns from previously tested cells. Moreover, according to an aspect of the present invention, the expression level of KIF20A gene in a biological sample may be compared to multiple control levels determined from multiple reference samples. It is preferred to use a control level determined from a reference sample derived from a tissue type similar to that of the subject-derived biological sample. Moreover, it is preferred to use the standard value of the expression levels of KIF20A gene in a population with a known disease state. The standard value may be obtained by any method known in the art. For example, a range of mean+/−2 S.D. or mean+/−3 S.D. may be used as the standard value.

In the context of the present invention, a control level determined from a biological sample that is known to be non-cancerous is referred to as a "normal control level". On the other hand, if the control level is determined from a cancerous biological sample, it is referred to as a "cancerous control level". Difference between a sample expression level and a control level can be normalized to the expression level of control nucleic acids, e.g., housekeeping genes, whose expression levels are known not to differ depending on the cancerous or non-cancerous state of the cell. Exemplary control genes include, but are not limited to, beta-actin, glyceraldehyde 3 phosphate dehydrogenase, and ribosomal protein P1.

When the expression level of KIF20A gene is increased as compared to the normal control level, or is similar/equivalent to the cancerous control level, the subject may be diagnosed with cancer to be treated.

More specifically, the present invention provides a method of (i) diagnosing whether a subject has the cancer to be treated, and/or (ii) selecting a subject for cancer treatment, which method includes the steps of:

a) determining the expression level of KIF20A in cancer cells or tissue(s) obtained from a subject who is suspected to have the cancer to be treated;

b) comparing the expression level of KIF20A with a normal control level;

c) diagnosing the subject as having the cancer to be treated, if the expression level of KIF20A is increased as compared to the normal control level; and d) selecting the subject for cancer treatment, if the subject is diagnosed as having the cancer to be treated, in step c).

Alternatively, such a method includes the steps of:

a) determining the expression level of KIF20A in cancer cells or tissue(s) obtained from a subject who is suspected to have the cancer to be treated;

b) comparing the expression level of KIF20A with a cancerous control level;

c) diagnosing the subject as having the cancer to be treated, if the expression level of KIF20A is similar or equivalent to the cancerous control level; and d) selecting the subject for cancer treatment, if the subject is diagnosed as having the cancer to be treated, in step c).

In some embodiments, such a method may further comprise the step of identifying, after or before the steps a)-d) defined above, a subject having an HLA selected from the group consisting of HLA-DR4, HLA-DR15, HLA-DR53 and HLA-DP2. Cancer therapy according to the present invention is preferable for a subject that suffers from cancer overexpressing KIF20A and has any one of HLA-DR4, HLA-DR15, HLA-DR53 and HLA-DP2. Methods for HLA typing are well known in the art. For example, PCR-based methods for typing HLA alleles are well known. Antibodies specific for each HLA molecule are also appropriate tools for identifying HLA types of a subject.

The present invention also provides a kit for determining a subject suffering from cancer that can be treated with the KIF20A polypeptide of the present invention, which may also be useful in assessing and/or monitoring the efficacy of a particular cancer therapy, more particularly a cancer immunotherapy. Illustrative examples of suitable cancers include, but are not limited to, bladder cancer, breast cancer, cholangiocellular carcinoma, esophageal cancer, non-small cell lung cancer (NSCLC), pancreatic cancer, prostate cancer, renal carcinoma, small cell lung cancer (SCLC) and head-and-neck malignant tumor (HNMT). More particularly, the kit preferably includes at least one reagent for detecting the expression of the KIF20A gene in a subject-derived cancer cell, such reagent being selected from the group of:

(a) a reagent for detecting an mRNA of the KIF20A gene;
(b) a reagent for detecting the KIF20A protein; and
(c) a reagent for detecting the biological activity of the KIF20A protein.

Examples of reagents suitable for detecting an mRNA of the KIF20A gene include nucleic acids that specifically bind to or identify the KIF20A mRNA, such as oligonucleotides that have a complementary sequence to a portion of the KIF20A mRNA. These kinds of oligonucleotides are exemplified by primers and probes that are specific to the KIF20A mRNA. These kinds of oligonucleotides may be prepared based on methods well known in the art. If needed, the reagent for detecting the KIF20A mRNA may be immobilized on a solid matrix. Moreover, more than one reagent for detecting the KIF20A mRNA may be included in the kit.

On the other hand, examples of reagents suitable for detecting the KIF20A protein include antibodies to the KIF20A protein. The antibody may be monoclonal or polyclonal. Furthermore, any fragment or modification (e.g., chimeric antibody, scFv, Fab, F(ab')$_2$, Fv, etc.) of the antibody may be used as the reagent, so long as the fragment or modified antibody retains the binding ability to the KIF20A protein. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of the antibodies to their targets are well known in the art, and any labels and methods may be employed for the present invention. Moreover, more than one reagent for detecting the KIF20A protein may be included in the kit.

The kit may contain more than one of the aforementioned reagents. For example, tissue samples obtained from subjects without cancer or suffering from cancer, may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be retained in a container with a label. Suitable containers include bottles, vials, and test tubes. The containers may be formed from a variety of materials, such as glass or plastic.

As an embodiment of the present invention, when the reagent is a probe against the KIF20A mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of a test sample, the number of sites displaying a detectable signal provides a quantitative indication of the amount of KIF20A mRNA present in the sample. The detection sites may be configured in any suitably detectable shape and are typically in the shape of a bar or dot spanning the width of a test strip.

The kit of the present invention may further include a positive control sample or KIF20A standard sample. The positive control sample of the present invention may be prepared by collecting KIF20A positive samples and then assaying their KIF20A levels. Alternatively, a purified KIF20A protein or polynucleotide may be added to cells that do not express KIF20A to form the positive sample or the KIF20A standard sample. In the present invention, purified

X. ANTIBODIES

The present invention further provides antibodies that bind to the peptide of the present invention. Preferred antibodies specifically bind to the peptide of the present invention and will not bind (or will bind weakly) to other peptides. Alternatively, antibodies bind to the peptide of the invention as well as the homologs thereof. Antibodies against the peptide of the invention can find use in cancer diagnostic and prognostic assays, as well as imaging methodologies. Similarly, such antibodies can find use in the treatment, diagnosis, and/or prognosis of other cancers, to the extent KIF20A is also expressed or over-expressed in a cancer patient. Moreover, intracellularly expressed antibodies (e.g., single chain antibodies) may therapeutically find use in treating cancers in which the expression of KIF20A is involved, examples of which include, but are not limited to, bladder cancer, breast cancer, cholangiocellular carcinoma, esophageal cancer, non-small cell lung cancer (NSCLC), pancreatic cancer, prostate cancer, renal carcinoma, small cell lung cancer (SCLC) and head-and-neck malignant tumor (HNMT).

The present invention also provides various immunological assay for the detection and/or quantification of KIF20A protein (SEQ ID NO: 11) or fragments thereof including a polypeptide composed of amino acid sequences selected from among SEQ ID NOs: 1, 2, 3 and 4. Such assays may include one or more anti-KIF20A antibodies capable of recognizing and binding a KIF20A protein or fragments thereof, as appropriate. In the present invention, anti-KIF20A antibodies binding to KIF20A polypeptide preferably recognize a polypeptide composed of amino acid sequences selected from among SEQ ID NOs: 1, 2, 3 and 4, preferably to the exclusion of other peptides. The binding specificity of antibody can be confirmed with inhibition test. That is, when the binding between an antibody to be analyzed and full-length of KIF20A polypeptide is inhibited under presence of any fragment polypeptides having a amino acid sequence selected from among SEQ ID NOs: 1, 2, 3 and 4, the antibody is deemed to "specifically bind" the fragment. In the context of the present invention, such immunological assays are performed within various immunological assay formats well known in the art, including but not limited to, various types of radio-immunoassays, immuno-chromatograph technique, enzyme-linked immunosorbent assays (ELISA), enzyme-linked immunofluorescent assays (ELIFA), and the like.

Related immunological but non-antibody assays of the invention may also include T cell immunogenicity assays (inhibitory or stimulatory) as well as MHC binding assays. In addition, immunological imaging methods capable of detecting cancers expressing KIF20A are also provided by the invention, including, but not limited to, radioscintigraphic imaging methods using labeled antibodies of the present invention. Such assays can clinically find use in the detection, monitoring, and prognosis of KIF20A expressing cancers, examples of which include, but are not limited to, bladder cancer, breast cancer, cholangiocellular carcinoma, esophageal cancer, non-small cell lung cancer (NSCLC), pancreatic cancer, prostate cancer, renal carcinoma, small cell lung cancer (SCLC) and head-and-neck malignant tumor (HNMT).

The present invention also provides antibodies that bind to a peptide of the invention. An antibody of the invention can be used in any form, such as monoclonal or polyclonal antibodies, and include antiserum obtained by immunizing an animal such as a rabbit with the peptide of the invention, all classes of polyclonal and monoclonal antibodies, human antibodies and humanized antibodies produced by genetic recombination.

A peptide of the invention used as an antigen to obtain an antibody may be derived from any animal species, but preferably is derived from a mammal such as a human, mouse, or rat, more preferably from a human. A human-derived peptide may be obtained from the nucleotide or amino acid sequences disclosed herein.

According to the present invention, complete and partial peptides of polypeptide of the present invention may serve as immunization antigens. Examples of suitable partial peptide include, for example, the amino (N)-terminal or carboxy (C)-terminal fragment of a peptide of the present invention.

Herein, an antibody is defined as a protein that reacts with either the full length or a fragment of a KIF20A peptide. In a preferred embodiment, antibody of the present invention can recognize fragment peptides of KIF20A having an amino acid sequence selected from among SEQ ID NOs: 1, 2, 3 and 4. Methods for synthesizing oligopeptide are well known in the arts. After the synthesis, peptides may be optionally purified prior to use as immunogen. In the present invention, the oligopeptide (e.g., 21-, 24, or 25 mer) may be conjugated or linked with carriers to enhance the immunogenicity. Keyhole-limpet hemocyanin (KLH) is well known as the carrier. Method for conjugating KLH and peptide are also well known in the arts.

Alternatively, a gene encoding a peptide of the invention or fragment thereof may be inserted into a known expression vector, which is then used to transform a host cell as described herein. The desired peptide or fragment thereof may be recovered from the outside or inside of host cells by any standard method, and may subsequently be used as an antigen. Alternatively, whole cells expressing the peptide or their lysates or a chemically synthesized peptide may be used as the antigen.

Any mammalian animal may be immunized with the antigen, though preferably the compatibility with parental cells used for cell fusion is taken into account. In general, animals of Rodentia, Lagomorpha or Primate family may be used. Animals of the family Rodentia include, for example, mouse, rat and hamster. Animals of the family Lagomorpha include, for example, rabbit. Animals of the Primate family include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum may be examined by a standard method for an increase in the amount of desired antibodies.

Polyclonal antibodies against the peptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the peptide of the present invention using, for example, an affinity column coupled with the peptide of the present invention, and further purifying this fraction using protein A or protein G column.

To prepare monoclonal antibodies for use in the context of the present invention, immune cells are collected from the mammal immunized with the antigen and checked for the increased level of desired antibodies in the serum as described above, and are subjected to cell fusion. The immune cells used for cell fusion may preferably be obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution may be performed to screen and clone a hybridoma cell producing the desired antibody.

In addition to the above method, wherein a non-human animal is immunized with an antigen for preparing hybridoma, human lymphocytes such as those infected by EB virus may be immunized with a peptide, peptide expressing cells or their lysates in vitro. Then, the immunized lymphocytes may be fused with human-derived myeloma cells that are capable of indefinitely dividing, such as U266, to yield a hybridoma producing a desired human antibody that is able to bind to the peptide can be obtained (Unexamined Published Japanese Patent Application No. Sho 63-17688).

The obtained hybridomas may then be subsequently transplanted into the abdominal cavity of a mouse and the ascites extracted. The obtained monoclonal antibodies can be purified by, for example, ammonium sulfate precipitation, a protein A or protein G column, DEAE ion exchange chromatography or an affinity column to which the peptide of the present invention is coupled. An antibody of the present invention can be used not only for purification and detection of a peptide of the present invention, but also as a candidate for agonists and antagonists of a peptide of the present invention.

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides for recombinant antibodies prepared as described above.

An antibody of the present invention may be a fragment of an antibody or modified antibody, so long as it binds to one or more of the peptides of the invention. For instance, the antibody fragment may be Fab, $F(ab')_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, including the complementarity determining region (CDR) derived from nonhuman antibody, the frame work region (FR) and the constant region derived from human antibody. Such antibodies can be prepared according to known technology. Humanization can be performed by substituting rodent CDRs or CDR sequences for the corresponding sequences of a human antibody (see, e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies including human variable regions in addition to human framework and constant regions can also be used. Such antibodies can be produced using various techniques known in the art. For example, in vitro methods involve use of recombinant libraries of human antibody fragments displayed on bacteriophage (e.g., Hoogenboom & Winter, J. Mol. Biol. 227:381 (1991). Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to the separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F.F. (Pharmacia).

Examples of suitable chromatography techniques, with the exception of affinity chromatography, include, for example, ion-exchange chromatography, hydrophobic chromatography, gel filtration, reverse phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence may be used to measure the antigen binding activity of the antibody of the invention. In ELISA, the antibody of the present invention is immobilized on a plate, a peptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the peptide, such as a C-terminal or N-terminal fragment, may be used as the antigen to evaluate the binding activity of the antibody. BIAcore (Pharmacia) may be used to evaluate the activity of the antibody according to the present invention.

The above methods allow for the detection or measurement of the peptide of the invention, by exposing the antibody of the invention to a sample assumed to contain the peptide of the invention, and detecting or measuring the immune complex formed by the antibody and the peptide.

Because the method of detection or measurement of the peptide according to the invention can specifically detect or measure a peptide, the method can find use in a variety of experiments in which the peptide is used.

XI. VECTORS AND HOST CELLS

The present invention also provides for vectors and host cells into which a nucleotide encoding the peptide of a present invention is introduced. A vector of the present invention finds utility as a carrier of nucleotides, especially a DNA, of the present invention in host cell, to express the peptide of the present invention, or to administer the nucleotide of the present invention for gene therapy.

When E. coli is selected as the host cell and the vector is amplified and produced in a large amount in E. coli (e.g., JM109, DH5 alpha, HB101 or XL1Blue), the vector should have an "ori" suitable for amplification in E. coli and a marker gene suited for selecting transformed E. coli (e.g., a drug-resistance gene selected by a drug such as ampicillin, tetracycline, kanamycin, chloramphenicol or the like). For example, M13-series vectors, pUC-series vectors, pBR322, pBluescript, pCR-Script, etc., can be used. In addition, pGEM-T, pDIRECT and pT7 can also be used for subcloning and extracting cDNA as well as the vectors described above. When a vector is used to produce the protein of the present invention, an expression vector can find use. For example, an expression vector to be expressed in E. coli should have the above characteristics to be amplified in E. coli. When E. coli, such as JM109, DH5 alpha, HB101 or XL1 Blue, are used as a host cell, the vector should have a promoter, for example, lacZ promoter (Ward et al., Nature 341: 544-6 (1989); FASEB J 6: 2422-7 (1992)), araB promoter (Better et al., Science 240: 1041-3 (1988)), T7 promoter or the like, that can efficiently express the desired gene in E. coli. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may also contain a signal sequence for peptide secretion. An exemplary signal sequence that directs the peptide to be secreted to the periplasm of the E. coli is the pelB signal sequence (Lei et al., J Bacteriol 169: 4379 (1987)). Means for introducing of the vectors into the target host cells include, for example, the calcium chloride method, and the electroporation method.

In addition to E. coli, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01) and expression vectors derived from Bacillus subtilis (e.g., pPL608, pKTH50) can be used for producing the polypeptide of the present invention.

In order to express the vector in animal cells, such as CHO, COS or NIH3T3 cells, the vector should carry a promoter necessary for expression in such cells, for example, the SV40 promoter (Mulligan et al., Nature 277: 108 (1979)), the MMLV-LTR promoter, the EF1 alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Hereinafter, the present invention is described in more detail with reference to specific Examples. However, while the following materials, methods and examples may serve to assist one of ordinary skill in making and using certain embodiments of the present invention, there are only intended to illustrate aspects of the present invention and thus in no way to limit the scope of the present invention. As one of ordinary skill in the art will readily recognize, methods and materials similar or equivalent to those described herein can be used in the practice or testing of the present invention.

Examples

Materials and Methods

Cell Lines and Antibodies.
The TAP-deficient and HLA-A2-positive cell line T2 were purchased from Riken Cell Bank. C1R-A2402 cells, an HLA-A24 transfectant of human B lymphoblastoid cell line C1R expressing a trace amount of intrinsic HLA class I molecule (Karaki S, et al. Immunogenetics 1993; 37: 139-42.), were a generous gift from Dr. Masafumi Takiguchi (Kumamoto University, Kumamoto, Japan). As antigen presenting cells (APCs), a mouse fibroblast cell line, L-cell, which have genetically been engineered to express either DR4 (DRB1*04:05); L-DR4, DR8 (DRB1*08:03); L-DR8, DR15 (DRB1*15:02); L-DR15 or DR53 (DRB4*01:03); L-DR53 were used.

Prediction by an algorithm of HLA class II-binding peptides To predict potential promiscuous HLA-DR binding human KIF20A-derived peptides, the amino acid sequence of the human KIF20A protein was analyzed using a computer algorithm (IEBD analysis resource, consensus method, tools.immuneepitope.org/analyze/html/mhc_II binding.html) (Wang P, et al. BMC Bioinformatics; 11: 568.; Wang P, et al. PLoS Comput Biol 2008; 4: e1000048.). The program analyzed 15 amino acid-long sequences offset encompassing the entire protein. The 25 amino acids-long two peptides that have overlapping high consensus percentile ranks for multiple HLA-class II molecules encoded for by DRB1*04:05, DRB1*15:02, or DRB4*01:03 alleles, and that naturally include KIF20A-derived 9 or 10-mer CTL epitopes were selected and synthesized to identify promiscuous helper T cell epitopes containing CTL epitopes (Imai K, et al. Br J Cancer; 104: 300-7.). The other two KIF20A-derived LPs that don't include CTL epitopes were also synthesized.

Synthetic Peptides and Recombinant Proteins.

Two human KIF20A-derived short peptides (SPs), KIF20A-A2 (809-817), CIAEQYHTV (SEQ ID NO: 5) and KIF20A-A24 (66-75), KVYLRVRPLL (SEQ ID NO: 6) were synthesized (purity>95%, Biomatik, Canada), because the inventors have already published that these two peptides could induce tumor-reactive and HLA-A2(A*0201)- or HLA-A24(A*2403)-restricted human CTLs respectively. Four LPs, KIF20A (60-84), DSMEKVKVYLRVRPLL-PSELERQED (SEQ ID NO: 1); KIF20A (494-517) TLH-VAKFSAIASQLVHAPPMQLGF (SEQ ID NO: 3); KIF20A (809-833), CIAEQYHTVLKLQGQVSAKKRLGTN (SEQ ID NO: 2); KIF20A (843-863), PPGKKPFLRNLLPRTPTC-QSS (SEQ ID NO: 4), were synthesized (purity>90%) and tested for their capacity to stimulate KIF20A-specific human CD4+ T cells in vitro. Two HIV peptides that were reported to bind to HLA-A24 (HIV-A24, RYLRDQQLL) (SEQ ID NO: 7) and HLA-A2 (HIV-A2, SLYNTYATL) (SEQ ID NO: 8), were used as negative control SPs (Tomita Y, et al., Cancer Sci; 102: 697-705; Tomita Y, et al., Cancer Sci; 102: 71-8.). A LP, a WT1-derived peptide (KRYFKLSHLQMH-SRKH) (SEQ ID NO: 9) that can induce HLA-DR4 (DRB1*0405)-restricted Th1 cells, (Fujiki F, et al., J Immunother 2007; 30: 282-93.) was used as a negative control LP.

Peptides were dissolved in dimethylsulfoxide at the concentration of 10 micro-g/micro-L or 20 micro-g/micro-L.

The 6His-tagged recombinant whole KIF20A protein and CDCA1 protein were expressed by E. coli BL21 strains with a pET28a vector (Novagen) harboring the respective cDNA fragments. The CDCA1 protein was used as control protein. Each recombinant protein was purified using a HisTrap FF column (GE Healthcare) according to the manufacturer's instruction. The purity of the proteins was verified by SDS-PAGE.

Generation of TAAs-Specific CD4+ T Cell Lines and Clones.

The research protocol for collecting and using peripheral blood mononuclear cells (PBMC) from healthy donors was approved by the Institutional Review Board of Kumamoto University. The blood samples were obtained from six healthy donors after receiving their written informed consents. The HLA-A, DRB1 and DPB1 alleles of the healthy donors investigated in this study are determined by DNA typing of HLA alleles using polymerase chain reaction and allele-specific probe hybridization, and described in Table 1. PBMCs from healthy volunteers were isolated as described previously (Inoue M, et al. Int J Cancer; 127: 1393-403.). CD4+ T cells were purified from PBMC by positive selection using magnetic microbeads coupled with anti-CD4 monoclonal antibody (Miltenyi Biotec, Auburn, Calif., USA). Monocyte-derived dendritic cell (DC) was generated from CD14+ cells by in vitro culture as described previously (Harao M, et al. Int J Cancer 2008; 123: 2616-25.) and used as antigen-presenting cell (APC) to induce TAA-specific CD4+ T cells. DCs ($1\times10^4$/well) were pulsed with 10 micro-g/ml LP for 3 h and irradiated (45 Gy), and then mixed with autologous CD4+ T cells ($3\times10^4$/well) in 200 micro-L of AIM-V supplemented with 5% human decomplemented plasma in each well of a 96-well, flat-bottomed culture plates. After 7 days, half of the medium was removed from each culture, and then the fresh medium (100 micro-L/well) containing irradiated (50 Gy) autologous PBMCs ($1\times10^5$) pulsed with peptide (10 micro-g/ml) and 5 ng/ml human recombinant (hr) IL-7 were added to the culture. Two days after the second stimulation with peptide, hr IL-2 was added to each well at final concentration of 10 IU/ml. One week later, the stimulated CD4+ T cells in each well were analyzed for their peptide-specificity in interferon (IFN)-gamma enzyme-linked immunospot (ELISPOT) assays. The T cells showing a specific response to the cognate peptide were transferred to 24-well plate and re-stimulated at weekly intervals with irradiated autologous PBMCs ($1\times10^6$/well) pulsed with the peptide (10 micro-g/ml) in medium supplemented with 10 IU/ml hr IL-2 and 5 ng/ml hr IL-7. In some instances, T cells were cloned by limiting dilution for further studies as described previously (Tabata H, et al. Hum Immunol 1998; 59: 549-60.).

TABLE 1

HLA-A-DR and DP genotypes of healthy donors

| | HLA-A genotype | HLA-DRB1 genotype | HLA-DPB1 genotype |
|---|---|---|---|
| Donor HDK1 | A*02:01/ | DRB1*04:05/09:01/DRB4*01:03 | DPB1*02:01/DPB1*04:02 |
| Donor HDK2 | A*11:01/31:01 | DRB1*08:03/15:02 | DPB1*02:01/09:01 |
| Donor HDK3 | A*02:06/31:01 | DRB1*04:01/09:01/DRB4*01:03 | DPB1*02:01/ |
| Donor HDK4 | A*02:01/24:02 | DRB1*04:05/DRB4*01:03 | DPB1*05:01/ |
| Donor HDK5 | A*24:02/ | DRB1*08:02/15:02 | DPB1*05:01/09:01 |
| Donor HDK6 | A*02:01/24:02 | DRB1*09:01/12:01/DRB4*01:03 | DPB1*03:01/06:01 |
| Donor HDK7 | n.t. | DRB1*04:06/08:03/DRB4*01:03 | DPB1*02:01/04:02 |
| Donor HDK8 | A*24:02/31:01 | DRB1*08:03/14:05 | DPB1*02:02/05:01 |

TABLE 1-continued

HLA-A-DR and DP genotypes of healthy donors

| | HLA-A genotype | HLA-DRB1 genotype | HLA-DPB1 genotype |
|---|---|---|---|
| Donor HDK9 | A*26:01/33:03 | DRB1*04:05/13:02/DRB4*01:03 | DPB1*04:01/09:01 |
| Donor HDK10 | A*26:01/— | DRB1*04:10/08:02/DRB4*01:03 | DPB1*02:01/05:01 |
| Donor HDK11 | A*31:01/33:03 | DRB1*09:01/13:02/DRB4*01:03 | DPB1*03:01/4:01 |

PBMCs derived from healthy donors (HDK1, HDK2, HDK4, HDK5, HDK7, HDK8, HDK9, HDK10 and HDK11) were used as a control in FIG. 8B.
HLA, human leukocyte antigen.;
n.t., not tested Patients Blood samples were collected from 16 patients with a head and neck malignant tumor (HNMT). The immune responses of Th cells reactive to KIF20A-LPs were investigated. The patients were receiving immunotherapy with TAA-derived CTL-epitope peptides, and were enrolled in 2 peptide vaccine trials. These phase I/II clinical trials of cancer immunotherapy using 3 HLA-A24-binding short peptides (SPs), (clinical-grade 9-10-amino acid-long peptides) derived from 3 cancer-testis antigens, LY6K (LY6K-A24(177-186)), IMP-3 (IMP-3-A24(508-516)), and CDCA1 (CDCA1-A24(56-64)) were reviewed and approved by the Institutional Review Board of Kumamoto University, Japan (Kono K et al. J Transl Med 2012; 10:141., Suda T et al. Cancer Sci 2007; 10:1803-8., Harao M et al. Int J Cancer 2008; 123:2616-25.). This vaccine cocktail did not include KIF20A-derived SPs. All patients with HNMT were selected on the basis of HLA-A24 presence after providing written informed consent. The patients suffered from inoperable advanced HNMT with recurrent or metastatic tumors and were resistant to standard therapy; they were enrolled in the trial under University Hospital Medical Information Network Clinical Trials Registry (UMIN-CTR) number 000008379 (CTR-8379). The patients with radical resection were enrolled in the trial under UMIN-CTR number 000008380 (CTR-8380). In the latter trial, patients were treated with postoperative peptide vaccine combined with S-1, ifosfamide, or doxorubicin. These clinical trials and analyses are ongoing.

Assessment of T Cell Responses to Peptides and Proteins.

The immune response of Th cells to APCs pulsed with peptides and proteins were assessed by IFN-gamma ELISPOT assays (Human IFN-gamma ELISPOT kit, BD Biosciences) as described previously (Tomita Y, et al. Cancer Sci; 102: 697-705.). Briefly, the frequency of peptide-specific CD4$^+$ T cells producing IFN-gamma per $3\times10^4$ bulk CD4$^+$ T cells upon stimulation with peptide-pulsed PBMCs ($3\times10^4$), or $1\times10^4$ bulk CD4$^+$ T cells upon stimulation with peptide-pulsed L-cells ($5\times10^4$/well) expressing HLA-DR was analyzed. The frequency of cells producing IFN-gamma per $1\times10^5$ CTLs upon stimulation with peptide-pulsed T2 cells ($2\times10^4$/well) or C1R-A2402 cells ($2\times10^4$/well) was also analyzed. Alternatively, $5\times10^3$ protein-loaded DCs were co-cultured with $2\times10^4$ CD4$^+$ T cell clones/well. The protein-loaded mature DCs were prepared from positively isolated CD14$^+$ cells (day 0) as described previously (Harao M, et al. Int J Cancer 2008; 123: 2616-25.). On day 5, the DCs were cultured in the presence of the recombinant KIF20A (50 micro-g/ml) and OK432. The protein-loaded mature DCs were harvested on day 7, washed and used as stimulator in IFN-gamma ELISPOT assays. To determine restriction HLA molecules involved in antigen presentation, blocking of antigen-induced IFN-gamma production was investigated by adding anti-HLA-DR mAb (L243, Biolegend), anti-HLA-DP mAb, (B7/21, abcam), anti-human HLA-DQ mAb (SPV-L3, abcam), or anti-HLA class I mAb, (W6/32, abcam). All mAbs were used at a final concentration of 5 micro g/ml. All assessments of IFN-gamma ELISPOT assays were carried out in duplicate or triplicate, and results corresponded to mean values.

Immunohistochemical Examination

Immunohistochemical staining of KIF20A using a rabbit polyclonal antibody against KIF20A (A300-879A, Bethyl Laboratories, Montgomery, Tex., USA) was performed as described previously (Imai K et al. Br J Cancer 2011; 104:300-7. Yamashita J et al. Acta Derm Venereol 2012; 92:593-7. Yoshitake Y, et al. Clin Cancer Res 2004; 10:6437-48.).

Cytokine Assays

T cells ($1\times10^4$/well) were cultured with autologous PBMC ($3\times10^4$/well) in the presence of KIF20A (60-84) or L-DR53 ($5\times10^4$) in the presence of KIF20A (809-833) in 96-well culture plate. After 20 h, culture supernatants were collected and cytokine (IFN-gamma, TNF-alpha, GM-CSF, MIP1beta, IL-2, IL-4 and IL-17) level was measured using the Bio-Plex system (Bio-Rad) according to manufacturers' instructions.

CD107a Mobilization Assay.

To identify degranulating CD4$^+$ T lymphocytes stimulated with the peptides, the CD107a exposed on the cell surface was analyzed by flow cytometry. (Rubio V, et al. Nat Med 2003; 9: 1377-82.; Betts M R, et al. J Immunol Methods 2003; 281: 65-78.) Briefly, a CD107a mobilization assay was performed as described previously. (Tomita Y, et al. Cancer Sci.) The KIF20A-derived peptide or control peptide (1 micro-g/ml) was added as a stimulant, and FITC-labeled anti-human CD107a mAb or FITC-labeled isotype control mouse IgG1 and monensin were added to each well. Cells were cultured for 5 h at 37 degrees C. After culture, the peptide-stimulated Th cells were stained with PE-conjugated anti-human CD4 antibody (eBioscience, San Diego, Calif.), and analyzed by flow cytometry (FACScan; BD Biosciences).

The Synergistic Effect of KIF20A-LPs on Induction of KIF20A-Specific CTLs

PBMCs obtained from an HLA-A2$^+$/DR53$^+$/DP2$^+$ donor (HD1), from whom the KIF20A (60-84) LP or KIF20A (809-833) LP-specific Th-clones were generated, were plated in 24-well plates ($3\times10^6$ cells/well). After culture for 7 days the following additions were made: recombinant human (rh) IL-2 (20 U/mL) and SP alone (KIF20A-A2 (809-817) SP, 20 micro g/mL), or SP+LP (KIF20A (60-84) LP or KIF20A (809-833) LP, 20 micro g/mL), or SP+LP+ Th-clone ($5\times10^5$ cells/well) in a final volume of 2 mL. Recombinant human IL-15 (5 ng/mL) was added on day 9. On day 11, cells were stained with PE-labeled tetramer of the HLA-A*02:01/KIF20A-A2 (809-817)-complex and an FITC-labeled anti-human CD8 mAb. Data acquisition was performed on a FACSCalibur (BD Biosciences), and data files were analyzed with FlowJo software (Tree Star, Ashland, Oreg.).

Stimulation of PBMC with the KIF20A Long Peptide

To assess the induction of KIF20A-A24 (66-75) SP-specific CTLs from HLA-A24-positive donors by the simulation with KIF20A (60-84) LP in vitro, PBMC ($2\times10^6$/well of 24-well plates) were incubated with KIF20A-derived LPs (7 micro-M) for 2 weeks without addition of any cytokine. On day 0 and 7, KIF20A-derived LPs (7 micro-M) was added, then on day 14 of in vitro stimulation with LPs, the cells were harvested, stained with a PE-labeled tetramer of the HLA-A*24:02/KIF20A-A24 (66-75) peptide complex in combination with a FITC-labeled anti-human CD8 mAb, and analyzed by flow cytometry.

In Vitro Stimulation of KIF20A-A2 (809-817) SP-Specific CTLs by KIF20A (809-833) LP To assess the stimulation of KIF20A-A2 (809-817) SP reactive CTLs in vitro by KIF20A (809-833) LP, the number of IFN-gamma producing KIF20A-A2 (809-817) SP-specific bulk CTL upon stimulation with the KIF20A (809-833) LP or a irrelevant LP-loaded DCs isolated from a HLA-A2-positive donor was counted by an ELISPOT assay. The induction of KIF20A-A2 (809-817) SP-reactive human CTLs in vitro was performed as reported previously (Tomita Y, et al. Cancer Sci; 102: 71-8.). The LP-loaded mature DCs were prepared from positively isolated CD14$^+$ cells (day 0). CD14$^+$ cells were cultured in the presence of hr IL4 (10 ng/ml) and GM-CSF (100 ng/ml). KIF20A (809-833) LP (50 micro-g/ml) and OK432 were added on day 5. The LP-loaded mature DCs were harvested on day 7, washed and used as APCs in an ELISPOT assay.

Assessment of KIF20A-LPs-Specific CD4$^+$ T-Cell Responses in Patients with HNMT.

Fresh PBMCs from patients with HNMT or healthy donors were cultured with a mixture of KIF20A (60-84) LP and KIF20A (809-833) LP (10 micro g/mL each) in a final volume of 2 ml AIM-V supplemented with 5% human decomplemented plasma at 37 degrees C. ($2\times10^6$ cells/well, 24-well plates); both rhIL-2 and rhIL-7 were added on day 0 and 2. After 1 week of cell culture, the PBMCs were collected, washed, and cultured in ELISPOT plates ($1\times10^5$ cells/well) with KIF20A (60-84) LP, KIF20A (809-833) LP, or control LP for 18 h. The number of KIF20A-LP-specific Th cells expressed as spot-forming cells/$10^5$ cells was calculated after subtracting control values (background). Responses were scored as positive when the mean number of IFN-gamma spots was more than 15 and more than 2-fold over background. The ELISPOT assays on patients' cells were conducted in single, duplicate, or triplicate wells because of the limited number of available cells.

This study was conducted in a laboratory that operates under exploratory research principles, and was performed using investigative protocols. The present inventors acknowledge the recommendations of the Minimal Information About T-cell Assays (MIATA) reporting framework for human T-cell assays (Britten C M, et al. Immunity 2012; 37:1-2.).

Statistical Analysis

The data were compared by the Two-tailed Student's t-test (bar graphs) or by the nonparametric Mann-Whitney U test (scatter-dot graph). Differences with a P value of <0.05 were considered statistically significant for all tests.

Results

Prediction and Selection of Potential Promiscuous HLA Class II-Binding Peptides Containing CTL Epitopes of KIF20A To identify the potential promiscuous HLA-class II binding Th cell epitopes of KIF20A, the present inventors first examined the amino acid sequence of KIF20A by using a computer algorithm as shown in FIG. 1A and Table 2 (Wang P, et al. BMC Bioinformatics; 11: 568.14.; Wang P, et al. PLoS Comput Biol 2008; 4: e1000048.). Interestingly, it was found that two regions (KIF20A (60-84) and KIF20A (809-833)) of KIF20A protein sequence were predicted to be potent promiscuous HLA class II-binding peptides by the computer algorithm, and both of them were very proximal to the CTL epitopes (FIG. 1B). Therefore, the inventors selected and synthesized two candidate LPs (KIF20A (60-84) and KIF20A (809-833)) that have overlapping high consensus percentile ranks for multiple and frequent HLA-class II molecules HLA-DR4, HLA-DR15 and HLA-DR53, and include natural 9 or 10-mer peptides recognized by HLA-A2- or -A24-restricted CTLs for subsequent analyses. The other two LPs, KIF20A (494-517) and KIF20A (843-863) were also synthesized that don't include CTL epitopes but have overlapping high consensus percentile ranks for multiple HLA-class II molecules, and assessed whether these LPs were able to generate KIF20A-specific Th cells.

TABLE 2

Algorithm scores of long peptides derived from KIF20A

| Amino acid | Consensus Percentile Rank | | |
|---|---|---|---|
| residues position | HLA-DR4 (DRB1*04:05) | HLA-DR15 (DRB1*15:02) | HLA-DR53 (DRB4*01:03) |
| 60-74 | 14.9 | 1.8 | 12.8 |
| 61-75 | 14.9 | 1.8 | 6.4 |
| 62-76 | 4.2 | 1.8 | 2.9 |
| 63-77 | 4.2 | 1.1 | 1.2 |
| 64-78 | 4.2 | 1.1 | 0.8 |
| 65-79 | 2.3 | 1.1 | 0.5 |
| 66-80 | 2.4 | 1.1 | 0.7 |
| 67-81 | 5.7 | 1.1 | 2.1 |
| 68-82 | 5.7 | 1.1 | 4.6 |
| 69-83 | 9.5 | 1.1 | 21.3 |
| 70-84 | 19.4 | 3.3 | 42.6 |
| 809-823 | 13.8 | 6.7 | 16 |
| 810-824 | 13.8 | 6.7 | 10.8 |
| 811-825 | 11.2 | 6.7 | 3.2 |
| 812-826 | 11.2 | 6.7 | 1.6 |
| 813-827 | 13.5 | 6.7 | 1.4 |
| 814-828 | 12.1 | 6.7 | 1.2 |
| 815-829 | 16.8 | 15.1 | 1.4 |
| 816-830 | 21.3 | 15.1 | 2.2 |
| 817-831 | 21.9 | 15.1 | 3.7 |
| 818-832 | 25.4 | 12.6 | 11.6 |
| 819-833 | 46.1 | 12.6 | 36.1 |

Pepide-binding algorithm scores for indicated HLA-class II genotypes are shown for each 15 amino acid sequence of KIF20A peptide (60-84) and KIF20A (809-833). Identification of KIF20A-derived and promiscuous HLA class II-binding Th cell epitopes naturally including CTL epitopes.

The present inventors assessed whether these four selected synthetic LPs were able to generate KIF20A-specific Th cells. CD4$^+$ T cells isolated from PBMCs of three healthy donors were stimulated at weekly intervals with autologous DCs and PBMCs pulsed with KIF20A (60-84) peptide. After at least three times stimulations, KIF20A (60-84)-specific responses of the cultured CD4$^+$ Th cells were examined by IFN-gamma ELISPOT assays. In an HLA-DP2 (DP*02:01)-positive healthy donor, the generated Th cell line produced a significant amount of IFN-gamma in response to KIF20A (60-84) (FIG. 2A). To elucidate HLA-restriction of the Th cell lines, the inventors used mAb against HLA-DR or HLA-DP. The IFN-gamma production of Th cell line against KIF20A (60-84) was significantly reduced when HLA-DP-specific mAb was added, whereas HLA-DR-specific mAb showed no effect.

To further analyze the HLA-restriction, KIF20A (60-84)-specific clone was obtained by limiting dilution of this DP-restricted bulk CD4+ Th cell line from the donor HDK1. The inventors used allogeneic PBMCs from four different donors as APCs to determine shared restriction HLA-DP molecules in IFN-gamma ELISPOT assays. Consequently, the KIF20A (60-84)-specific clone showed specific response to KIF20A (60-84) peptide only in the presence of DP2-expressing allogeneic PBMCs in IFN-gamma ELISPOT assays, and the IFN-gamma production was significantly inhibited by addition of anti-HLA-DP mAb, but not the HLA-DR-specific mAb. These results suggest that the DP-restricted Th cell line derived from the donor HDK1 is restricted by HLA-DP2 (FIG. 2B).

To investigate whether KIF20A (60-84) can bind other HLA class II molecules and induce Th cell responses, CD4+ T cells from other two healthy donors were stimulated with KIF20A (60-84)-pulsed autologous DCs and PBMCs. The Th cell line generated from an HLA-DR15-positive donor specifically produced a significant amount of IFN-gamma in response to KIF20A (60-84)-pulsed PBMCs and L-DR15 cells, but not peptide-unpulsed PBMC or KIF20A (60-84)-pulsed L-DR8 cells. The IFN-gamma production of Th cell line against PBMCs or L-DR15 cells pulsed with the KIF20A (60-84) LP were significantly inhibited by addition of anti-HLA-DR mAb, but not the HLA-DP- or HLA-class I-specific mAbs (FIGS. 2A and B). These results clearly indicate that KIF20A (60-84) was presented by HLA-DR15 as well as HLA-DP2 in this T cell line. The inventors also tried to induce KIF20A (60-84)-specific Th cells from an donor negative for both HLA-DP2 and HLA-DR15. Consequently, the present inventors were able to induce KIF20A (60-84) specific and HLA-DR-restricted Th cells. Thus, the KIF20A (60-84) has capability of binding to HLA-DP2 and two different HLA-DR molecules suggesting that KIF20A (60-84) is the Th cell epitope presented by promiscuous and frequent HLA class II molecules in the Japanese population.

Figure 2C:
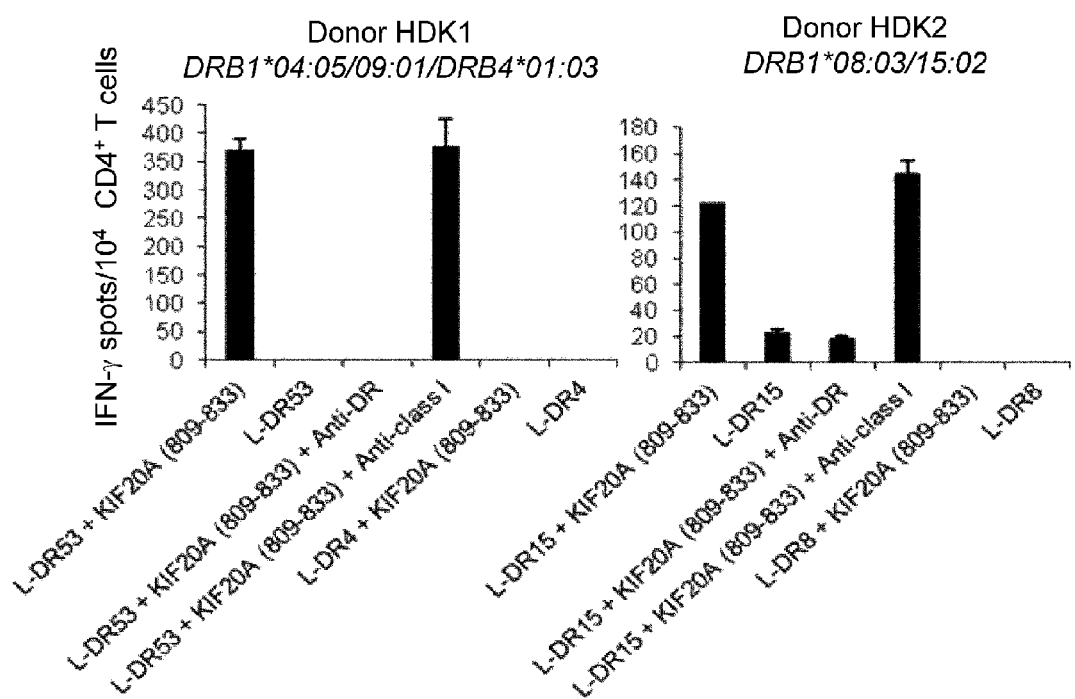
[FIG. 2C] In part C, a KIF20A (809-833)-specific CD4$^+$ T cell line derived from an HLA-DR53-positive donor HDK1 were co-cultured with L-DR53 pulsed or unpulsed with KIF20A (809-833), L-DR53 pulsed with KIF20A (809-833) in the presence of anti-HLA-DR or anti-HLA class I-blocking mAb, or L-DR4 pulsed or unpulsed with KIF20A (809-833) (left panel). KIF20A (809-833)-specific CD4$^+$ T line derived from an HLA-DR15-positive donor HDK2 were co-cultured with L-DR15 pulsed or unpulsed with KIF20A (809-833), L-DR15 pulsed with KIF20A (809-833) in the presence of anti-HLA-DR or anti-HLA class I-blocking mAb, or L-DR8 pulsed or unpulsed with KIF20A (809-833) (right panel). HLA types of the donors were indicated at the top of each panel. Data are presented as the mean+/−SD of duplicate or triplicate assays. Representative data from at least three independent experiments with similar results are shown.
Figure 2E:
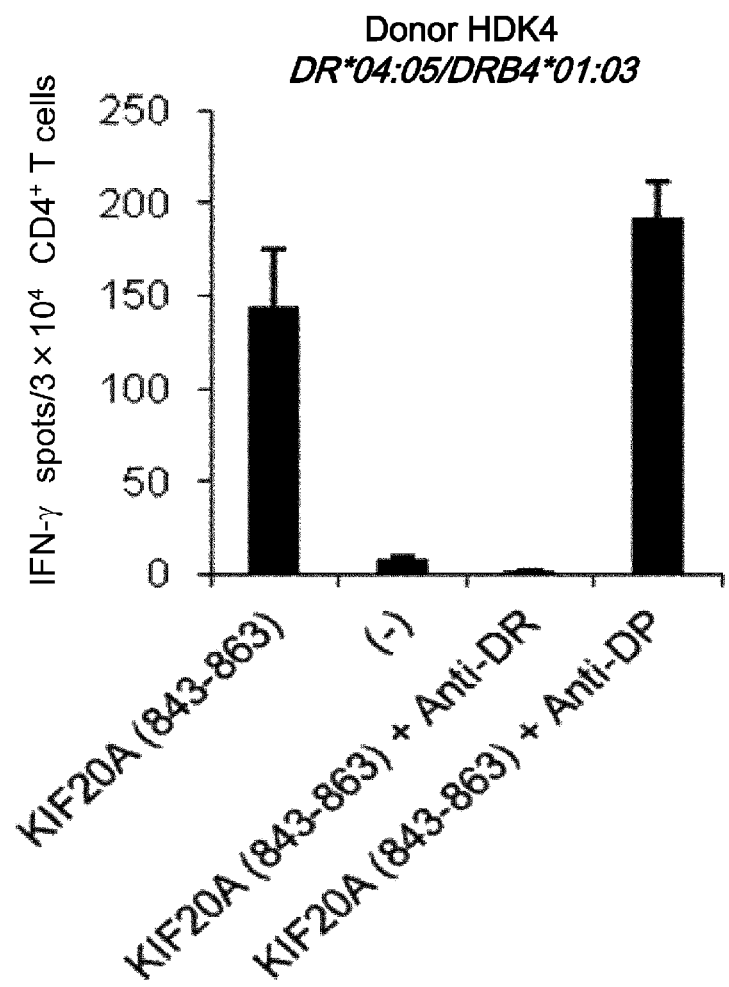
[FIG. 2E] In part E, responses against KIF20A (843-863)-pulsed autologous PBMCs are shown for an HLA-DR4- and DR53-positive healthy donor. The CD4$^+$ T cells were stimulated with PBMC alone (−), PBMC pulsed with KIF20A (843-863) (10 micro g/ml), or PBMC pulsed with KIF20A (843-863) in the presence of 5 micro-g/ml of mAb specific to HLA-DR or HLA-DP.

Next, the inventors assessed whether another peptide, KIF20A (809-833) was able to generate specific Th1 cell. CD4+ T cells of PBMCs from three healthy donors were stimulated at weekly intervals with autologous DCs and PBMCs pulsed with KIF20A (809-833), and KIF20A (809-833)-specific responses of the cultured CD4+ Th cells were examined in IFN-gamma ELISPOT assays. In an HLA-DR53-positive healthy donor HDK1, the generated Th cell lines specifically produced a significant amount of IFN-gamma in response to KIF20A (809-833)-pulsed PBMCs (FIG. 2A) and this response was significantly reduced when HLA-DR-specific mAb was added, whereas HLA-DP-specific mAb showed no effect. To further analyze the HLA-restriction, the inventors tested the reactivity of Th cells against peptide-pulsed L-DR4 or L-DR53 cells. Bulk Th cell lines generated from a DR53-positive healthy donor specifically recognized L-DR53 cells pulsed with KIF20A (809-833), but not L-DR53 cells, L-DR4 cells or KIF20A (809-833) peptide-pulsed L-DR4 cells. The IFN-gamma production of Th cell line against KIF20A (809-833)-pulsed L-DR53 cells was significantly inhibited by addition of anti-HLA-DR mAb, but not the anti-HLA-class I mAb (FIG. 2C). These results clearly indicated that KIF20A (809-833) was presented by HLA-DR53.

To investigate KIF20A (809-833) can bind another HLA class II molecule and induce Th cell responses, CD4+ T cells from two HLA-DR4-negative and HLA-DR15-positive healthy donor were stimulated with KIF20A (809-833)-pulsed autologous DC and PBMC. The generated Th cell by stimulations with KIF20A (809-833) specifically produced a significant amount of IFN-gamma in response to KIF20A (809-833)-pulsed PBMC and L-DR15 cells, but not unpulsed PBMCs and KIF20A (809-833) peptide-pulsed L-DR8 cells (FIGS. 2A and C). This IFN-gamma production of Th cell line was significantly inhibited by addition of anti-HLA-DR mAb, but not anti-HLA-DP, anti-HLA-DQ or anti-HLA-class I mAb. These results indicated that this Th cell was restricted by HLA-DR15.

Taken together, these results presented here clearly demonstrate that two LPs containing CTL-epitopes, KIF20A (60-84) and KIF20A (809-833), have capability to stimulate HLA-DR15, -DR53 and -DP2-restricted Th cells, suggesting that these LPs can be presented to Th cells by promiscuous HLA class II molecules and would be available for cancer immunotherapy of many patients.

The present inventors also assessed whether other two selected synthetic LPs that not containing CTL epitopes, KIF20A (494-517) and KIF20A (843-863), were able to generate KIF20A-specific Th cells. These two LPs could induce HLA-DR-restricted and peptide-specific Th cells from two healthy donors (FIG. 2D, E)

KIF20A (60-84) and KIF20A (809-833) Peptide Stimulates Th1-Type CD4+ T Cells

Figure 3B:
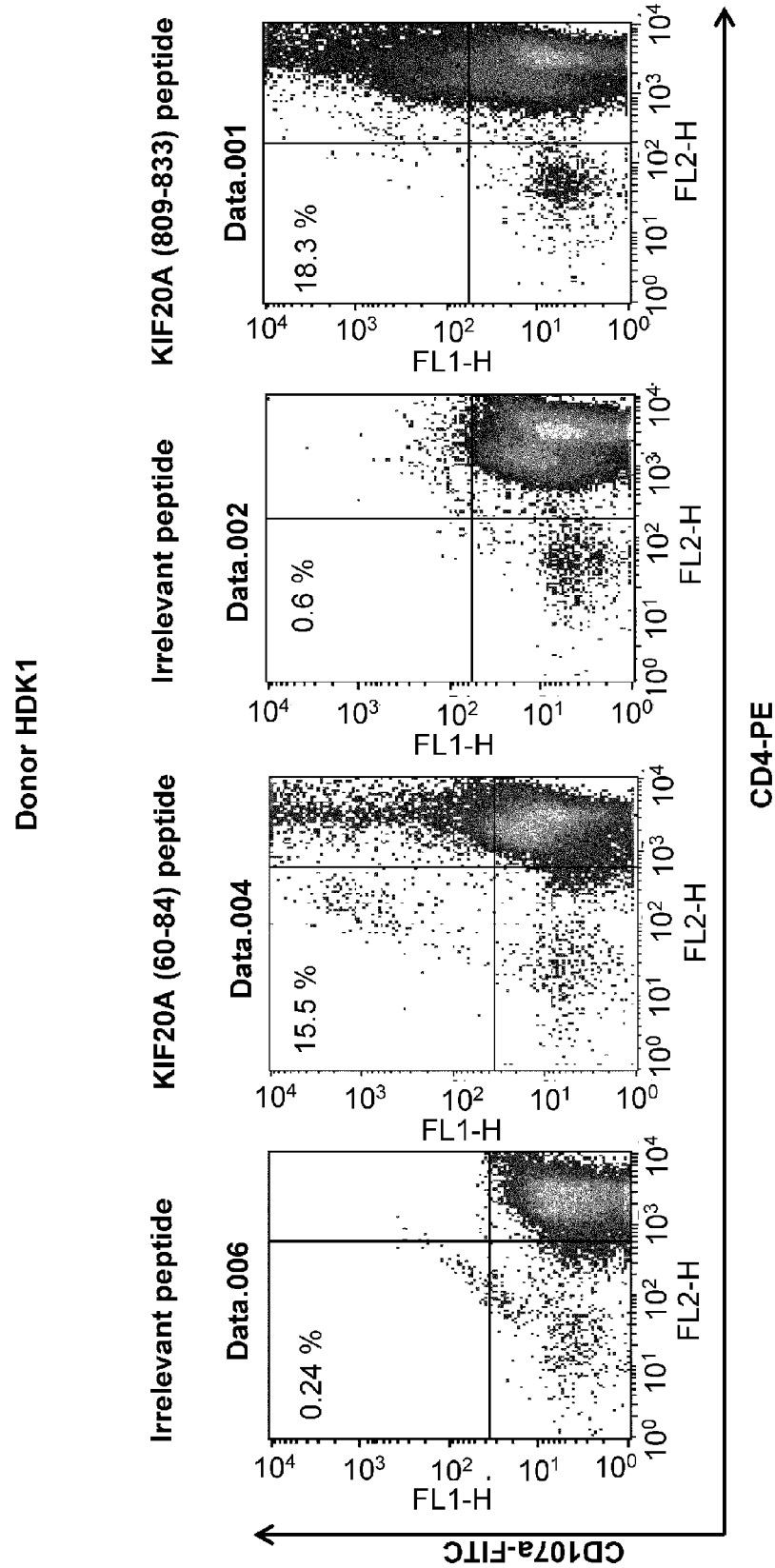
[FIG. 3B] In part B, detection of CD107a exposed on the cell surface of CD4$^+$ T cells after antigenic stimulation. Cells were restimulated with KIF20A (60-84), KIF20A (809-833) or irrelevant peptide. The numbers inside the plots indicate the percentage of the cell population with the quadrant characteristic (CD4$^+$ CD107a$^+$ T cells).

To further characterize KIF20A peptide-induced Th cells, the inventors measured several cytokines in response to the stimulation of KIF20A-specific bulk CD4+ Th cell line with cognate peptide by Bio-Plex system. Two KIF20A-specific bulk Th line from the donor HDK1 produced a large amount of IFN-gamma, TNF-alpha, GM-CSF, MIP-1beta and IL-2, but less IL-4 and IL-17 by the restimulation with cognate peptide-pulsed PBMC (KIF20A (60-84)) or L-DR53 (KIF20A (809-833)) indicating Th1 polarized characteristics (FIG. 3A).

Interestingly, the cytotoxicity marker CD107a could also be detected on KIF20A-specific bulk Th cell lines stimulated with cognate peptide (FIG. 3B), as it was shown for antiviral CD4+ effectors and tumor-infiltrating lymphocytes (Casazza J P, et al. J Exp Med 2006; 203: 2865-77.; Attig S, et al. Cancer Res 2009; 69: 8412-9.; Widenmeyer M, et al. Int J Cancer; 131: 140-9.). Altogether, these data suggest that KIF20A-specific Th cells can exert helper function and direct cytotoxic activity, which are both advantageous for cancer immunotherapy approaches.

KIF20A (60-84) and KIF20A (809-833) are Naturally Processed Epitopes

The inventors proceeded to assess whether autologous DC would be able to take up and process the KIF20A protein to stimulate KIF20A-derived peptide-specific Th cell clones. The KIF20A (60-84) LP-loaded mature DCs were prepared and used as APCs in IFN-gamma ELISPOT assays. As shown in FIG. 4A, an HLA-DR15-restricted KIF20A (60-84)-reactive Th cell clone efficiently recognized DC loaded with KIF20A protein and specifically produced IFN-gamma, but did not recognize control protein-loaded DC or protein-unloaded DC. In addition, the capacity of this Th cell clone to recognize naturally processed KIF20A antigen presented by DC was effectively blocked by anti-HLA-DR antibodies, but not by control anti-HLA-class I antibodies confirming that the epitope was presented via HLA-DR15 molecules. A similar analysis was performed using an HLA-DP2-restricted and KIF20A (60-84)-reactive Th cell clone. This Th cell clone specifically recognized KIF20A protein-loaded DC and the IFN-gamma production of Th cell clone was significantly inhibited by addition of anti-HLA-DP mAb, but not the anti-HLA-class I mAb, suggesting that the HLA-DP2-restricted Th cell epitope was also naturally processed from KIF20A protein in DC (FIG. 4B).

The HLA-DR53-restricted KIF20A (809-833)-reactive Th cell clone specifically responded to KIF20A protein-loaded DC, but not control protein-loaded DC. In addition, this response of Th cell was effectively blocked by anti-HLA-DR antibodies, but not by control anti-HLA-class I antibodies confirming that the epitope was presented via HLA-DR53 molecules.

In summary, the overall results indicate that the Th cell epitopes, KIF20A (60-84) and KIF20A (809-833) are naturally processed by DC from KIF20A-protein and presented by HLA-class II molecules on the cell surface of DC.

Figure 5A:
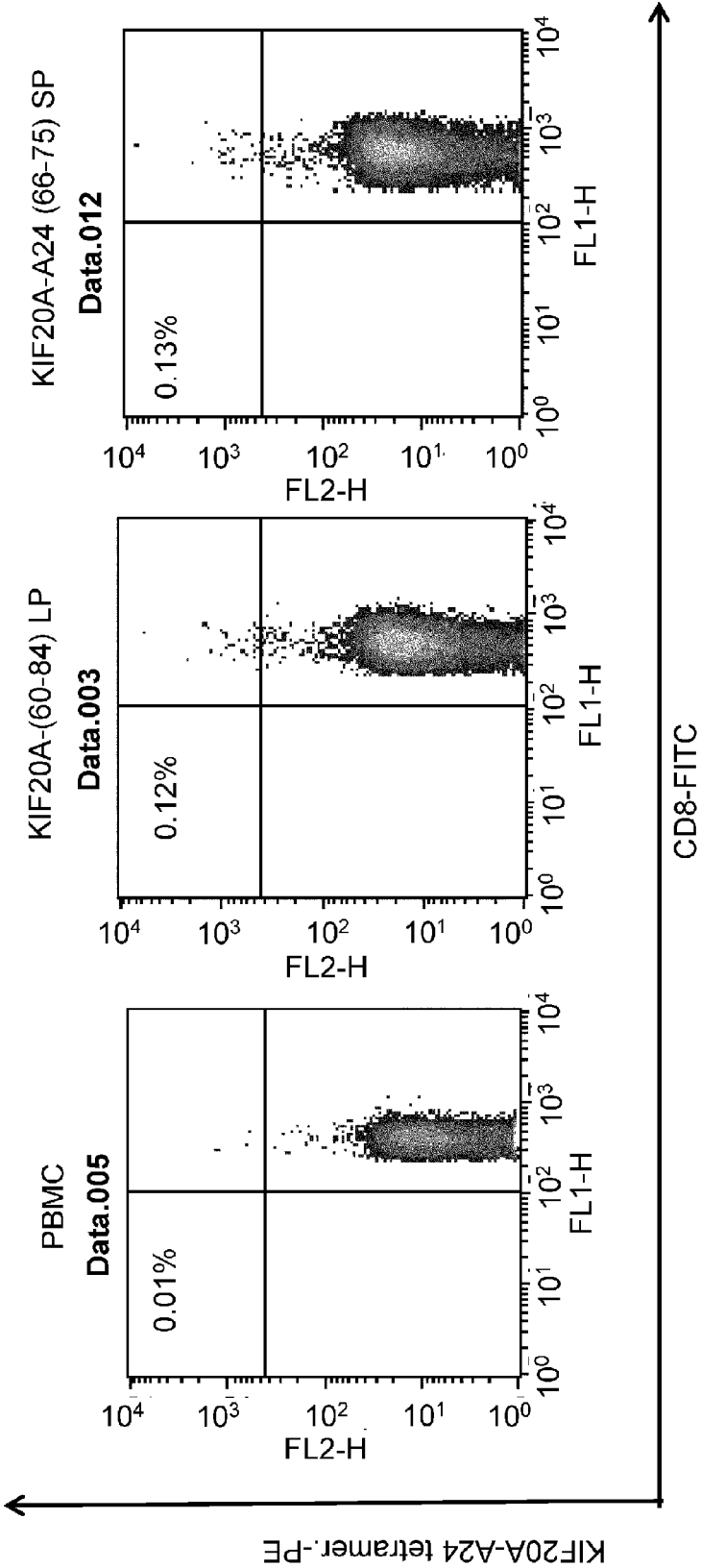
[FIG. 5A]

The KIF20A (60-84) LP Stimulate the Expansion of KIF20A-A24 (66-75) SP-Specific CD8+ T Cells In Vitro The capacity of the KIF20A (60-84) LP to stimulate the expansion of KIF20A-A24 (66-75)-specific CD8+ T cells was then examined. Twice stimulations of PBMC with 7 micro-M of the KIF20A (60-84) LP induced an expansion of HLA-A24-restricted KIF20A-A24 (66-75) SP-specific CD8+ T cells as well as the stimulations of PBMC with 7 micro-M of the KIF20A-A24 (66-75) SP in a majority of the culture wells as measured by tetramer labeling (FIG. 5A). The absolute numbers of CD8+ tetramer+ cells were also significantly increased by stimulations of PBMC with KIF20A (60-84) LP as well as the stimulations of PBMC with KIF20A-A24 (66-75) SP (FIG. 5B). Importantly, KIF20A-A24 (66-75) SP-specific IFN-gamma production of the culture well of PBMC stimulated with the KIF20A (60-84) LP was detected (FIG. 5C).

Enhanced Induction of KIF20A-Specific CTLs by KIF20A-Specific CD4+ T-Cells

The inventors also tested whether KIF20A-LPs could enhance induction of KIF20A-A2 (809-817) SP-specific CTLs. When PBMCs from an HLA-A2+/DP2+/DR53+ donor (HDK1) were stimulated with KIF20A-A2 (809-817) SP alone (SP), the frequency of KIF20A-A2 (809-817) SP-specific tetramer+ cells was 0.24% of CD8+ T-cells (data not shown). Addition of KIF20A (60-84) LP into the SP culture (SP+LP) induced a slight increase in the frequency of tetramer+ cells. In contrast, when the PBMCs were co-stimulated with KIF20A-A2 (809-817) SP, KIF20A (60-84) LP, and KIF20A (60-84) LP-specific Th-clone (SP+LP+Th-clone), the frequency of KIF20A-A2 (809-817) SP-specific CTLs increased significantly to 0.87% (data not shown).

Figure 7A:
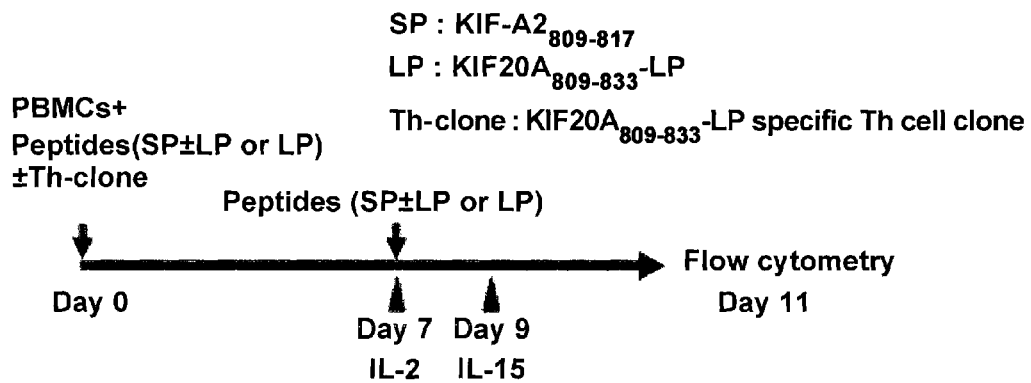
[FIG. 7A]
Figure 7B:
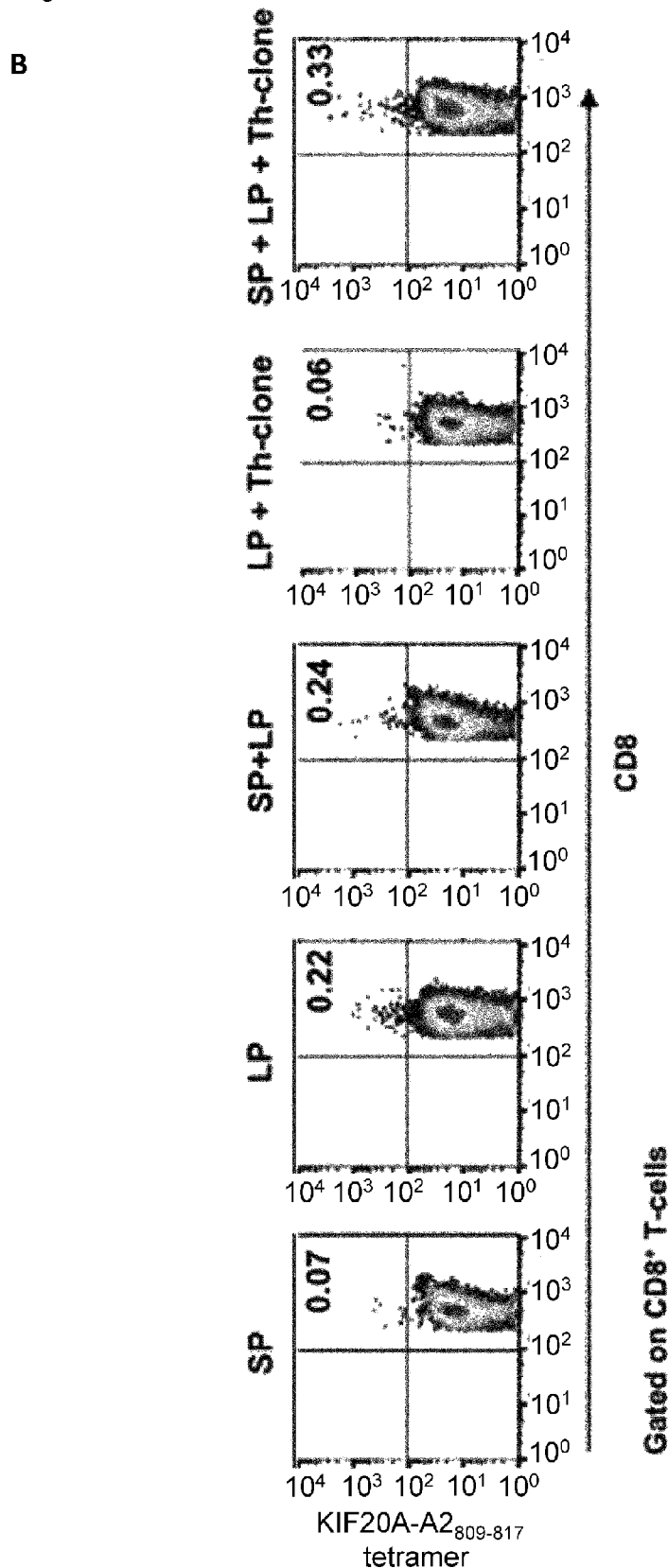
[FIG. 7B] In Part B, Representative KIF20A-A2 (809-817) SP-specific tetramer staining (gated on CD8+ T-cells) obtained from 3 independent experiments with similar results is shown.

As shown in FIG. 7A-B, KIF20A (809-833) LP alone (LP), which encompasses KIF20A-A2 (809-817) SP, or addition of KIF20A (809-833) LP into the SP culture (SP+LP) induced a slight increase in the frequency of KIF20A-A2 (809-817) SP-specific CTLs. On the other hand, the KIF20A (809-833) LP-specific Th-clone rapidly increased in response to the KIF20A (809-833) LP when both LP and Th-clone were added into the PBMCs without KIF20A-A2 (809-817) SP (LP+Th-clone) and then the increase of frequency of KIF20A-A2 (809-817) SP-specific CTLs could not be detected. The present inventors also observed that the stimulation of PBMCs with KIF20A-A2 (809-817) SP, KIF20A (809-833) LP, and KIF20A (809-833) LP-specific Th-clone (SP+LP+Th-clone) most strongly enhanced induction of KIF20A-A2 (809-817) SP-specific tetramer+ T-cells. These results indicate that the activated Th1 cells enhanced induction of KIF20A-specific CTLs in the presence of KIF20A-A2 (809-817) SP.

Next, the inventors examined that the CD107a expression of KIF20A-A24 (66-75) SP-specific CTLs cultured in the presence of KIF20A (809-833) LP-specific Th cells stimulated with the relevant LP for 1 week to assess the function of KIF20A-specific CTLs expanded by activated KIF20A-specific Th cells. KIF20A (809-833) LP-specific bulk CD4+ T-cells and KIF20A-A24 (66-75) SP-specific bulk CD8+ T-cells derived from HLA-A24+ and HLA-DR15+ (HDK5) were cultured with autologous DCs in the presence of KIF20A-A24 (66-75) SP (SP alone), KIF20A-A24 (66-75) SP+Control LP (Control LP+SP), or KIF20A-A24 (66-75) SP+KIF20A (809-833) LP (KIF20A (809-833)-LP+SP) without addition of any cytokine. After 1-week in vitro culture with peptides, the cultured cells were stained with tetramer of the HLA-A*24:02/KIF20A-A24 (67-75) complex, anti-human CD107a mAb, and anti-human CD8 mAb as described in the Materials and Methods section. As shown in FIG. 7C, the addition of KIF20A-A24 (66-75) SP+KIF20A (809-833) LP (KIF20A (809-833)LP+SP) significantly increased the absolute number of KIF20A-A24 (66-75) SP-specific CD8+ T-cells compared with the addition of KIF20A-A24 (66-75) SP alone (SP) or KIF20A-A24 (66-75) SP+Control LP (Control LP+SP). The absolute number of KIF20A-A24 (66-75) SP-specific CTLs expressing CD107a on the cell surface after re-stimulation with KIF20A-A24 (66-75) SP was also significantly augmented by the addition of KIF20A-A24 (66-75) SP+KIF20A (809-833)LP (KIF20A (809-833)LP+SP; FIG. 7D). These results suggest that activated KIF20A-LP-specific Th cells enhanced induction of KIF20A-A24 (66-75) SP-specific CTLs expressing CD107a.

The KIF20A (809-833) LP-Loaded DC can Stimulate KIF20A-A2 (809-817)-Specific CD8+ T Cells In Vitro and In Vivo Next, the inventors assessed whether the KIF20A (809-833) LP could stimulate KIF20A-A2 (809-817) SP-specific CTLs by the LP-loaded DC in vitro. To confirm this, the inventors generated KIF20A-A2 (809-817) SP-specific CTLs from peripheral blood CD8+ T cells derived from an HLA-A2-positive donor by stimulation with the KIF20A-A2 (809-817) SP as described previously (Tomita Y, et al. Cancer Sci; 102: 71-8.). The frequency of CD8+ T cells specific to the KIF20A-A2 (809-817) SP in the resulting CTL lines was examined by IFN-gamma ELISPOT assay (FIG. 6A).

The ability of stimulation of KIF20A-A2 (809-817) SP-specific CTL by KIF20A-A2 (809-833) LP-loaded autologous DC was evaluated by the IFN-gamma production of KIF20A-A2 (809-817) SP-specific bulk CTLs. As shown in FIG. 6B, the KIF20A-A2 (809-817) SP-specific CTLs specifically produced IFN-gamma in response to re-stimulation with KIF20A (809-833) LP-loaded DC, but not with irrelevant LP-loaded DC or LP-unloaded DC. The specific-IFN-gamma production was significantly inhibited by addition of anti-HLA-class I mAb, but not the anti-HLA-DR mAb, thus indicating that the inventors successfully stimulated KIF20A-A2 (809-817) SP-specific CD8+ T cells possibly through the cross-presentation of LP by DC in vitro.

Figure 6C:
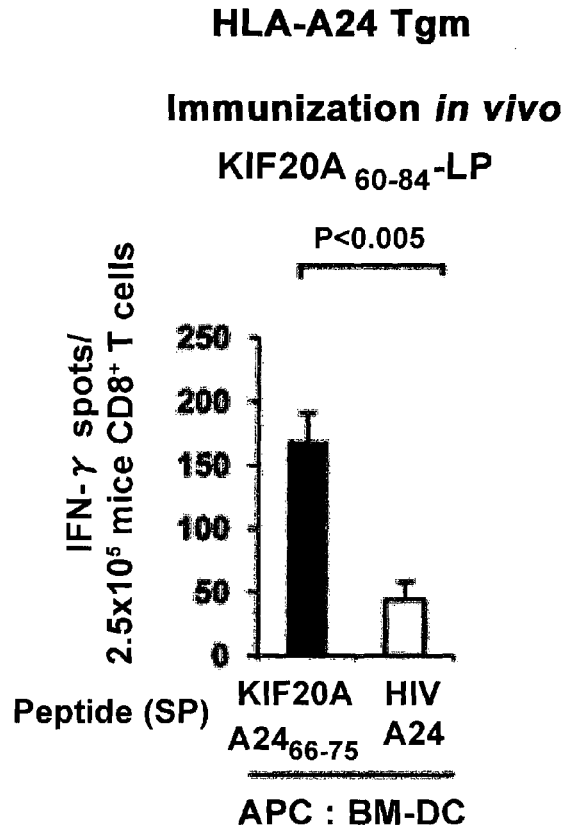
[FIG. 6C] In Part C, Induction of KIF20A-A24 (66-75) SP-specific CTLs in mice immunized with KIF20A (60-84) LP. HLA-A24 Tgm were immunized with KIF20A (60-84) LP. After the third vaccination with KIF20A (60-84) LP, mouse CD8$^+$ T-cells in the inguinal lymph nodes were stimulated with BM-DC pulsed with KIF20A-A24 (66-75) SP. The number of IFN-gamma producing murine CD8+ T-cells was analyzed by ex vivo ELISPOT assay. Representative data from 5 independent experiments with similar results are shown.

The capacity of KIF20A (60-84) LP to prime KIF20A-A24 (66-75) SP-specific CTLs in vivo was examined by an ex vivo IFN-gamma ELISPOT assay. HLA-A24 Tgm were immunized three times with KIF20A (60-84) LP. The CD8+ T-cells of HLA-A24 Tgm vaccinated with KIF20A (60-84) LP produced IFN-gamma in response to stimulation with BM-DCs pulsed with the KIF20A-A24 (66-75) SP (FIG. 6C). These results suggest that after uptake of KIF20A (60-84) LP, APCs cross-prime KIF20A-A24 (66-75) SP-specific CTLs in vitro and in vivo.

Presence of KIF20A-Specific Th1 Cells in Patients with HNMT Receiving Immunotherapy with TAA-Derived CTL-Epitope Peptides.

To the best of our knowledge, no studies have examined KIF20A expression in HNMT. Immunohistochemical analysis of KIF20A expression was performed on 56 cases of HNMT (39 squamous cell carcinoma, 14 adenoid cystic carcinoma, 2 osteosarcoma, and 1 angiosarcoma tissue specimens). Twenty-six of the 39 head and neck squamous cell carcinomas (67%), 4 of the 14 adenoid cystic carcinomas (29%), and 1 of the 2 osteosarcoma (50%) showed positive expression of KIF20A. No staining was detected in the benign tumor samples.

Figure 8A:
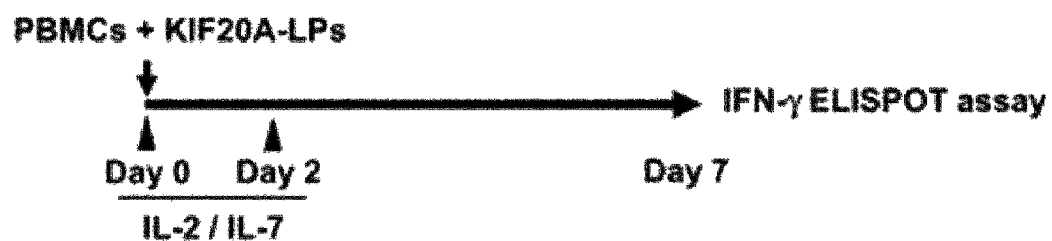
[FIG. 8A]
Figure 8E:
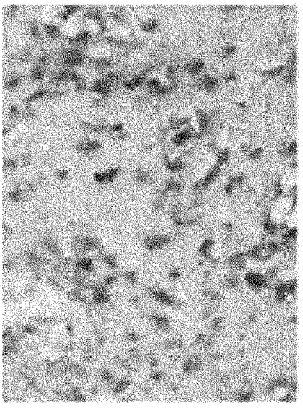
[FIG. 8E] In Part E, Immunohistochemical analyses of the KIF20A protein in cancer tissues and osteosarcoma (original magnification ×400). Positive KIF20A immunohistochemical staining on tissue sections of adenoid cystic carcinoma in HNMT31 and osteosarcoma in HNMT108 are shown. Negative KIF20A immunohistochemical staining on tissue sections of squamous cell carcinoma in HNMT102 and osteosarcoma in HNMT107 are also shown. Malignant cells positive for KIF20A showed homogeneous cytoplasmic staining. Expression of KIF20A in HNMT tissues was associated with KIF20A-LPs-specific Th1 cell responses in patients with HNMT.

In context of cancer immunotherapy, there is strong evidence suggesting that vaccines using restricted epitopes can result in broad CD8+ T-cell responses to antigens not present in the vaccine (Corbiere V et al. Cancer Res 2011; 71:1253-62., Ribas A et al. Trends Immunol 2003; 24:58-61. Hunder N N et al. N Engl J Med 2008; 358:2698-703.). Thus, the present inventors considered that KIF20A-specific Th cell responses may be induced by vaccination with TAA-derived CTL-epitope peptides, which do not include KIF20A-derived SPs. The inventors assessed T-cell responses specific for KIF20A in peripheral blood from 16 patients who were receiving immunotherapy for treatment of HNMT. The donor characteristics are summarized in FIG. 8F. After 1 week of in vitro stimulation of PBMCs with KIF20A-LPs, the frequency of individual KIF20A-LP-specific T-cells was detected by IFN-gamma ELISPOT assay (FIG. 8A). PBMCs isolated from 9 healthy volunteers were used as controls. Responses were considered positive when the number of IFN-gamma-secreting cells was at least 2-fold above the negative control. KIF20A-specific Th cell responses were observed in 8 of 16 patients (KIF20A (60-84) LP, 2 of 16, 13%; KIF20A (809-833) LP, 7 of 16, 44%), but no specific immune responses to KIF20A-LPs were detected in the 9 healthy donors (FIG. 8F). The present inventors also found that the number of specific spots against KIF20A (60-84) LP and KIF20A (809-833) LP in patients were significantly larger than in healthy donors (FIG. 8B). KIF20A (809-833) LP-specific IFN-gamma production by T-cells in HNMT31 and HNMT43 was significantly inhibited by addition of anti-HLA-DR mAb but not by anti-HLA-class I mAb (FIG. 8C). Interestingly, specific responses to KIF20A (809-833) LP were augmented in some patients (HNMT31 and 42), or induced in HNMT43 during the course of immunotherapy (FIG. 8D). As shown in FIG. 8E, KIF20A antigen was expressed in patients with HNMT in whom KIF20A-specific Th1 cell responses were detected (FIG. 8F, HNMT31 and HNMT108), but was not expressed in those for whom KIF20A-specific Th1 cell responses were not detected (FIG. 8F, HNMT102 and 107). These observations suggest that APCs collected and processed a KIF20A antigen derived from tumor cells expressing KIF20A, and then activated KIF20A-specific Th1 cells in vivo.

DISCUSSION

It is considered that the most attractive vaccine compounds are synthetic LPs corresponding to the sequence of TAAs that can induce therapeutic CD4+ and CD8+ responses (Kenter G G, et al. N Engl J Med 2009; 361: 1838-47.; Melief C J and van der Burg S H. Nat Rev Cancer 2008; 8: 351-60.). Following the injection of these LPs, the patient's DCs will take up the LPs, process them and present all possible CTL-epitopes and Th-epitopes in the context of various HLA class I and HLA class II molecules, respectively. Thus, the present inventors considered that an ideal peptide vaccine for cancer immunotherapy should be a single polypeptide that can induce both CTL and Th1 cell restricted by the frequent HLA in the population.

In this study, the inventors identified two KIF20A-derived LPs including CTL-epitopes recognized by promiscuous HLA-class II-restricted Th1 cells, and these Th1 cells induced by the LPs responded to recombinant KIF20A protein in the presence of dendritic cells (DC) indicating that this Th1 cell epitope can be naturally processed in DC. Interestingly, these Th1 epitopes containing CTL epitopes could stimulate KIF20A-specific CTLs, suggesting these LPs containing CTL epitopes were cross-presented to KIF20A-specific CTLs in vitro human culture system.

These results indicate a potential synergistic effect of immunotherapy using KIF20A-specific Th epitope together with CTL-epitopes. Taken together, KIF20A-derived Th epitopes in combination with CTL-epitopes are suggested to be applicable for immunotherapy of various cancer patients.

In conclusion, the present inventors first identified KIF20A-derived helper peptides including CTL-epitopes, which not only become a good tool for propagating and activating KIF20A-specific Th1 cell but also KIF20A-specific CTLs. These findings would contribute to a clinical trial of KIF20A-peptide-based immunotherapy for patients with various types of cancers in the future.

INDUSTRIAL APPLICABILITY

The present invention describes Th1 cell epitope peptides derived from KIF20A that can induce potent anti-tumor immune responses and thus have applicability to a wide array of cancer types. Such peptides warrant further development as peptide vaccines against cancer, especially against cancers expressing KIF20A. The peptides of the present invention can induce the Th1 cell response and thus cytokines secreted by Th1 cells can help or activate any immune cells responsible for cellular immunity in an antigen independent manner. Therefore, immunotherapeutic strategy provided by the present invention can be applied to any diseases including cancers, as long as the disease can be improved via immune responses mediated by MHC class II molecules. In particular, Th1 cells of the present invention can improve immunological responses raised by CTLs. Therefore, the peptide of the present invention would be beneficial to enhance CTL response against diseases including cancers in a subject.

Moreover, in preferred embodiments, the peptides of the present invention can also induce CTLs against KIF20A expressing cells, as well as Th1 cells. Such peptide of the present invention can be also useful for the treatment of diseases associated with KIF20A, e.g. cancers, more particularly, bladder cancer, breast cancer, cholangiocellular carcinoma, esophageal cancer, non-small cell lung cancer (NSCLC), pancreatic cancer, prostate cancer, renal carcinoma, small cell lung cancer (SCLC) and head-and-neck malignant tumor (HNMT).

While the present invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

The invention claimed is:

1. An isolated peptide consisting of 10-30 amino acids in length and comprising a part of the amino acid sequence of SEQ ID NO: 11, wherein said peptide comprises a contiguous amino acid sequence having more than 9 amino acids in length selected from the amino acid sequence of SEQ ID NO: 2 in which one or two amino acids are substituted and/or added;
wherein said peptide has ability to induce T helper type 1 (Th1) cells.

2. The isolated peptide of claim 1, wherein the peptide or fragment thereof has abilities to bind at least two kinds of MHC class II molecules.

3. The isolated peptide of claim 2, wherein the MHC class II molecules are selected from the group consisting of HLA-DR4, HLA-DR15, HLA-DR53 and HLA-DP2.

4. The isolated peptide of claim 1, wherein said peptide comprises an amino acid sequence of a peptide having KIF20A-specific cytotoxic T lymphocyte (CTL) inducibility.

5. The isolated peptide of claim 4, wherein said peptide comprises the amino acid sequence of SEQ ID NO: 2 in which one or two amino acids are substituted and/or added.

6. A composition comprising one or more peptide(s) consisting of 10-30 amino acids in length and comprising a part of the amino acid sequence of SEQ ID NO: 11, wherein said peptide comprises an amino acid sequence selected from the group consisting of:
(a) a contiguous amino acid sequence having more than 9 amino acids in length selected from the amino acid sequence of SEQ ID NO: 2; and
(b) an amino acid sequence in which one or two amino acids are substituted, and/or added in the amino acid sequence of SEQ ID NO: 2
in combination with an adjuvant.

7. The composition of claim 6, wherein said composition further comprises one or more peptides having CTL inducibility.

8. A method for inducing an APC having an ability to induce a Th1 cell, said method comprising a step of contacting an APC with the peptide of claim 1 in vitro, ex vivo or in vivo.

9. A method for inducing an APC having an ability to induce a CTL, said method comprising a step of contacting an APC with the peptide of claim 1 in vitro, ex vivo or in vivo.

10. A method for inducing a Th1 cell, said method comprising a step of co-culturing a CD4-positive T cell with an APC that presents on its surface a complex of an MHC class II molecule and the peptide of claim 1 or fragment thereof.

11. A method for inducing a CTL, said method comprising the step selected from the group consisting of:
(a) co-culturing both of a CD4-positive T cell and a CD8-positive T cell with APCs contacted with the peptide of claim 4; and
(b) co-culturing a CD8-positive T cell with an APC contacted with the peptide of claim 4.

12. A method for enhancing an immune response mediated by an MHC class II molecule, wherein the method comprises a step of administering to a subject one or more peptide(s) of claim 1.

13. A method of inducing an immune response against cancer in a subject in need thereof, said method comprising the step of administering to the subject a composition comprising one or more peptide(s) of claim 1.

14. The isolated peptide of claim 4, consisting of the amino acid sequence of SEQ ID NO: 2 in which one or two amino acids are substituted and/or added.

* * * * *

UNITED STATES PATENT AND TRADEMARK OFFICE
CERTIFICATE OF CORRECTION

| | | |
|---|---|---|
| PATENT NO. | : 9,561,265 B2 | Page 1 of 1 |
| APPLICATION NO. | : 14/413403 | |
| DATED | : February 7, 2017 | |
| INVENTOR(S) | : Yasuharu Nishimura, Yusuke Tomita and Ryuji Osawa | |

It is certified that error appears in the above-identified patent and that said Letters Patent is hereby corrected as shown below:

On the Title Page

Under abstract "14 Claims, 23 Drawing Sheets" should read --15 Claims, 23 Drawings Sheets--.

In the Claims

Column 75, Lines 42-53, (approx.), should read:
6. A composition comprising one or more peptide(s) having the ability to induce T helper type 1 (Th1) cells, the peptide(s) consisting of 10-30 amino acids in length and comprising a part of the amino acid sequence of SEQ ID NO: 11, wherein said peptide comprises an amino acid sequence selected from the group consisting of:
    (a) a contiguous amino acid sequence having more than 9 amino acids in length selected from the amino acid sequence of SEQ ID NO: 2; and
    (b) an amino acid sequence in which one or two amino acids are substituted, and/or added in the amino acid sequence of SEQ ID NO: 2 in combination with an adjuvant.

Column 76, Lines 29-33, (approx.), should read:
10. A method for inducing a Th1 cell, said method comprising a step of co-culturing a CD4-positive T cell with an APC that presents on its surface a complex of an MHC class II molecule and the peptide of claim 1.

Column 76, Line 52, (approx.), please insert:
--15. The composition of claim 6, wherein the peptide consists of the amino acid sequence of SEQ ID NO:2.--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*